United States Patent
Nojima et al.

(10) Patent No.: US 12,258,308 B2
(45) Date of Patent: *Mar. 25, 2025

(54) BENZENE DERIVATIVE

(71) Applicant: ONO PHARMACEUTICAL CO., LTD., Osaka (JP)

(72) Inventors: Shoji Nojima, Osaka (JP); Kenji Sasaki, Osaka (JP); Tohru Kambe, Osaka (JP); Takashi Konemura, Osaka (JP); Yoshikazu Goto, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 610 days.

This patent is subject to a terminal disclaimer.

(21) Appl. No.: 17/544,616

(22) Filed: Dec. 7, 2021

(65) Prior Publication Data

US 2022/0089532 A1    Mar. 24, 2022

Related U.S. Application Data

(63) Continuation of application No. 17/264,603, filed as application No. PCT/JP2019/029883 on Jul. 30, 2019, now Pat. No. 11,261,154.

(30) Foreign Application Priority Data

Jul. 31, 2018 (JP) .................. 2018-143024

(51) Int. Cl.
    *C07C 311/21*      (2006.01)
(52) U.S. Cl.
    CPC ................. *C07C 311/21* (2013.01)
(58) Field of Classification Search
    CPC .................................................. C07C 311/21
    See application file for complete search history.

(56) References Cited

U.S. PATENT DOCUMENTS

| 5,453,443 | A | 9/1995 | Perrier et al. | |
| 8,455,519 | B2 | 6/2013 | Alisi et al. | |
| 11,261,154 | B2 * | 3/2022 | Nojima | C07D 213/76 |

FOREIGN PATENT DOCUMENTS

| CN | 105622488 A | 6/2016 |
| EP | 0 947 500 A1 | 10/1999 |
| JP | 2011-503030 A | 1/2011 |
| WO | WO-03/016254 A1 | 2/2003 |
| WO | WO-2006/000288 A1 | 1/2006 |
| WO | WO-2006/113471 A2 | 10/2006 |
| WO | WO-2017/068070 A1 | 4/2017 |

OTHER PUBLICATIONS

International Searching Authority, "International Search Report," issued in connection with International Patent Application No. PCT/JP2019/029883, dated Oct. 21, 2019.
International Searching Authority, "Written Opinion," issued in connection with International Patent Application No. PCT/JP2019/029883, dated Oct. 21, 2019.

* cited by examiner

*Primary Examiner* — Amanda L. Aguirre
*Assistant Examiner* — William Y Lee
(74) *Attorney, Agent, or Firm* — Foley & Lardner LLP

(57) ABSTRACT

A compound represented by general formula (I) (in the formula, all symbols are as described in the description) or a salt thereof has a potent nerve-protecting and/or -repairing activity, and therefore can be used as a therapeutic agent for neuropathy (e.g., chronic inflammatory demyelinating polyneuropathy, Guillain-Barre syndrome, periarteritis nodosa, allergic vasculitis, diabetic peripheral neuropathy, entrapment neuropathy, peripheral neuropathy associated with the administration of a chemotherapeutic drug, or peripheral neuropathy associated with Charcot-Marie-Tooth disease).

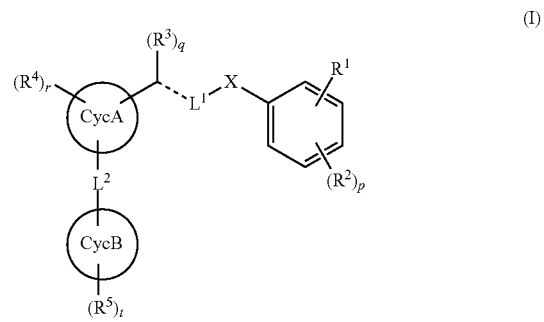

12 Claims, 1 Drawing Sheet

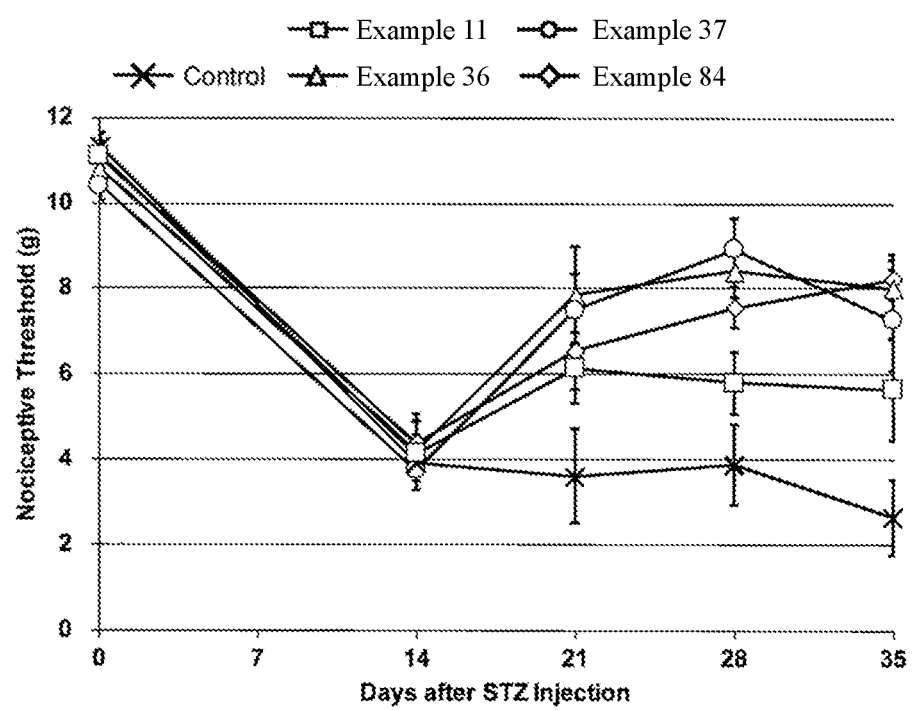

BENZENE DERIVATIVE

CROSS-REFERENCE TO RELATED APPLICATIONS

The present application is a Continuation of U.S. patent application Ser. No. 17/264,603, filed on Jan. 29, 2021, which claims priority under 37 U.S.C. § 371 to International Patent Application No. PCT/JP2019/029883, filed Jul. 30, 2019, which claims priority to and the benefit of Japanese Patent Application No. 2018-143024, filed on Jul. 31, 2018. The contents of these applications are hereby incorporated by reference in their entireties.

TECHNICAL FIELD

The present invention relates to a compound represented by general formula (I):

[Formula 1]

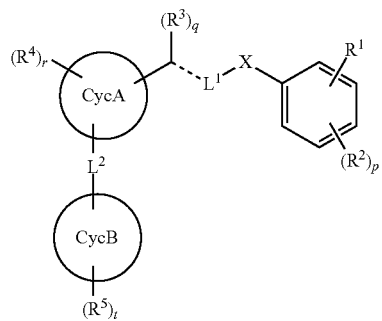

(I)

(wherein all symbols have the same meanings as described below) or a salt thereof (wherein the compound or the salt thereof is sometimes referred to as "the compound of the present invention", hereinafter).

BACKGROUND ART

Nervous systems are roughly classified into central nervous systems and peripheral nervous systems. Particularly peripheral nervous systems allow the communication of brain and spinal cord with peripheral regions of a body and are therefore involved in neural transmission. Peripheral nervous systems are classified into somatic nervous systems (cerebrospinal nervous systems) and autonomic nervous systems. The somatic nervous systems are further classified into cranial nerves and spinal nerves. From the viewpoint of functions, the somatic nervous systems are classified as follows: the fibers that transmit a neural signal (excitation) generated from a sensory receptor to the central nerves are classified into afferent or sensory nerve fibers, while the fibers that transmit a neural signal directed from the brain and spinal cord towards effector organs such as muscles and glands are classified into efferent or motor nerve fibers. The cranial nerves are peripheral nerves that extend from the brain and 12 pairs of them are known. Among the cranial nerves, some of them consist of sensory nerve fibers; some of them consist of motor nerve fibers; and some of them consist of mixed nerve fibers. The first to the twelfth nerve pairs are called as an olfactory nerve, an optic nerve, an oculomotor nerve, a trochlear nerve, a trigeminal nerve, an abducens nerve, a facial nerve, an auditory nerve, a glossopharyngeal nerve, a vagus nerve, an accessory nerve and a hypoglossal nerve, respectively. Among these nerves, the olfactory nerve, the optic nerve, the trigeminal nerve, the facial nerve, the auditory nerve, the glossopharyngeal nerve and the vagus nerve are known as nerves consisting of sensory or mixed nerve fibers. The spinal nerves are peripheral nerves that extend from the spinal cord and there are known 31 respective pairs of them, including 8 pairs of cervical nerves, 12 pairs of thoracic nerves, 5 pairs of lumbar nerves, 5 pairs of sacral nerves and one pair of coccygeal nerves. All of the spinal nerves consist of mixed nerve fibers, each containing a sensory fiber (a dorsal root) that extends toward the skin or the like and a motor fiber (a ventral root) that extends toward a skeletal muscle.

Sensory nerve fibers, i.e., sensory nerves, take over the function to accurately transfer a stimulus such as light, sound, temperature and touch received by a sensory receptor such as an optical organ, an auditory organ, an olfactory organ, a gustatory organ and skin to the central nervous system. A neural signal transferred to the central nervous system is finally transmitted to each sensory area in the cerebral cortex, such as visual area, auditory area and the like, and, as a result, a sensation is normally recognized. However, in these sensory nerves, axons, myelin sheaths, Schwann cells or the like may be damaged by a viral infection, a tumor, cancer, diabetes, ischemia, an injury, compression, a drug, a radiotherapy or the like, sometimes inducing various neuropathies including the death of cells and demyelination. As a result, a correct neurotransmission does not occur in a sensory nerve that undergoes the disorder, resulting in the development of a disease such as hearing loss and neuropathic pain. In addition to these disorders, peripheral neuropathy is also known, in which various peripheral nerves including sensory nerves are damaged simultaneously with a specific sensory nerve as the result of the experience with a disease such as a metabolic disease and an autoimmune disease, an injury, drug poisoning or the like. In this disease, a single nerve may be damaged, or two or more nerves located in different regions or a large number of nerves may be damaged simultaneously. The symptoms of this disease include pain in a peripheral region, numbness, burning sensation, decreased joint proprioception, decreased vibratory sense, pain (including neuropathic pain), abnormal sensation, coldness, hot flash and the like, and thus are very complex and varied.

However, since peripheral nerve-related diseases as mentioned above are unknown with respect to the mechanisms of development thereof or are physical nerve damages, symptomatic therapies for the purpose of ameliorating the symptoms or the like are primarily performed for the medical treatment of the diseases. There are known very little chemical substances which are clinically useful as modalities that can act directly on damaged nerve systems.

SUMMARY OF INVENTION

Technical Problems

The present invention addresses the problem of providing a compound having a nerve-protecting and/or -repairing activity.

Solutions to Problems

The present inventors have made extensive and intensive studies for solving the problem. As a result, it is found that a compound represented by general formula (I) has a potent nerve-protecting and/or -repairing activity. This finding leads to the accomplishment of the present invention.

The present invention relates to the following items:

[1] a compound represented by general formula (I):

[Formula 2]

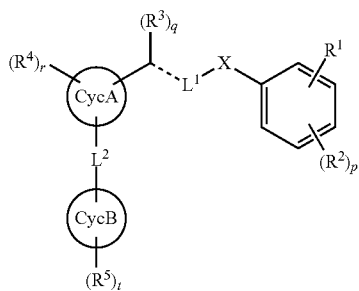

(I)

[wherein:
R$^1$ represents (1) —R$^{11}$—COOR$^{12}$, (2) —R$^{13}$—CONR$^{14}$R$^{15}$, (3) —R$^{17}$—CN, (4) —R$^{18}$—CONHS(O)$_2$—R$^{19}$, (5) —R$^{20}$-CycD, or

[Formula 3]

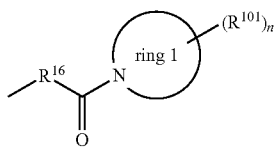

(6)

(wherein: ring 1 represents a 3-to 6-membered nitrogen-containing monocyclic saturated heterocyclic ring; R$^{101}$ represents (1) a halogen atom, (2) a C1-4 alkyl group, or (3) a C1-4 haloalkyl group, and n represents an integer of 0 to 3, wherein, when n is 2 or more, a plurality of R$^{101}$s may be the same as or different from each other);

R$^{11}$, R$^{13}$, R$^{16}$, R$^{17}$, R$^{18}$ and R$^{20}$ each independently represent (1) a C1-6 alkylene group which may be substituted by 1 to 3 halogen atoms, (2) a C2-6 alkenylene group which may be substituted by 1 to 3 halogen atoms, or (3) a C2-6 alkynylene group which may be substituted by 1 to 3 halogen atoms, wherein, when the alkylene group, the alkenylene group or the alkynylene group is a branched chain, two C1-2 alkyl groups branched from a single carbon atom may together form a C3-5 saturated carbocyclic ring;

R$^{12}$, R$^{14}$, R$^{15}$ and R$^{19}$ each independently represent (1) a hydrogen atom, (2) a C1-4 alkyl group or (3) a C1-4 haloalkyl group;

CycD represents triazole or tetrazole;

R$^2$ represents (1) a halogen atom, (2) a C1-4 alkyl group or (3) a C1-4 haloalkyl group, and p represents an integer of 0 to 3, wherein, when p is 2 or more, a plurality of R$^2$s may be the same as or different from each other;

X represents (1) CH$_2$ or (2) an oxygen atom;

L$^1$ represents (1) a linear C3-7 alkylene group which may be substituted by 1 to 4 R$^{L1a}$s, (2) a linear C3-7 alkenylene group which may be substituted by 1 to 4 R$^{L1a}$s, (3) a linear C3-7 alkynylene group which may be substituted by 1 to 4 R$^{L1a}$s or (4) (a linear C1-3 alkylene group which may be substituted by 1 to 2 R$^{L1a}$s)—O-(a linear C1-3 alkylene group which may be substituted by 1 to 2 R$^{L1a}$s);

R$^{L1a}$ represents (1) a halogen atom, (2) a hydroxyl group, (3) an oxo group, or (4) a C1-2 alkyl group, wherein: when there are at least two R$^{L1a}$s, a plurality of R$^{L1a}$s may be the same as or different from each other; and when each of two R$^{L1a}$s bonded to a single carbon atom is a C1-2 alkyl group, the C1-2 alkyl group may form a C3-5 saturated carbocyclic ring in conjunction with the carbon atom to which the C1-2 alkyl group is bonded;

[Formula 4]

- - - - - - represents a single bond, a double bond or a triple bond;

R$^3$ represents (1) a hydrogen atom, (2) a halogen atom, (3) a hydroxyl group, (4) a C1-2 alkyl group or (5) a methylidene group, and q represents an integer of 0 to 2, wherein: when

[Formula 5]

- - - - - - is a single bond and q is 2, a plurality of R's may be the same as or different from each other; and when at least one of R$^3$s is a methyl group, the methyl group may form cyclopropane in conjunction with a carbon atom in the adjacent L$^1$;

CycA represents (1) a C5-10 monocyclic or bicyclic carbocyclic ring or (2) a 5- to 10-membered monocyclic or bicyclic heterocyclic ring;

R$^4$ represents (1) a halogen atom, (2) a hydroxyl group, (3) a C1-4 alkyl group, (4) a C1-4 haloalkyl group, (5) a C1-4 alkoxy group, (6) a C1-4 haloalkoxy group, (7) a cyano group or (8) a —SO$_2$-(a C1-2 alkyl group), and r represents an integer of 0 to 6, wherein, when r is 2 or more, a plurality of R$^4$s may be the same as or different from each other;

L$^2$ represents —R$^{31}$-L$^3$-R$^{32}$—.

L$^3$ represents (1) —NR$^{201}$—S(O)—, (2) —NR$^{202}$—S(O)$_2$—, (3) —NR$^{203}$—C(O)—, (4) —CR$^{204}$(OH)—, (5) —NR$^{205}$—, (6) —S(O)— or (7) —S(O)$_2$—;

R$^{201}$, R$^{202}$, R$^{203}$, R$^{204}$ and R$^{205}$ each independently represent (1) a hydrogen atom, (2) a C1-4 alkyl group or (3) a C1-4 haloalkyl group, wherein the alkyl group or the haloalkyl group may be substituted by (1) a hydroxyl group, (2) an oxo group, (3) a C3-6 monocyclic carbocyclic ring or (4) a 3- to 6-membered monocyclic heterocyclic ring;

R$^{31}$ and R$^{32}$ each independently represent (1) a bond or (2) a C1-3 alkylene group which may be substituted by 1 to 3 substituents independently selected from the group consisting of a halogen atom, a hydroxyl group and an oxo group;

CycB represents (1) a C5-10 monocyclic or bicyclic carbocyclic ring or (2) a 5- to 10-membered monocyclic or bicyclic heterocyclic ring; and R$^5$ represents (1) a halogen atom, (2) a C1-6 alkyl group, (3) a C2-6 alkenyl group, (4) a C2-6 alkynyl group, (5) a C1-6 haloalkyl group, (6) a C2-6 haloalkenyl group, (7) a C2-6 haloalkynyl group, (8) a C1-6 alkoxy group or (9) a C1-6 haloalkoxy group, and t represents an integer of 0 to 6, wherein, when t is 2 or more, a plurality of R$^5$s may be the same as or different from each other], or a salt thereof;

[2] the compound or the salt thereof according to item [1], wherein, in general formula (I), the group:

[Formula 6]

represents (1) =CH-(a linear C2-6 alkylene group which may be substituted by 1 to 2 $R^{L1a}$s)-, (2) -(a linear C3-7 alkylene group which may be substituted by 1 to 2 $R^{L1a}$s)- or (3) -(a linear C1-3 alkylene group which may be substituted by 1 to 2 $R^{L1a}$s)-O-(a linear C1-3 alkylene group which may be substituted by 1 to 2 $R^{L1a}$s)-, (in (1) to (3), $R^{L1a}$ has the same meaning as mentioned in item [1]);

[3] the compound or the salt thereof according to item [1] or [2], wherein $R^1$ is —$R^{11}$—$COOR^{12}$;

[4] the compound or the salt thereof according to any one of items [1] to [3], wherein $L^2$ is (1) —$NR^{202}$—$S(O)_2$— or (2) —$CR^{204}(OH)$—$CH_2$—;

[5] the compound or the salt thereof according to any one of items [1] to [4], wherein CycA is a C5-6 monocyclic carbocyclic ring;

[6] the compound or the salt thereof according to any one of items [1] to [5], wherein CycB is a C5-6 monocyclic carbocyclic ring;

[7] the compound or the salt thereof according to any one of items [1] to [6], wherein general formula (I) is general formula (I-1):

[Formula 7]

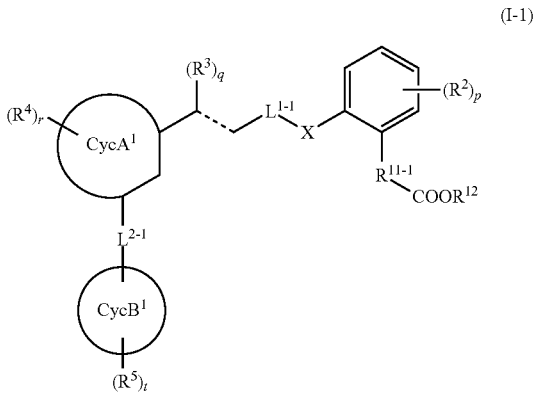

(I-1)

[wherein: $R^{11-1}$ represents a C2-4 alkylene group; $L^{1-1}$ represents a linear C3-4 alkylene group which may be substituted by 1 to 2 $R^{L1a}$s; $CycA^1$ and $CycB^1$ each independently represent a C5-6 monocyclic carbocyclic ring; $L^{2-1}$ represents (1) —NH—$S(O)_2$— or (2) —CH(OH)—$CH_2$—; and other symbols have the same meanings as mentioned in item [1]];

[8] the compound or the salt thereof according to any one of items [1] to [7], wherein X is an oxygen atom;

[9] the compound or the salt thereof according to item [1], wherein the compound or the salt thereof is (1) 3-[2-[(E,3R)-5-[3-(benzenesulfonamido)phenyl]-3-hydroxypent-4-enoxy]phenyl]propanoic acid, (2) 3-[2-[(3S)-5-[3-(benzenesulfonamido)phenyl]-3-hydroxypentoxy]phenyl]propanoic acid, (3) 3-[2-[(3R)-5-[3-(benzenesulfonamido)phenyl]-3-hydroxypentoxy]phenyl]propanoic acid, (4) 3-[2-[(E,3R)-5-[4-(benzenesulfonamido)phenyl]-3-hydroxypent-4-enoxy]phenyl]propanoic acid, (5) 3-[2-[(E,3R)-5-[3-(cyclopentylsulfonylamino)phenyl]-3-hydroxypent-4-enoxy]phenyl]propanoic acid, (6) 3-[2-[(E,3R)-5-[3-(benzenesulfonamido)-2-methylphenyl]-3-hydroxypent-4-enoxy]phenyl]propanoic acid, (7) 4-[2-[(E,3R)-5-[3-(benzenesulfonamido)phenyl]-3-hydroxypent-4-enoxy]phenyl]butanoic acid, (8) 3-[2-[(E)-4-[3-(benzenesulfonamido)phenyl]-2-hydroxybut-3-enoxy]phenyl]propanoic acid, (9) (R)-3-[2-[(E)-6-[3-(benzenesulfonamido)phenyl]-4-hydroxyhex-5-enyl]phenyl]propanoic acid,

(10) (S)-3-[2-[(E)-6-[3-(benzenesulfonamido)phenyl]-4-hydroxyhex-5-enyl]phenyl]propanoic acid,

(11) 3-[2-[(E)-5-[3-(benzenesulfonamido)phenyl]pent-4-enoxy]phenyl]propanoic acid,

(12) 3-[2-[5-[3-(benzenesulfonamido)phenyl]pentoxy]phenyl]propanoic acid,

(13) 3-[2-[(3S)-3-hydroxy-5-[3-[(1R)-1-hydroxy-2-phenylethyl]phenyl]pentoxy]phenyl]propanoic acid,

(14) 3-[2-[(3S)-3-hydroxy-5-[3-[(1S)-1-hydroxy-2-phenylethyl]phenyl]pentoxy]phenyl]propanoic acid,

(15) 3-[2-[2-[2-[3-(benzenesulfonamido)phenyl]ethoxy]ethoxy]phenyl]propanoic acid,

(16) 3-[2-[6-[3-(benzenesulfonamido)phenyl]-4-oxohexyl]phenyl]propanoic acid, or

(17) 3-[2-[5-[3-(benzenesulfonamido)phenyl]-3,3-difluoropentoxy]phenyl]propanoic acid, or a salt thereof;

[10] a pharmaceutical composition containing the compound represented by general formula (I) or the salt thereof according to claim 1;

[11] an agent for Schwann cell differentiation promotion containing the compound represented by general formula (I) or the salt thereof according to item [1];

[12] a prophylactic and/or therapeutic agent for neuropathy, containing the compound represented by general formula (I) or the salt thereof according to item [1];

[13] the agent according to item [12], wherein the neuropathy is peripheral neuropathy;

[14] the agent according to item [13], wherein the peripheral neuropathy is chronic inflammatory demyelinating polyneuropathy, Guillain-Barre syndrome, periarteritis nodosa, allergic vasculitis, diabetic peripheral neuropathy, entrapment neuropathy, peripheral neuropathy associated with the administration of a chemotherapeutic drug, or peripheral neuropathy associated with Charcot-Marie-Tooth disease;

[15] a method for preventing and/or treating neuropathy, including administering an effective amount of the compound represented by general formula (I) or the salt thereof according to item [1] to a mammal;

[16] the compound represented by general formula (I) or the salt thereof according to item [1], which is used for a prevention and/or treatment of neuropathy;

[17] a use of the compound represented by general formula (I) or the salt thereof according to item [1] for producing a prophylactic and/or therapeutic agent for neuropathy;

[18] a pharmaceutical composition for a protection and/or repair of a nerve, which contains the compound represented by general formula (I) or the salt thereof according to item [1];

[19] the pharmaceutical composition according to item [18], wherein the protection and/or repair of a nerve is the protection and/or repair of a nerve through a glial cell (e.g., a microglia, an astrocyte, an oligodendrocyte, an ependiomocyte, a Schwann cell, a satellite cell);

[20] the pharmaceutical composition according to item [19], wherein the protection and/or repair of a nerve through a glial cell is the protection and/or repair of a nerve by the promotion of the myelination of a Schwann cell; or the like.

Advantageous Effects of Invention

The compound of the present invention has a potent nerve-protecting and/or —repairing activity, and is therefore useful for the treatment of neuropathy such as peripheral neuropathy.

BRIEF DESCRIPTION OF DRAWING

The FIGURE shows nociceptive thresholds in streptozotocin models, which were obtained when each of the compounds of Examples 11, 36, 37 and 84 was administered at a dose amount of 0.3 mg/kg (the vertical axis represents a nociceptive threshold and the horizontal axis represents the number of days elapsed after the administration of streptozotocin).

DESCRIPTION OF EMBODIMENTS

Hereinbelow, the present invention will be described in detail.

The term "3- to 6-membered nitrogen-containing monocyclic saturated heterocyclic ring" as used herein refers to a monocyclic saturated heterocyclic ring containing at least one nitrogen atom, and examples thereof include aziridine, azetidine, pyrrolidine, imidazolidine, triazolidine, tetrazolidine, pyrazolidine, piperidine, piperazine, perhydropyrimidine, perhydropyridazine, tetrahydrooxazole(oxazolidine), tetrahydroisoxazole(isooxazolidine), tetrahydrothiazole(thiazolidine), tetrahydroisothiazole(isothiazolidine), tetrahydrofurazan, tetrahydrooxadiazole(oxadiazolidine), tetrahydrooxazine, tetrahydrooxadiazine, tetrahydrothiadiazole(thiadiazolidine), tetrahydrothiazine, tetrahydrothiadiazine, morpholine and thiomorpholine.

The term "halogen atom" as used herein refers to fluorine, chlorine, bromine, iodine or the like.

The term "C1-4 alkyl group" as used herein includes a linear or branched C1-4 alkyl group, and examples thereof include methyl, ethyl, propyl, butyl, isopropyl, isobutyl, sec-butyl and tert-butyl.

The term "C1-4 haloalkyl group" as used herein refers to a group having such a structure that a linear or branched C1-4 alkyl group is substituted by at least one halogen atom, and examples thereof include fluoromethyl, chloromethyl, bromomethyl, iodomethyl, difluoromethyl, trifluoromethyl, 1-fluoroethyl, 2-fluoroethyl, 2-chloroethyl, pentafluoroethyl, 1-fluoropropyl, 2-chloropropyl, 3-fluoropropyl, 3-chloropropyl, 4,4,4-trifluorobutyl and 4-bromobutyl.

The term "C1-6 alkylene group" as used herein includes a linear or branched C1-6 alkylene group, and examples thereof include methylene, ethylene, propylene, butylene, pentylene, hexanylene and isomers thereof.

The term "C2-6 alkenylene group" as used herein includes a linear or branched C2-6 alkenylene, and examples thereof include ethenylene, propenylene, butenylene, pentenylene, hexenylene and isomers thereof.

The term "C2-6 alkynylene group" as used herein includes a linear or branched C2-6 alkynylene group, and examples thereof include ethynylene, propynylene, butynylene, pentynylene, hexynylene and isomers thereof.

The term "linear C3-7 alkylene group" as used herein includes, for example, propylene, butylene, pentylene, hexanylene and heptanylene.

The term "linear C3-7 alkenylene group" as used herein includes, for example, propenylene, butenylene, pentenylene, hexenylene, heptenylene and isomers thereof.

The term "linear C3-7 alkynylene group" as used herein includes, for example, propynylene, butynylene, pentynylene, hexynylene and isomers thereof.

The term "C1-2 alkyl group" as used herein refers to methyl or ethyl.

The term "C3-5 saturated carbocyclic ring" as used herein includes, for example, cyclopropane, cyclobutane and cyclopentane.

The term "C5-10 monocyclic or bicyclic carbocyclic ring" as used herein includes, for example, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene and perhydronaphthalene.

The term "5- to 10-membered monocyclic or bicyclic heterocyclic ring" as used herein refers to a 5- to 10-membered monocyclic or bicyclic heterocyclic ring containing a hetero atom selected from an oxygen atom, a nitrogen atom and a sulfur atom, and examples thereof include pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzooxazole, benzothiazole, benzoimidazole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole(oxazolidine), dihydroisooxazole, tetrahydroisooxazole(isooxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzooxazole, perhydrobenzooxazole, dihydrobenzothiazole, perhydrobenzothiazole, dihydrobenzoimidazole, perhydrobenzoimidazole, dioxolane, dioxane, dithiolane, dithiane, dioxaindane, benzodioxane, chromane, benzodithiolane and benzodithiane.

The term "C1-4 alkoxy group" as used herein includes a linear or branched C1-4 alkoxy group, and examples thereof include methoxy, ethoxy, n-propoxy, isopropoxy, n-butoxy, isobutoxy, sec-butoxy and tert-butoxy.

The term "C1-4 haloalkoxy group" as used herein includes a group having such a structure that a linear or branched C1-4 alkoxy group is substituted by at least one halogen atom, and examples thereof include trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-bromopropoxy, 3-chloropropoxy, 2,3-dichloropropoxy, 1-fluorobutoxy, 4-fluorobutoxy and 1-chlorobutoxy.

The term "C3-6 monocyclic carbocyclic ring" as used herein includes, for example, cyclopropane, cyclobutane, cyclopentane, cyclohexane, cyclopentene, cyclohexene, cyclopentadiene, cyclohexadiene and benzene.

The term "3- to 6-membered monocyclic heterocyclic ring" as used herein refers to a 3- to 6-membered monocyclic heterocyclic ring containing a hetero atom selected from an oxygen atom, a nitrogen atom and a sulfur atom, and examples thereof include pyrrole, imidazole, triazole, tetrazole, pyrazole, pyridine, pyrazine, pyrimidine, pyridazine, furan, pyran, thiophene, thiopyran, oxazole, isooxazole, thiazole, isothiazole, furazan, oxadiazole, oxazine, oxadiazine, thiadiazole, thiazine, thiadiazine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, oxirane, oxetane, dihydrofuran, tetrahydrofuran, dihydropyran, tetrahydropyran, thiirane, thietane, dihydrothiophene, tetrahydrothiophene, dihydrothiopyran, tetrahydrothiopyran, dihydrooxazole, tetrahydrooxazole(oxazolidine), dihydroisooxazole, tetrahydroisoxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrothiadiazole, tetrahydrothiadiazole(thiadiazolidine), dihydrothiazine, tetrahydrothiazine, dihydrothiadiazine, tetrahydrothiadiazine, morpholine, thiomorpholine, oxathiane, dioxolane, dioxane, dithiolane and dithiane.

The term "5- to 6-membered monocyclic heterocyclic ring" as used herein refers to a 5- to 6-membered monocyclic heterocyclic ring containing a hetero atom selected from an oxygen atom, a nitrogen atom and a sulfur atom, and examples thereof include pyrrole, imidazole, triazole, tetrazole, pyrazole, pyridine, pyrazine, pyrimidine, pyridazine, furan, pyran, thiophene, thiopyran, oxazole, isooxazole, thiazole, isothiazole, furazan, oxadiazole, oxazine, oxadiazine, thiadiazole, thiazine, thiadiazine, pyrroline, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisooxazole, tetrahydroisoxazole (isooxazolidine), dihydrothiazole, tetrahydrothiazole(thiazolidine), dihydroisothiazole, tetrahydroisothiazole (isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrothiadiazole, tetrahydrothiadiazole(thiadiazolidine), dihydrothiazine, tetrahydrothiazine, dihydrothiadiazine, tetrahydrothiadiazine, morpholine, thiomorpholine, oxathiane, dioxolane, dioxane, dithiolane and dithiane.

The term "5- to 6-membered monocyclic aromatic heterocyclic ring" as used herein refers to a 5- to 6-membered monocyclic aromatic heterocyclic ring containing a hetero atom selected from an oxygen atom, a nitrogen atom and a sulfur atom, and examples thereof include pyrrole, imidazole, triazole, tetrazole, pyrazole, pyridine, pyrazine, pyrimidine, pyridazine, furan, thiophene, oxazole, isooxazole, thiazole, isothiazole, furazan, oxadiazole and thiadiazole.

The term "C1-3 alkylene group" as used herein includes a linear or branched C1-3 alkylene group, and examples thereof include methylene, ethylene, propylene and isomers thereof.

The term "C1-6 alkyl group" as used herein includes a linear or branched C1-6 alkyl group, and examples thereof include methyl, ethyl, n-propyl, isopropyl, n-butyl, isobutyl, sec-butyl, tert-butyl, pentyl, hexyl and isomers thereof.

The term "C2-6 alkenyl group" as used herein includes a linear or branched C2-6 alkenyl group, and examples thereof include ethenyl, propenyl, butenyl, pentenyl, hexenyl and isomers thereof.

The term "C2-6 alkynyl group" as used herein refers to a linear or branched C2-6 alkynyl group, and examples thereof include ethynyl, propynyl, butynyl, pentynyl, hexynyl and isomers thereof.

The term "C1-6 haloalkyl group" as used herein refers to a group having such a structure that a linear or branched C1-6 alkyl group is substituted by at least one halogen atom, and examples thereof include fluoromethyl, chloromethyl, bromomethyl, iodomethyl, difluoromethyl, trifluoromethyl, 1-fluoroethyl, 2-fluoroethyl, 2-chloroethyl, pentafluoroethyl, 1-fluoropropyl, 2-chloropropyl, 3-fluoropropyl, 3-chloropropyl, 4,4,4-trifluorobutyl, 4-bromobutyl, 1-fluoropentane and 2-chlorohexane.

The term "C2-6 haloalkenyl group" as used herein refers to a group having such a structure that a linear or branched C2-6 alkenyl group is substituted by at least one halogen atom, and examples thereof include 1-fluoroethenyl, 2-fluoroethenyl, 2-chloroethenyl, pentafluoroethenyl, 1-fluoropropenyl, 2-chloropropenyl, 3-fluoropropenyl, 3-chloropropenyl, 4,4,4-trifluorobutenyl, 4-bromobutenyl, 1-fluoropentenyl and 2-chlorohexenyl.

The term "C2-6 haloalkynyl group" as used herein refers to a group having such a structure that a linear or branched C2-6 alkynyl group is substituted by at least one halogen atom, and examples thereof include 1-fluoroethynyl, 2-fluoroethynyl, 2-chloroethynyl, pentafluoroethynyl, 1-fluoropropynyl, 2-chloropropynyl, 3-fluoropropynyl, 3-chloropropynyl, 4,4,4-trifluorobutynyl, 4-bromobutynyl, 1-fluoropentynyl and 2-chlorohexynyl.

The term "C1-6 alkoxy group" as used herein includes a linear or branched C1-6 alkoxy group, and examples thereof include methoxy, ethoxy, propoxy, isopropoxy, butoxy, isobutoxy, tert-butoxy, n-pentoxy, isopentoxy, neopentoxy, n-hexyloxy and isohexyloxy.

The term "C1-6 haloalkoxy group" as used herein refers to a group having such a structure that a linear or branched C1-6 alkoxy group is substituted by at least one halogen atom, and examples thereof include trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-bromopropoxy, 3-chloropropoxy, 2,3-dichloropropoxy, 1-fluorobutoxy, 4-fluorobutoxy, 1-chlorobutoxy, 2-fluoropentoxy and 3-chlorohexyloxy.

The term "linear C2-6 alkylene group" as used herein includes, for example, ethylene, propylene, butylene, pentylene and hexanylene.

The term "linear C3-7 alkylene group" as used herein includes, for example, propylene, butylene, pentylene, hexanylene and heptanylene.

The term "linear C1-3 alkylene group" as used herein includes, for example, methylene, ethylene and propylene.

The term "C5-6 monocyclic carbocyclic ring" as used herein includes, for example, cyclopentane, cyclohexane, cyclopentene, cyclohexene, cyclopentadiene, cyclohexadiene and benzene.

The term "C2-4 alkylene group" as used herein includes a linear or branched C2-4 alkylene group, and examples thereof include ethylene, propylene, butylene and isomers thereof.

The term "C3-4 alkylene group" as used herein includes a linear or branched C3-4 alkylene group, and examples thereof include propylene, butylene and isomers thereof.

In the present invention,
[Formula 8]

- - - - - - refers to a single bond, a double bond or a triple bond. In the case where the symbol represents a double bond, the double bond includes a cis-form and a trans-form thereof.

In the present invention, the direction of the bonding of $L^3$ is not limited. For example, in the case where $L^3$ represents $—NR^{202}—S(O)_2—$, $L^2$ may be $—R^{31}—NR^{202}—S(O)_2—R^{32}$ or $—R^{31}—S(O)_2—NR^{202}—R^{32}$.

In the present invention, each of the alkyl, alkenyl, alkynyl, alkylene, alkenylene, alkynylene and alkoxy groups includes both of a linear form and a branched form thereof, unless otherwise stated.

In the present invention, in the case where $R^3$ represents a methylidene group, it is meant that the formula:

[Formula 9]

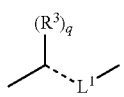

[wherein all symbols have the same meanings as mentioned above] which is a partial structure of general formula (I) has a structure shown below:

[Formula 10]

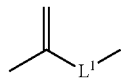

The compound of the present invention is a compound represented by general formula (I) wherein the number of atoms located between CycA and the benzene ring is 5 or more, or a salt thereof.

[Formula 11]

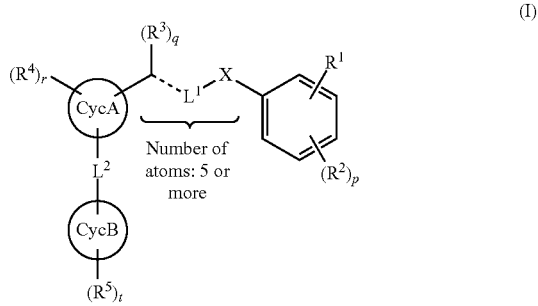

In the present invention, $R^1$ is preferably $—R^{11}—COOR^{12}$, more preferably $—R^{11}—COOH$. $R^{11}$ is preferably a C1-6 alkylene group which may be substituted by 1to 3 halogen atoms, more preferably a C2-4 alkylene group which may be substituted by 1 to 3 halogen atoms.

In the present invention, in the case where $R^1$ represents the group:

[Formula 12]

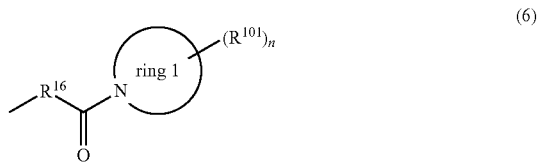

ring 1 is more preferably a 6-membered nitrogen-containing monocyclic saturated heterocyclic ring, still more preferably morpholine.

In the present invention, $R^{101}$ is preferably a hydrogen atom.

In the present invention, each of $R^{11}$, $R^{13}$, $R^{16}$, $R^{17}$, $R^{18}$ and $R^{20}$ is preferably a C1-6 alkylene group which may be substituted by 1 to 3 halogen atoms, more preferably a C2-4 alkylene group which may be substituted by 1 to 3 halogen atoms.

In the present invention, each of $R^{12}$, $R^{14}$, $R^{15}$ and $R^{19}$ is preferably a hydrogen atom.

In the present invention, $R^2$ is preferably a halogen atom or a C1-4 alkyl group.

In the present invention, X is preferably an oxygen atom.

In the present invention, $L^1$ is preferably (1) a linear C3-7 alkylene group which may be substituted by 1 to 4 $R^{L1a}$s or (2) (a linear C1-3 alkylene group which may be substituted by 1 to 2 $R^{L1a}$s)-O-(a linear C1-3 alkylene group which may be substituted by 1 to 2 $R^{L1a}$s), more preferably a linear C3-7 alkylene group which may be substituted by 1 to 4 $R^{L1a}$s.

In the present invention,

[Formula 13]

is preferably a single bond or a double bond.

In the present invention,

[Formula 14]

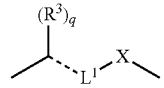

is preferably (1)=CH-(a linear C2-6 alkylene group which may be substituted by 1 to 3 $R^{L1a}$s)-, (2) -(a linear C3-7 alkylene group which may be substituted by 1 to 3 $R^{L1a}$s)- or (3) -(a linear C1-3 alkylene group which may be substituted by 1 to 2 $R^{L1a}$s)-O-(a linear C1-3 alkylene group which may be substituted by 1 to 2 $R^{L1a}$s)-(in (1) to (3), $R^{L1a}$ has the same meaning as mentioned above), more preferably (1)=CH-(a linear C2-6 alkylene group which may be substituted by 1 to 3 $R^{L1a}$s)- or (2) -(a linear C3-7 alkylene group which may be substituted by 1 to 3 $R^{L1a}$s)-(in (1) to (2), $R^{L1a}$ has the same meaning as mentioned above), still more preferably (1)=CH-(a linear C3 alkylene group which may be substituted by 1 to 3 $R^{L1a}$s)- or (2) -(a linear C4 alkylene group which may be substituted by 1 to 3 $R^{L1a}$s)-(in (1) to (2), $R^{L1a}$ has the same meaning as mentioned above).

In the present invention, $R^{L1a}$ is preferably a hydroxyl group, a halogen atom or an oxo group, more preferably a hydroxyl group.

In the present invention, $R^3$ is preferably a hydrogen atom.

In the present invention, CycA is preferably (1) a C5-6 monocyclic carbocyclic ring or (2) a 5- to 10-membered monocyclic or bicyclic heterocyclic ring, still more preferably benzene or a 5- to 6-membered monocyclic aromatic heterocyclic ring.

In the present invention, CycA is preferably benzene, cyclohexane, pyridine, thiazole, isoindoline or tetrahydroquinoline, more preferably benzene, isoindoline or tetrahydroquinoline, still more preferably benzene.

In the present invention, $R^4$ is preferably a halogen atom, a C1-4 alkyl group or a C1-4 haloalkyl group, more preferably a halogen atom, a methyl group or a trihalomethyl group.

In the present invention, $L^3$ is preferably —$NR^{201}$—S(O)$_2$— or —$CR^{204}$(OH).

In the present invention, $L^2$ is preferably —$NR^{201}$—S(O)$_2$— or —$CR^{204}$(OH)—CH$_2$—.

In the present invention, each of $R^{201}$, $R^{202}$, $R^{203}$, $R^{204}$ and $R^{205}$ is preferably a hydrogen atom, a C1-4 alkyl group, a C1-4 alkyl group which is substituted by a hydroxyl group, a C1-4 alkyl group which is substituted by a C3-6 monocyclic carbocyclic ring, or a C1-4 alkyl group which is substituted by a 3- to 6-membered monocyclic heterocyclic ring, more preferably a hydrogen atom. The C1-4 alkyl group which is substituted by a C3-6 monocyclic carbocyclic ring is preferably a C1-4 alkyl group which is substituted by cyclopropane or benzene, and the C1-4 alkyl group which is substituted by a 3- to 6-membered monocyclic heterocyclic ring is preferably a C1-4 alkyl group which is substituted by oxetane, tetrahydrofuran or tetrahydropyran.

In the present invention, $R^{31}$ is preferably a bond or a C1-3 alkylene group, more preferably a bond.

In the present invention, $R^{32}$ is preferably a bond or a C1-3 alkylene group, more preferably a C1-3 alkylene group.

In the present invention, CycB is preferably (1) a C5-6 monocyclic carbocyclic ring or (2) a 5- to 6-membered monocyclic heterocyclic ring, more preferably benzene or a 5 to 6-membered monocyclic aromatic heterocyclic ring.

In the present invention, CycB is preferably cyclopentane, benzene, cyclohexane, thiophene, pyridine or benzofuran, more preferably benzene.

In the present invention, $R^5$ is preferably a halogen atom, a C1-4 alkyl group, a C1-4 haloalkyl group or a C1-4 alkoxy group, more preferably a halogen atom, a C1-4 alkoxy group, a trohalomethyl group or a C1-4 alkoxy group.

In the present invention, each of r and t is preferably an integer of 0 to 3, more preferably an integer of 0 to 2.

In the present invention, the structure of the group:

[Formula 15]

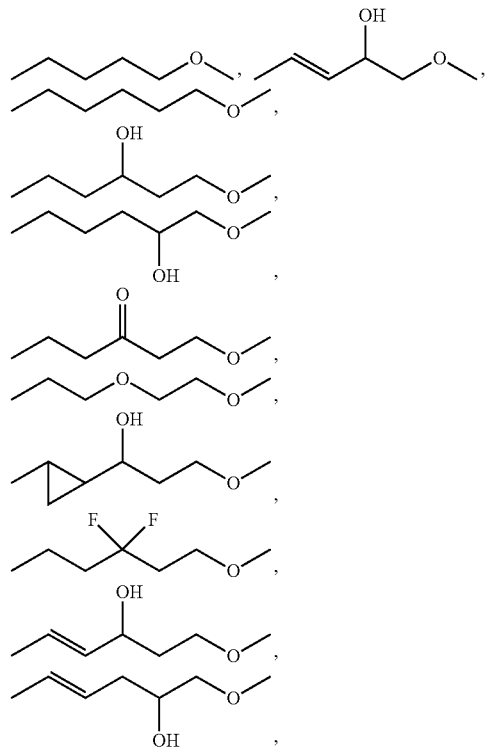

[wherein all symbols have the same meanings as mentioned above] which is a partial structure of general formula (I) is preferably

[Formula 16]

-continued

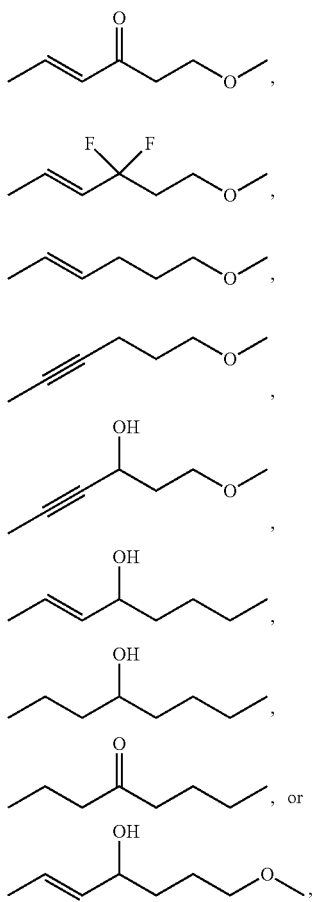

more preferably

[Formula 17]

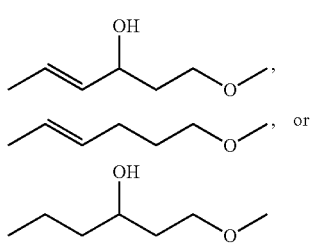

In the present invention, the structure of the formula:

[Formula 18]

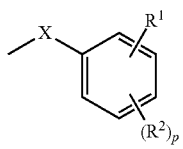

[wherein all symbols have the same meanings as mentioned above] which is a partial structure of general formula (I) is preferably

[Formula 19]

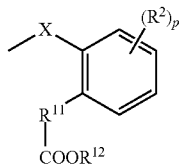

[wherein all symbols have the same meanings as mentioned above].

In the present invention, the structure of the formula:

[Formula 20]

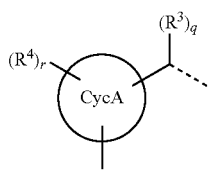

[wherein all symbols have the same meanings as mentioned above] which is a partial structure of general formula (I) is preferably

[Formula 21]

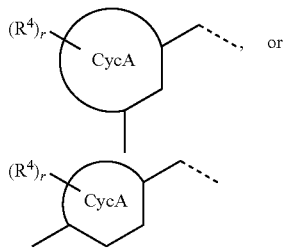

[wherein all symbols have the same meanings as mentioned above].

In the present invention, one embodiment of general formula (I) is general formula (I-i):

[Formula 22]

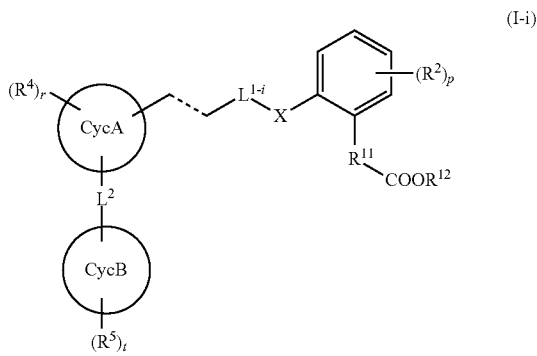

[wherein $L^{1-i}$ represents (1) a linear C2-4 alkylene group which may be substituted by 1 to 3 $R^{L1a}$s or (2) —O-(a linear C1-3 alkylene group which may be substituted by 1 to 2 $R^{L1a}$s)-; and other symbols have the same meanings as mentioned above].

In the present invention, one embodiment of general formula (I-i) is general formula (I-ii):

[Formula 23]

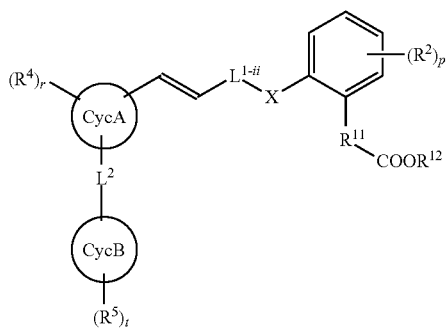

(I-ii)

[wherein $L_{1\text{-}ii}$ represents a linear C2-4 alkylene group which may be substituted by 1 to 3 $R^{L1a}$s; and other symbols have the same meaning as mentioned above]; general formula (I-iii):

[Formula 24]

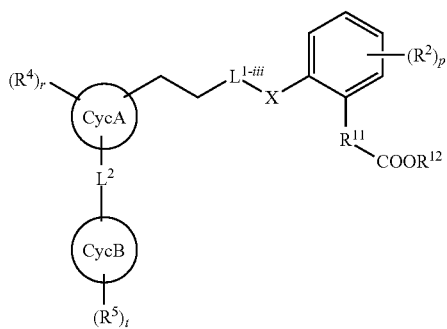

(I-iii)

[wherein $L^{1\text{-}iii}$ represents (1) a linear C2-4 alkylene group which may be substituted by 1 to 3 $R^{L1a}$s or (2) —O-(a linear C1-3 alkylene group which may be substituted by 1 to 2 $R^{L1a}$s)-; and other symbols have the same meanings as mentioned above]; or general formula (I-iv):

[Formula 25]

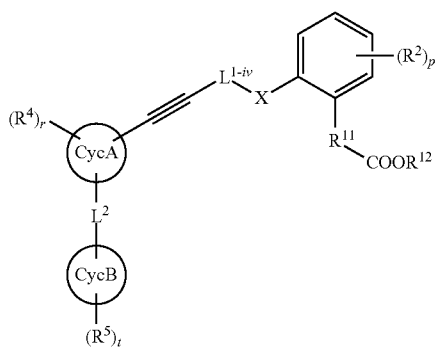

(I-iv)

[wherein $L^{1\text{-}iv}$ represents a linear C2-4 alkylene group which may be substituted by 1 to 3 $R^{L1a}$s; and other symbols have the same meanings as mentioned above].

One embodiment of the compound represented by general formula (I-i), (I-ii), (I-iii) or (I-iv) or a salt thereof is a compound in which:

(1) $R^{11}$ represents a C2-4 alkylene group;

(2) X represents an oxygen atom;

(3) $R^{L1a}$ represents a hydroxyl group;

(4) CycA represents (i) a C5-6 monocyclic carbocyclic ring, or a 5- to 10-membered monocyclic or bicyclic heterocyclic ring, (ii) benzene or a 5 to 6-membered monocyclic aromatic heterocyclic ring, (iii) a C5-6 monocyclic carbocyclic ring, or (iv) benzene, cyclohexane, pyridine, thiazole, isoindoline or tetrahydroquinoline;

(5) CycB represents (i) a C5-6 monocyclic carbocyclic ring or a 5 to 6-membered monocyclic heterocyclic ring, (ii) benzene or a 5 to 6-membered monocyclic aromatic heterocyclic ring, (iii) a C5-6 monocyclic carbocyclic ring, or (iv) cyclopentane, benzene, cyclohexane, thiophene, pyridine or benzofuran;

(6) $L^2$ represents —$NR^{201}$—$S(O)_2$— or —$CR^{204}(OH)$—$CH_2$—; or (7) symbols other than $R^{11}$, X, $R^{L1a}$, CycA, CycB and $L^2$ represent the above-mentioned groups (e.g., the groups which are mentioned above as the "preferred", "more preferred" or "still more preferred" groups); or (8) a combination of two or more of the items (1) to (7) is satisfied, or a salt of the compound.

In the present invention, the compound represented by general formula (I-i), (I-ii), (I-iii) or (I-iv) or a salt thereof is preferably:

(1) a compound wherein X represents an oxygen atom and $L^2$ represents —$NR^{201}$—$S(O)_2$— or —$CR^{204}(OH)$—$CH_2$—, or a salt thereof, (2) a compound wherein X represents an oxygen atom, $L^2$ represents —$NR^{201}$—$S(O)_2$— or —$CR^{204}(OH)$—$CH_2$—, and each of CycA and CycB represents a C5-6 monocyclic carbocyclic ring, or a salt thereof;

(3) a compound wherein $R^{11}$ represents a C2-4 alkylene group, X represents an oxygen atom, $L^2$ represents —$NR^{201}$—$S(O)_2$— or —$CR^{204}(OH)$—$CH_2$—, and each of CycA and CycB represents a C5-6 monocyclic carbocyclic ring, or a salt thereof; or (4) a compound wherein X represents an oxygen atom, $R^{L1a}$ represents a hydroxyl group, $L^2$ represents —$NR^{201}$—$S(O)_2$— or —$CR^{204}(OH)$—$CH_2$—, and each of CycA and CycB represents a C5-6 monocyclic carbocyclic ring, or a salt of the compound.

In the present invention, another embodiment of general formula (I) is general formula (I-1):

[Formula 26]

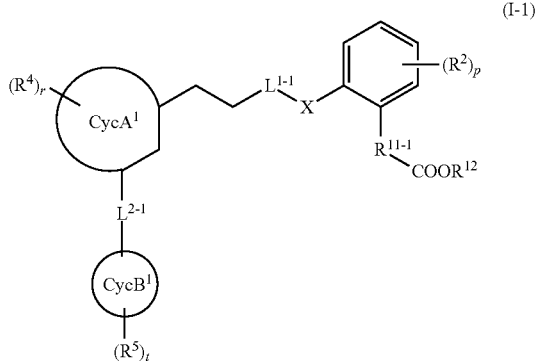

(I-1)

[wherein all symbols have the same meanings as mentioned above].

In the present invention, general formula (I-1) is preferably general formula (I-1-A):

[Formula 27]

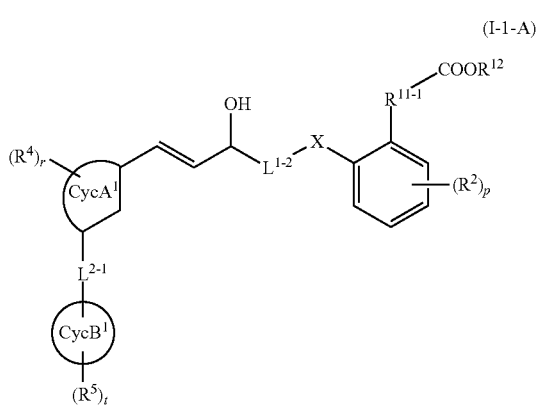

(I-1-A)

[wherein $L^{1-2}$ represents a linear C2-3 alkylene group; and other symbols have the same meaning as mentioned above];

general formula (I-1-B):

[Formula 28]

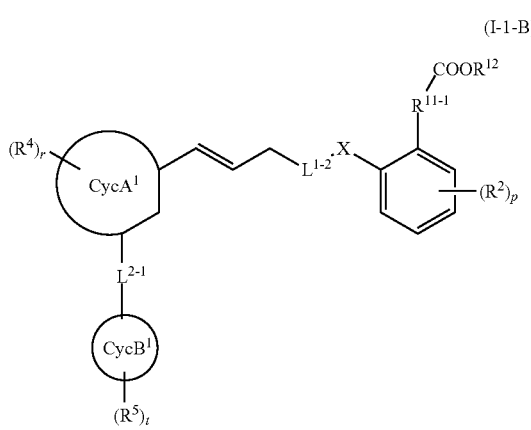

(I-1-B)

[wherein all symbols have the same meanings as mentioned above];

general formula (I-1-C):

[Formula 29]

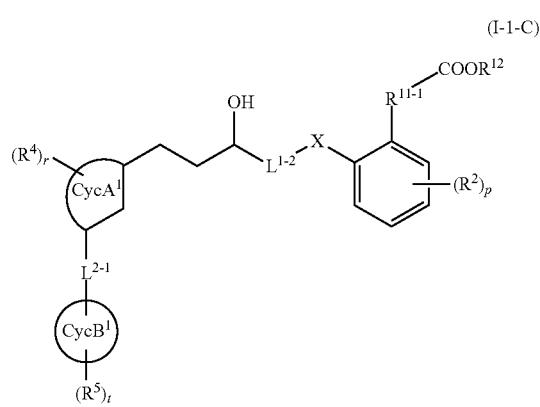

(I-1-C)

[wherein all symbols have the same meanings as mentioned above];

general formula (I-1-D):

[Formula 30]

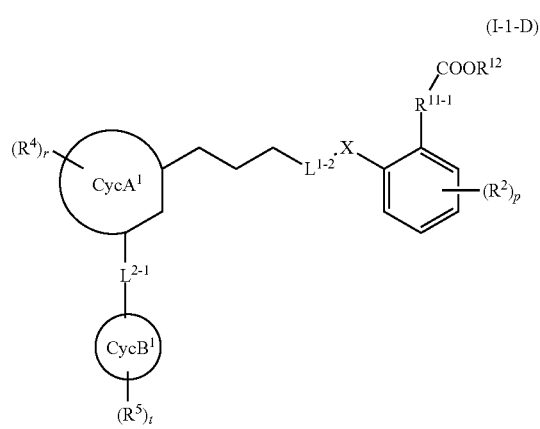

(I-1-D)

[wherein all symbols have the same meanings as mentioned above].

Embodiments of the compound represented by general formula (I-1-A), (I-1-B), (I-1-C) or (I-1-D) or a salt thereof include:

(1) a compound wherein X represents an oxygen atom, or a salt thereof;

(2) a compound wherein $CycA^1$ represents benzene, cyclohexane, pyridine, thiazole, isoindoline or tetrahydroquinoline, or a salt thereof, (3) a compound wherein $CycB^1$ represents cyclopentane, benzene, cyclohexane, thiophene, pyridine or benzofuran, or a salt thereof;

(4) a compound wherein groups other than X, $CycA^1$ and $CycB^1$ represent the above-mentioned groups (e.g., the groups which are mentioned above as the "preferred", "more preferred" or "still more preferred" groups), or a salt thereof, and (5) a compound wherein a combination of two or more of the items (1) to (4) is satisfied, or a salt thereof.

[Isomers]

In the present invention, as is apparent to persons skilled in the art, the symbol:
[Formula 31]

means that the bond projects behind the plane of the paper (i.e., an α-configuration), the symbol:
[Formula 32]

means that the bond projects out of the plane of the paper (i.e., a β-configuration), and the symbol:
[Formula 33]

means that the bond is a mixture of the α-configuration and the β-configuration at an arbitrary mixing ratio, unless otherwise stated.

In the present invention, the isomer includes all of these isomers, unless otherwise specified. For example, each of alkyl, alkenyl, alkynyl, alkoxy, alkylthio, alkylene, alkenylene, alkynylene, alkylidene and alkenylidene includes both of a linear form and a branched form thereof. In addition, an isomer in a double bond, a ring or a condensed ring (an E-, Z—, cis- or trans-form), an isomer due to the presence of an asymmetric carbon or the like (an R- or S-form, an α- or β-configuration, an enantiomer, a diastereomer), an optically active form having an optical activity (a D-, L-, d- or l-form), a polar body (a highly polar body, a poorly polar body) obtained by chromatographic separation, an equilibrium compound and a rotational isomer, and a mixture and a racemic mixture thereof at an arbitrary mixing ratio are also included within the scope of the present invention.

The optically active compound in the present invention may include a 100%-pure form thereof as well as other optical isomers each having purity of less than 50%.

In the present invention, all of the statements about the compound of the present invention cover those about a compound represented by general formula (I), or a salt, N-oxide, solvate or cocrystal thereof, or an N-oxide, solvate or cocrystal of a salt of the compound represented by general formula (I).

The compound represented by general formula (I) can be converted to a corresponding salt by a known method. The salt is preferably water-soluble. The salt is also preferably a pharmaceutically acceptable salt. Examples of the salt include a salt of an alkali metal (e.g., lithium, potassium, sodium), a salt of an alkaline earth metal (e.g., calcium, magnesium), a salt of other metal (e.g., silver, zinc), an ammonium salt, a salt of a pharmaceutically acceptable organic amine (e.g., tetramethylammonium, choline, triethylamine, methylamine, dimethylamine, ethylamine, diethylamine, cyclopentylamine, benzylamine, phenethylamine, tert-butylamine, ethylenediamine, piperidine, piperazine, monoethanolamine, diethanolamine, tris(hydroxymethyl)aminomethane, N-benzyl-2-phenethylamine, deanol, 2-(diethylamino)ethanol, 1-(2-hydroxyethyl)pyrrolidine, lysine, arginine, N-methyl-D-glucamine), an acid addition salt (e.g., an inorganic acid salt (a hydrochloric acid salt, a hydrobromic acid salt, a hydroiodic acid salt, a sulfuric acid salt, a phosphoric acid salt, a nitric acid salt, etc.), an organic acid salt (an acetic acid salt, a trifluoroacetic acid salt, a lactic acid salt, a tartaric acid salt, an oxalic acid salt, a fumaric acid salt, a maleic acid salt, a benzoic acid salt, a citric acid salt, a methanesulfonic acid salt, an ethanesulfonic acid salt, a benzenesulfonic acid salt, a toluenesulfonic acid salt, an isethionic acid salt, a napadisilic acid salt, a glucuronic acid salt, a gluconic acid salt, etc.)) and the like.

The compound represented by general formula (I) or a pharmaceutically acceptable salt thereof may be present in a non-solvated form or a form solvated with a pharmaceutically acceptable solvent such was water and ethanol. The solvate is preferably low-toxic and water-soluble, and is more preferably a hydrate. The compound represented by general formula (I) or the salt thereof can be converted to a solvate by a known method.

An N-oxide form of the compound represented by general formula (I) is a compound produced by oxidizing a nitrogen atom in the compound represented by general formula (I). The N-oxide form of the compound represented by general formula (I) may be in the form of the above-mentioned alkaline (earth) metal salt, ammonium salt, organic amine salt or acid addition salt.

The compound represented by general formula (I) or a pharmaceutically acceptable salt thereof may be present in the form of a cocrystal with a proper cocrystal forming agent. The cocrystal is preferably a pharmaceutically acceptable one that is formed with a pharmaceutically acceptable cocrystal forming agent. A cocrystal is typically defined as a crystal formed by at least two types of different intermolecular interactions. The cocrystal may be a complex of a neutral molecule and a salt. The cocrystal can be prepared by a known method, such as melt-crystallization, recrystallization from a solvent, and physical grinding of all of components together. Examples of the proper cocrystal forming agent include: an organic acid (e.g., malic acid, succinic acid, adipic acid, gluconic acid, tartaric acid, benzoic acid, 4-hydroxybenzoic acid, 3-hydroxybenzoic acid, nicotinic acid, isonicotinic acid); an organic amine (e.g., imidazole, diethanolamine, triethanolamine, tris(hydroxymethyl)aminomethane, N-benzyl-phenethylamine, deanol, 2-(diethylamino)ethanol, 1-(2-hydroxyethyl)pyrrolidine, 4-(2-hydroxyethyl)morpholine, N-methyl-D-glucamine, glycine, histidine, proline); and other organic compounds (e.g., caffeine, saccharin).

The term "prodrug of the compound represented by general formula (I)" refers to a compound which can be converted to a compound represented by general formula (I) through a reaction with an enzyme, gastric acid or the like in vivo. Examples of the prodrug of the compound represented by general formula (I) include: in the case where the compound represented by general formula (I) has an amino group, a compound having such a structure that the amino group in the corresponding compound is acylated, alkylated or phosphorylated (e.g., a compound having such a structure that the amino group i the corresponding compound represented by general formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated or tert-butylated); in the case where the compound represented by general formula (I) has a hydroxyl group, a compound having such a structure that the hydroxyl group in the corresponding compound is acylated, alkylated, phosphorylated or borated (e.g., a compound having such a structure that the hydroxyl group in the corresponding compound represented by general formula (I) is acetylated, palmitoylated, propanoylated, pivaloylated, succinylated, fumarylated, alanylated or dimethylaminomethylcarbonylated); and in the case where the compound represented by general formula (I) has a carboxyl group, a compound having such a structure that the carboxyl group in the corresponding compound is esterified or amidated (e.g., a compound having such a structure that the carbonyl group in the corresponding compound represented by general formula (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified or methyladmidated). These compounds can be produced by known methods. The prodrug of the compound represented by general formula (I) may be a solvate. Alternatively, the prodrug of the compound represented by general formula (I) may be a compound which can change into a compound represented by general formula (I) under physiological conditions as mentioned in "Development of Pharmaceuticals", vol. 7, "Design of Molecules", pages: 163-198, 1990, Hirokawa-Shoten Ltd. Furthermore, the compound represented by general formula (I) may be labeled with an isotope (e.g., $^2$H, $^3$H $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I, $^{125}$I) or the like.

[Method for Producing the Compound of the Present Invention]

The compound of the present invention can be produced by an appropriately modified method of a known method, such as the method mentioned in Comprehensive Organic Transformations: A Guide to Functional Group Preparations, 2nd Edition (Richard C. Larock, John Wiley & Sons Inc, 1999) and the methods mentioned in the section "EXAMPLES" or by a combination of these methods.

Among the compounds represented by general formula (I), a compound represented by general formula (I-A):

[Formula 34]

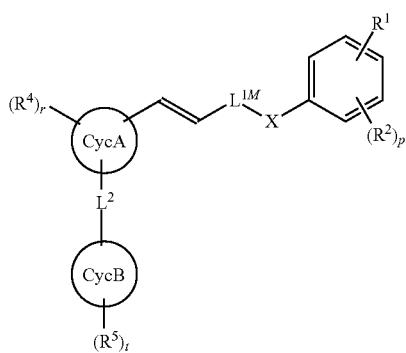

(I-A)

(wherein $L^{1M}$ represents (1) a linear C2-6 alkylene group which may be substituted by 1 to 4 $R^{L1a}$s, (2) a linear C2-6 alkenylene group which may be substituted by 1 to 4 $R^{L1a}$s, (3) a linear C2-6 alkynylene group which may be substituted by 1 to 4 $R^{L1a}$s, or (4) (a linear C1-3 alkynylene group which may be substituted by 1 to 2 $R^{L1a}$s)-O-(a linear C1-3 alkylene group which may be substituted by 1 to 2 $R^{L1a}$s); and other symbols have the same meanings as mentioned above) can be produced by the method shown in the following reaction scheme 1.

Reaction Scheme 1

[Formula 35]

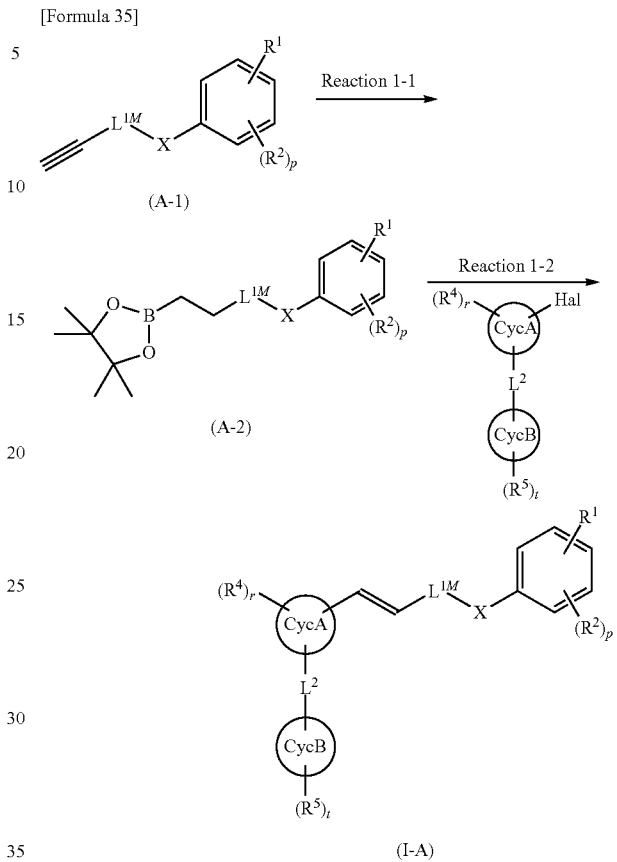

(wherein Hal represents a halogen atom; and other symbols have the same meanings as mentioned above.)

In reaction scheme 1, the reaction 1-1 can be achieved by carrying out a nucleophilic addition reaction using a compound represented by general formula (A-1) and 4,4,5,5-tetramethyl-1,3,2-dioxaborolane. The nucleophilic addition reaction is known, and can be carried out, for example, in an organic solvent (e.g., hexane, heptane, octane, benzene, toluene, tetrahydrofuran (abbreviated as "THF", hereinafter), dioxane, dimethoxyethane, diethyl ether, or a mixed solvent composed of two or more of these solvents) or under solvent-free conditions at a temperature of 0 to 120° C. The reaction may also be carried out in the presence of a catalyst for the purpose of accelerating the reaction. Examples of the catalyst include formic acid, acetic acid, benzoic acid, 4-dimethylaminobenzoic acid and Schwartz's reagent (CAS Registry Number: 37342-97-5).

In reaction scheme 1, the reaction 1-2 can be achieved by carrying out a Suzuki Coupling reaction using a compound represented by general formula (A-2) and a compound represented by general formula (A-3). The Suzuki coupling reaction is known, and can be carried out, for example, in an organic solvent (e.g., toluene, benzene, N,N-dimethylformamide (abbreviated as "DMF", hereinafter), THF, methanol, ethanol, acetonitrile, dimethoxyethane, acetone, dioxane, dimethylacetamide), water, a mixed solvent composed of two or more of these solvents or the like, in the presence of a palladium catalyst (e.g., tetrakis(triphenylphosphine)palladium (Pd(PPh$_3$)$_4$), dichlorobis(triphenylphosphine)palladium (Cl$_2$Pd(PPh$_3$)$_2$), palladium acetate (Pd(OAc)$_2$), bis(tritert-butylphosphine)palladium(O) (Pd(tBu3P)$_2$)) and in the presence of a base (e.g., sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide, tetrabutylammonium fluoride) at room temperature to 120° C.

Furthermore, a compound represented by general formula (I-B):

[Formula 36]

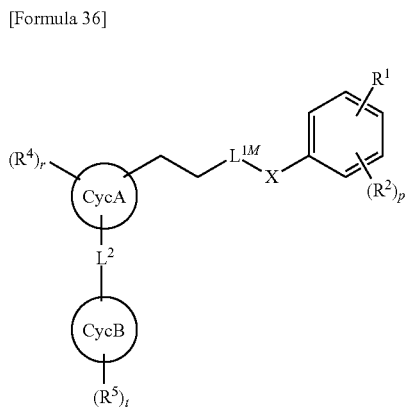

(wherein all symbols have the same meanings as mentioned above) can be produced by carrying out a reduction reaction using a compound represented by general formula (I-A). The reduction reaction is known, and can be carried out by the following methods. For example, (1) a reduction reaction using a metal and (2) a diimide reduction reaction are mentioned. The reduction reaction using a metal (1) can be carried out, for example, in an organic solvent (e.g., THF, dioxane, dimethoxyethane, diethyl ether, methanol, ethanol, benzene, toluene, acetone, methyl ethyl ketone, acetonitrile, DMF, ethyl acetate, acetic acid, water, or a mixed solvent composed of two or more of these solvents) in the presence or absence of a hydrogenation catalyst (e.g., palladium-carbon, palladium black, palladium, palladium hydroxide, platinum dioxide, platinum-carbon, nickel, raney nickel, ruthenium chloride) in the presence or absence of an acid (e.g., hydrochloric acid, sulfuric acid, hypochlorous acid, boric acid, tetrafluoroboric acid, acetic acid, p-toluenesulfonic acid, oxalic acid, trifluoroacetic acid (abbreviated as "TFA", hereinafter), formic acid) under a hydrogen atmosphere under ambient pressure or under pressure at 0 to 200° C. The diimide reduction reaction (2) can be carried out, for example, in an organic solvent (e.g., toluene, benzene, DMF, THF, acetonitrile, dimethoxyethane, acetone, dioxane, dimethylacetamide, methanol, ethanol, a mixed solvent composed of two or more of these solvents) in the presence or absence of a hydrazine compound (e.g., hydrazine, hydrazine monohydrate, tosylhydrazine) and a base (e.g., sodium hydroxide, potassium hydroxide, sodium carbonate, sodium bicarbonate, potassium carbonate, cesium carbonate) at 0 to 120° C.

Among the compounds represented by general formula (I), a compound represented by general formula (I-C):

[Formula 37]

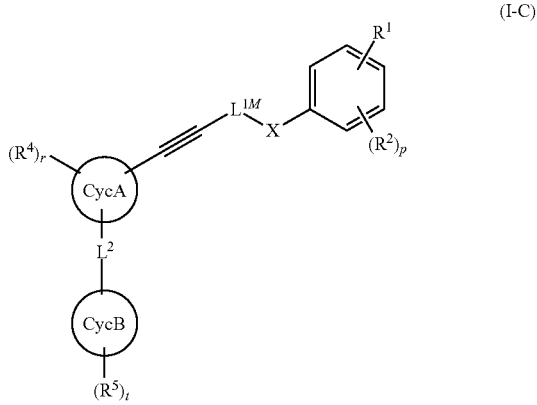

(wherein all symbols have the same meanings as mentioned above) can be produced by the method shown in reaction scheme 2 below.

Reaction Scheme 2

[Formula 38]

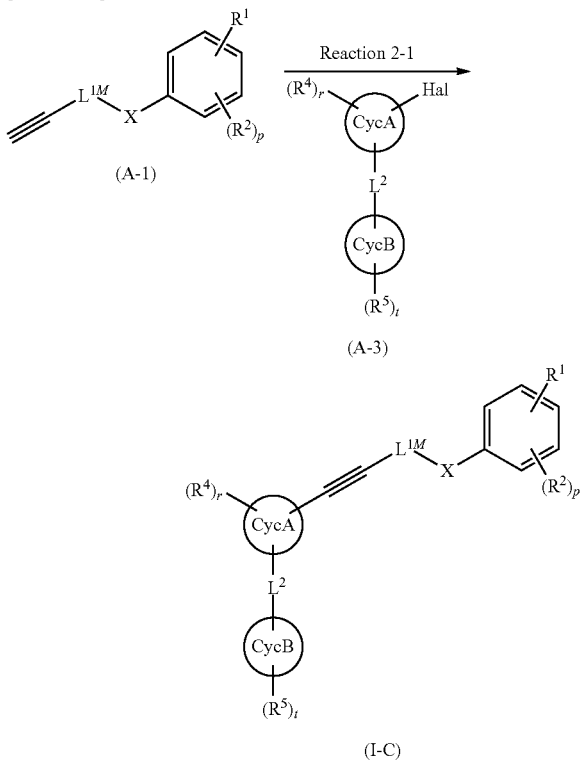

(wherein all symbols have the same meanings as mentioned above).

In reaction scheme 2, the reaction 2-1 can be achieved by subjecting a compound represented by general formula (A-1) and a compound represented by general formula (A-3) to a Sonogashira reaction. The Sonogashira reaction is known, and can be achieved by, for example, carrying out the reaction in an organic solvent (e.g., ethyl acetate, isopropyl acetate, benzene, toluene, xylene, heptane, cyclohexane, THF, dioxane, dimethoxyethane, ethanol, 2-propanol, polyethylene glycol, dimethylsulfoxide, DMF, N,N-dimethylacetamide, N-methyl-2-pyrrolidinone, methylene chloride, chloroform, acetone, acetonitrile), water, a mixed solvent composed of two or more of these solvents or the like or under solvent-free conditions, in the presence of a base (e.g., diethylamine, triethylamine, propylamine, diisopropylamine, diisopropylethylamine, dibutylamine, tributylamine, pyrrolidine, piperidine, N-methylpiperidine, 1,4-diazabicyclo[2.2.2]octane, pyridine, sodium hydroxide, sodium bicarbonate, sodium carbonate, potassium carbonate, cesium carbonate, sodium phosphate, potassium phosphate, potassium fluoride), in the presence of a catalyst (e.g., a palladium catalyst (e.g., tetrakis(triphenylphosphine)palladium (Pd(PPh$_3$)$_4$), dichlorobis(triphenylphosphine)palladium (Cl$_2$Pd(PPh$_3$)$_2$), palladium acetate (Pd(OAc)$_2$), bis(tri-tert-butylphosphine)palladium(O) (Pd(tBu3P)$_2$), a mixture of the palladium catalyst and a copper catalyst (e.g., copper (I) iodide)), in the presence or absence of a phase transfer catalyst (e.g., tetrabutyl ammonium chloride, tetrabutyl ammonium bromide, tetrabutyl ammonium iodide, tetrabutylammonium acetate) at room temperature to 120° C.

Among the compounds represented by general formula (A-3 in reaction schemes 1 and 2, a compound represented by general formula (A-3-1):

[Formula 39]

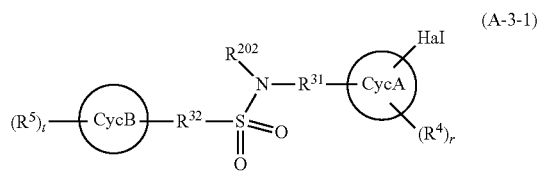

(A-3-1)

(wherein all symbols have the same meanings as mentioned above) can be produced by the method shown in reaction scheme 3 below.

Reaction Scheme 3

[Formula 40]

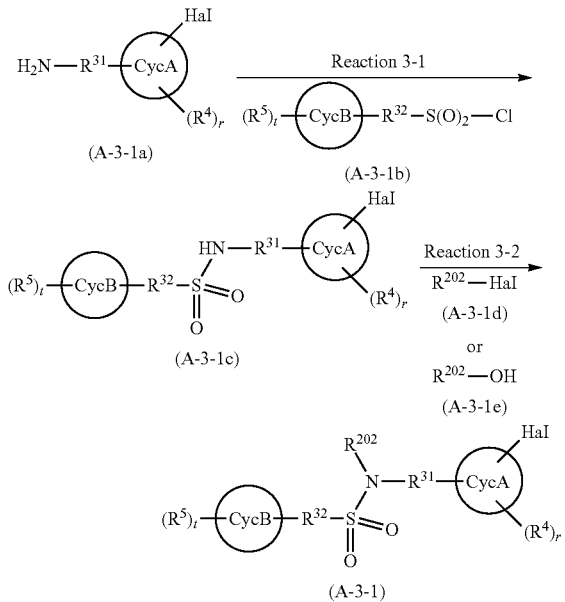

(wherein all symbols have the same meanings as mentioned above.)

In reaction scheme 3, the reaction 3-1 can be achieved by subjecting a compound represented by general formula (A-3-1a) and a compound represented by general formula (A-3-1b) to a sulfonamidation reaction. The sulfonamidation reaction is known, and can be achieved by, for example, carrying out the reaction in an organic solvent (e.g., ethyl acetate, isopropyl acetate, benzene, toluene, xylene, heptane, cyclohexane, THF, dioxane, dimethoxyethane, ethanol, 2-propanol, dimethylsulfoxide, DMF, N,N-dimethylacetamide, N-methyl-2-pyrrolidinone, methylene chloride, chloroform, acetone, acetonitrile, a mixed solvent composed of two or more of these solvents) or under solvent-free conditions, in the presence or absence of a base (e.g., diisopropylethylamine, pyridine, triethylamine, dimethylaniline, sodium hydroxide, sodium carbonate, potassium carbonate, cesium carbonate, sodium phosphate, potassium phosphate) in the presence or absence of a catalyst (e.g., 4-dimethylaminopyridine) at 0 to 120° C.

In reaction scheme 3, the reaction 3-2 can be carried out by subjecting a compound represented by general formula (A-3-1c) and a compound represented by general formula (A-3-1d) to an alkylation reaction or by subjecting a compound represented by general formula (A-3-1c) and a compound represented by general formula (A-3-1e) to a Mitsunobu reaction. The alkylation reaction is known, and can be achieved by, for example, carrying out the reaction in an organic solvent (e.g., DMF, dimethylsulfoxide, chloroform, dichloromethane, diethyl ether, THF, methyl tert-butyl ether, acetonitrile, water, a mixed solvent composed of two or more of these solvents) in the presence of a base (e.g., sodium hydroxide, potassium hydroxide, lithium hydroxide, barium hydroxide, calcium hydroxide, sodium carbonate, potassium carbonate, sodium hydride, lithium bis(trimethylsilyl)amide, potassium bis(trimethylsilyl)amide, sodium bis(trimethylsilyl)amide) at 0 to 100° C. The Mitsunobu reaction is known, and can be achieved by, for example, carrying out the reaction in an organic solvent (e.g., dichloromethane, diethyl ether, THF, acetonitrile, benzene, toluene) in the presence of an azo compound (e.g., diethyl azodicarboxylate, diisopropyl azodicarboxylate, 1,1'-(azodicarbonyl)-dipiperidine, 1,1'-azobis(N,N-dimethylformamide)) and a phosphine compound (e.g., triphenylphosphine, tributylphosphine, trimethylphosphine, polymer-supported triphenylphosphine) at 0 to 80° C.

Among the compounds represented by general formula (A-3) in reaction schemes 1 and 2, a compound represented by general formula (A-3-2):

[Formula 41]

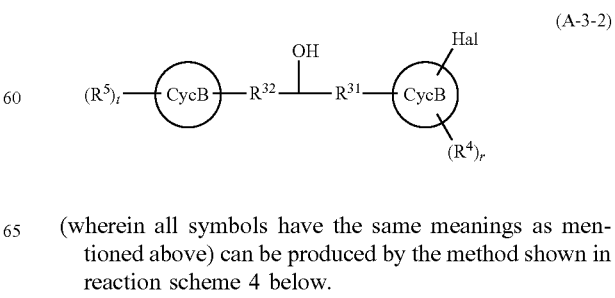

(A-3-2)

(wherein all symbols have the same meanings as mentioned above) can be produced by the method shown in reaction scheme 4 below.

[Formula 42]

Reaction Scheme 4

[Formula 42]

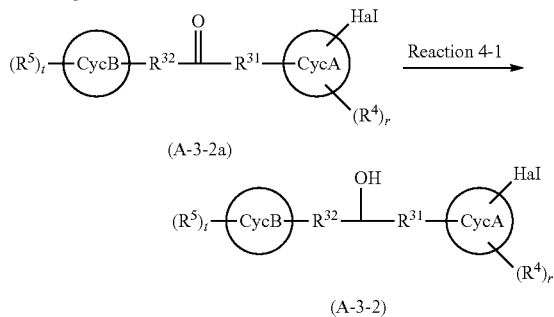

(A-3-2a)

(A-3-2)

(wherein all symbols have the same meanings as mentioned above.)

In reaction scheme 4, the reaction 4-1 can be achieved by, for example, reacting a compound represented by general formula (A-3-2a) in an organic solvent (e.g., THF, dimethoxyethane, toluene, dichloromethane, diethyl ether, dioxane, methanol) in the presence or absence of cerium chloride using a reducing agent (e.g., sodium borohydride, zinc bodohydride) at −20 to 50° C. In the case where it is intended to produce only one of stereoisomers selectively, the reaction is carried out using an asymmetric reducing agent (e.g., chlorodiisopinocampheylborane) or a combination of a chiral auxiliary agent and a reducing agent (e.g., (R)-2-methyl-CBS-oxazaborolidine and a borohydride-THF complex or a dimethyl sulfide borane complex, (S)-(−)-binaphthol and lithium aluminum hydride) at a temperature of −100 to 50° C.

In reaction scheme 1, 2, 3 or 4, in the case where a protecting group is present in a compound represented by each of the general formulae, a deprotection reaction may be carried out as required. The deprotection reaction for a protecting group is known, and can be carried out by the following methods. For example, (1) a deprotection reaction by alkaline hydrolysis, (2) a deprotection reaction under acidic conditions, (3) a deprotection reaction by hydrogenolysis, (4) a reaction of the deprotection of a silyl group, (5) a deprotection reaction using a metal, and (6) a deprotection reaction using a metal complex can be mentioned.

These methods will be described concretely as follows.

(1) The deprotection reaction by alkaline hydrolysis can be carried out, for example, in an organic solvent (e.g., methanol, THF, dioxane) using a hydroxide of an alkali metal (e.g., sodium hydroxide, potassium hydroxide, lithium hydroxide), a hydroxide of an alkaline earth metal (e.g., barium hydroxide, calcium hydroxide), a carbonate (e.g., sodium carbonate, potassium carbonate) or an aqueous solution thereof or a mixture thereof at 0 to 40° C.

(2) The deprotection reaction under acidic conditions can be carried out, for example, in an organic solvent (e.g., dichloromethane, chloroform, dioxane, ethyl acetate, methanol, isopropyl alcohol, THF, anisole) in an organic acid (e.g., acetic acid, trifluoroacetic acid, methanesulfonic acid, p-tosic acid) or an inorganic acid (e.g., hydrochloric acid, sulfuric acid) or a mixture thereof (e.g., hydrogen bromide/acetic acid) in the presence or absence of 2,2,2-trifluoroethanol at 0 to 100° C.

(3) The deprotection reaction by hydrogenolysis can be carried out, for example, in a solvent (e.g., an ether-type solvent (e.g., THF, dioxane, dimethoxyethane, diethyl ether), an alcohol-type solvent (e.g., methanol, ethanol), a benzene-type solvent (e.g., benzene, toluene), a ketone-type solvent (e.g., acetone, methyl ethyl ketone), a nitrile-type solvent (e.g., acetonitrile), an amide-type solvent (e.g., DMF), water, ethyl acetate, acetic acid or a mixed solvent composed of two or more of these solvents) in the presence of a catalyst (e.g., palladium-carbon, palladium black, palladium hydroxide-carbon, platinum oxide, raney nickel) under a hydrogen atmosphere under ambient pressure or under pressure or in the presence of ammonium formate at 0 to 200° C.

(4) The reaction of deprotection of a silyl group can be carried out, for example, in an organic solvent miscible in water (e.g., THF, acetonitrile) using tetrabutylammonium fluoride at 0 to 40° C. Alternatively, the deprotection reaction can also be carried out, for example, in an organic acid (e.g., acetic acid, trifluoroacetic acid, methanesulfonic acid, p-tosic acid) or an inorganic acid (e.g., hydrochloric acid, sulfuric acid) or a mixture thereof (e.g., hydrogen bromide/acetic acid) at −10 to 100° C.

(5) The deprotection reaction using a metal can be carried out, for example, in an acidic solvent (e.g., a mixed solution of acetic acid, a buffer solution having a pH value of 4.2 to 7.2 or a solution thereof with an organic solvent such as THF) in the presence of a zinc powder at 0 to 40° C. optionally while applying ultrasonic waves.

(6) The deprotection reaction using a metal complex can be carried out, for example, in an organic solvent (e.g., dichloromethane, DMF, THF, ethyl acetate, acetonitrile, dioxane, ethanol), water or a mixed solvent thereof in the presence of a trapping reagent (e.g., tributyltin hydride, triethylsilane, dimedone, morpholine, diethylamine, pyrrolidine), an organic acid (e.g., acetic acid, formic acid, 2-ethyl hexanoic acid) and/or an organic acid salt (e.g., sodium 2-ethylhexanoate, potassium 2-ethylhexanoate) in the presence or absence of a phosphine-type reagent (e.g., triphenylphosphine) using a metal complex (e.g., tetrakis(triphenylphosphine)palladium (0), dichlorobis(triphenylphosphine)palladium (II), palladium acetate (II), chlorotris(triphenylphosphine)rhodium (I)) at 0 to 40° C.

In addition to the above-mentioned methods, the deprotection reaction can also be carried out by, for example, the method described in T. W. Greene, Protective Groups in Organic Synthesis, Wiley, New York, 1999.

Examples of the protecting group for a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, and a 2,2,2-trichloroethoxycarbonyl (Troc) group.

Examples of the protecting group for an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethyloxycarbonyl group, a benzyl (Bn) group, a p-methoxybenzyl group, a benzyloxymethyl (BOM) group, and a 2-(trimethylsilyl)ethoxymethyl (SEM) group.

In addition to the above-mentioned protecting groups, the protecting group for a hydroxyl group or an amino group is not particularly limited, as long as the protecting group can be detached easily and selectively. For example, the protecting groups mentioned in T. W. Greene, Protective Groups in Organic Synthesis, Wiley, New York, 1999 can be used.

In each of the reactions mentioned in the description, a compound to be used as a starting raw material, e.g., compound represented by general formulae (A-1), (A-3), (A-3-1a) and (A-3-1b), is known or can be produced easily by a known method.

In each of the reactions mentioned in the description, a reaction including heating can be carried out using a water bath, an oil bath, a sand bath or microwaves, as apparent to persons skilled in the art.

In each of the reactions mentioned in the description, a solid-phase-supported reagent that is supported on a high-molecular-weight polymer (e.g., polystyrene, polyacrylamide, polypropylene, polyethylene glycol) may also be used appropriately.

In each of the reactions mentioned in the description, a reaction product can be purified by a conventional purification means, such as distillation under ambient pressure or under reduced pressure, high-performance liquid chromatography using silica gel or magnesium silicate, thin-layer chromatography, an ion exchange resin, a scavenger resin, column chromatography, washing and recrystallization. The purification may be carried out for every reactions, or may be carried out after the completion of several reactions.

[Toxicity]

The toxicity of the compound of the present invention is sufficiently low, and therefore can be used as a medicament safely.

[Application to Medicament]

The compound of the present invention has a nerve-protecting and/or -repairing activity.

In one embodiment, the compound of the present invention has a nerve-protecting and/or -repairing activity having excellent sustainability.

Therefore, the compound of the present invention is useful for, for example, the treatment of a disease associated with neuropathy.

In the present invention, one example of the nerve-protecting and/or -repairing activity is a nerve-protecting and/or -repairing activity through a glial cell (e.g., a microglia, an astrocyte, an oligodendrocyte, an ependiomocyte, a Schwann cell, a satellite cell). One example of the nerve-protecting and/or -repairing activity through a glial cell is an activity to promote the myelination of a Schwann cell.

In the present invention, the neuropathy includes peripheral neuropathy and a central neuropathy. Examples of the disease associated with peripheral neuropathy include diabetic neuropathy, a metabolic peripheral neuropathy associated with uremia, peripheral neuropathy associated with vitamin B deficiency, peripheral neuropathy associated with an infectious disease such as diphtheria, botulism food poisoning, herpes virus (herpes zoster), a drug-induced peripheral neuropathy associated with the administration of phenytoin that is an anti-convulsant agent, an anti-microbial agent (e.g., chloramphenicol, nitrofurantoin, a sulfonamide-type drug), a chemotherapeutic drug (taxane-base: paclitaxel, docetaxel, etc., a platinum preparation: oxaliplatin, cisplatin, carboplatin, nedaplatin, etc., *vinca* alkaloid-base: vinblastine, vincristine, vindesine, etc.) or a sedative agent (e.g., barbital, hexobarbital), chronic inflammatory demyelinating polyneuropathy, Guillain-Barre syndrome, entrapment neuropathy (e.g., carpal tunnel syndrome, thoracic outlet syndrome, cubital tunnel syndrome, *piriformis* syndrome, tarsal tunnel syndrome, peroneal nerve entrapment neuropathy), an immunological peripheral neuropathy such as multifocal motor neuropathy, peripheral neuropathy associated with an allergic disease such periarteritis nodosa, allergic vasculitis and systemic lupus erythematosus, a toxic peripheral neuropathy associated with the ingestion of a heavy metal such as lead, mercury, arsenic and thallium, an organic solvent such as thinner, an organic phosphorus-based insecticide, a toxic substance such as tri-ortho-cresyl phosphate (TOCP) or an alcohol, peripheral neuropathy induced by the compression of a nerve by cancer, and peripheral neuropathy associated with a genetic disease (e.g., hypothyroidism, renal failure, Charcot-Marie-Tooth disease, Refsum disease, *porphyria*, Fabry disease, hereditary neuropathy to pressure palsies).

Examples of the disease associated with a central neuropathy include Alzheimer's disease, Parkinson's disease, Dementia with Lewy Bodies, frontotemporal lobar degeneration, progressive supranuclear palsy, corticobasal degeneration, Huntington's disease, dystonia, prion disease, multiple system atrophy, spinocerebellar degeneration, amyotrophic lateral sclerosis, primary lateral sclerosis, spinal and bulbar muscular atrophy, spinal muscular atrophy, spastic paraplegia, syringomyelia, multiple sclerosis, neuromyelitis optica, concentric sclerosis, acute disseminated encephalomyelitis, inflammatory diffuse sclerosis, subacute sclerosing panencephalitis, an infectious neuropathy such as progressive multifocal leukoencephalopathy, a toxic/metabolic neuropathy such as hypoxic ischemic encephalopathy and central pontine myelinolysis, and a vasculitic neuropathy such as Binswanger s disease.

In the present invention, one example of the prevention and/or treatment of peripheral neuropathy is the prevention and/or treatment of a peripheral neuropathic pain.

With respect to a combined drug comprising the compound of the present invention and other drug, the combined drug may be administered in the form of a blended preparation in which both of the components are blended in a single preparation, or these drugs may be prepared separately and administered. In the case where the drugs are prepared separately and administered, the administration includes simultaneous administration and time difference administration. In the case of time difference administration, it is possible to administer the compound of the present invention first and administer other drug later, or administer other drug first and administer the compound of the present invention later. The method for the administration of the compound of the present invention and the method for the administration of other drug may be the same as or different from each other.

The disease on which the combined drug can exert the prophylactic and/or therapeutic effect thereof is not particularly limited, and any disease may be employed as long as the prophylactic and/or therapeutic effect of the compound of the present invention can be complemented or enhanced against the disease.

Examples of other drug for complementing and/or enhancing the prophylactic and/or therapeutic effect of the compound of the present invention against a disease associated with neuropathy include an aldose reductase inhibiting drug, a vitamin agent and a brain protecting drug. An example of the aldose reductase inhibiting drug is epalrestat. An example of the vitamin agent is mecobalamin. An example of the brain protecting drug is edaravone.

The concomitant drug to be used in combination with the compound of the present invention includes drugs which have been discovered until now as well as drugs which will be discovered in the future.

In general, the compound of the present invention is administered systemically or topically in an oral or parenteral dosage form. Examples of the oral preparation include a liquid preparation for internal use (e.g., an elixir, a syrup, a pharmaceutically acceptable water-based preparation, a suspension, an emulsion) and a solid preparation for internal use (e.g., tablets (including sublingual tablets and orally disintegrating tablets), pills, capsules (including hard capsules, soft capsules, gelatin capsules and micro capsules), a powder, a granule, a lozenge). Examples of the parenteral preparation include a liquid preparation (e.g., an injection (including an intravitreal injection, a subcutaneous injection, an intravenous injection, an intramuscular injection, an intraperitoneal injection, a drip infusion), eye drops (including water-based eye drops (e.g., a water-based eye drop solution, a water-based eye drop suspension, a viscous eye drop solution, a solubilized eye drop solution), a non-water-based eye drops (e.g., a non-water-based eye drop solution, a non-water-based eye drop suspension)), an external preparation (including an ointment (e.g., an eye ointment)), and ear drops. These preparations may be release-controlled preparations such as rapid-release preparations and sustained-release preparations. These preparations can be produced by known methods, such as the methods described in the Japanese Pharmacopoeia.

The liquid preparation for internal use that is used as an oral preparation can be produced by, for example, dissolving, suspending or emulsifying an active ingredient in a commonly used diluting agent (e.g., purified water, ethanol, a mixed solution thereof). The liquid preparation may further contain a wetting agent, a suspending agent, an emulsifying agent, a sweetening agent, a flavoring agent, an aroma-imparting agent, a preservative agent, a buffering agent and the like.

The solid preparation for internal use that is used as an oral preparation can be formulated in accordance with the conventional method by, for example, mixing an active ingredient with an excipient (e.g., lactose, mannitol, glucose, microcrystalline cellulose, starch), a binder (e.g., hydroxypropyl cellulose, polyvinylpyrrolidone, magnesium aluminometasilicate), a disintegrating agent (e.g., calcium carboxymethyl cellulose), a lubricating agent (e.g., magnesium stearate), a stabilizing agent, a dissolution aid (glutamic acid, aspartic acid) and the like. If necessary, the solid preparation may be coated with a coating agent (e.g., white sugar, gelatin, hydroxypropyl cellulose, hydroxypropylmethylcellulose phthalate) or may be coated with two or more layers.

The external preparation that is used as a parenteral preparation can be produced by a known method or by using a commonly employed formulation. For example, the ointment can be produced by triturating or melting an active ingredient in a base agent. The ointment base agent can be selected from known or commonly used materials. For example, one or two or more components selected from a higher fatty acid or a higher fatty acid ester (e.g., adipic acid, myristic acid, palmitic acid, stearic acid, oleic acid, an adipic acid ester, a myristic acid ester, a palmitic acid ester, a stearic acid ester, an oleic acid ester), a wax (e.g., bee's wax, spermaceti wax, ceresine wax), a surfactant (e.g., a polyoxyethylene alkyl ether phosphate ester), a higher alcohol, (e.g., cetanol, stearyl alcohol, cetostearyl alcohol), a silicone oil (e.g., dimethylpolysiloxane), a hydrocarbon (e.g., hydrophilic petrolatum, white petrolatum, purified lanolin, liquid paraffin), a glycol (e.g., ethylene glycol, diethylene glycol, propylene glycol, polyethylene glycol, macrogol), a vegetable oil (e.g., castor oil, olive oil, sesame oil, turpentine oil), an animal oil (e.g., mink oil, egg-yolk oil, squalane, squalene), water, an absorption promoter and an anti-rash agent are used singly or in a mixed form. The ointment may further contain a moisturizing agent, a preservative agent, a stabilizing agent, an anti-oxidative agent, an aroma-imparting agent and the like.

The injection that is used as a parenteral preparation includes a solid injection which is dissolved or suspended in a solution, a suspension, an emulsion or a solvent for extemporaneous use, upon use. The injection is used in a form prepared by, for example, dissolving, suspending or emulsifying an active ingredient in a solvent. Examples of the solvent to be used include distilled water for injection use, physiological saline, a vegetable oil, an alcohol such as propylene glycol, polyethylene glycol and ethanol, and a combination thereof. The injection may further contain a stabilizing agent, a dissolution aid (e.g., glutamic acid, aspartic acid, polysorbate 80 (registered trademark)), a suspending agent, an emulsifying agent, an analgesic agent, a buffering agent, a preservative agent and the like. The injection is sterilized in a final step, or is produced by a germ-free operation method. Alternatively, it is also possible to produce a germ-free solid preparation, e.g., a freeze-dried product, of the injection and dissolve the solid preparation in sterilized or germ-free distilled water for injection or other solvent before use.

For the application of the compound of the present invention or a combined drug of the compound of the present invention and other drug for the above-mentioned purposes, the compound of the present invention or the combined drug is generally administered systemically or topically in an oral or parenteral dosage form. The dose amount may vary depending on ages, body weights, clinical conditions, therapeutic effects, methods of administration, time periods of treatment and the like, and is generally administered orally in a single dose or in several divided doses daily at a single dose of 1 ng to 1000 mg per dose per adult person or administered parenterally in a single dose or in several divided doses daily in a dose amount of 0.1 ng to 10 mg per dose per adult person, or administered intravenously in a sustainable manner for 1 to 24 hours daily per adult person. As mentioned above, the dose amount varies depending on various factors. Therefore, the administration in a smaller dose amount than the above-mentioned dose amount may be sufficient, or the administration in a larger dose amount than the above-mentioned dose amount may be needed.

EXAMPLES

Hereinbelow, the present invention will be described in detail with reference to examples. However, the present invention is not limited by these examples.

A solvent mentioned in a section relating to the separation by chromatography or shown in parentheses in TLC data is an elution solvent or a developing solvent used, wherein the ratio is expressed by volume.

The conditions employed in the LC/MS analyses in the following examples are shown below. Column: YMC Triart C18, 2.0 mm×30 mm, 1.9 m; flow rate: 1.0 mL/min; temperature: 30° C.; mobile phase A: a 0.1% aqueous TFA solution; mobile phase B: a 0.1% TFA acetonitrile solution; gradient (the (mobile phase A): (mobile phase B) ratio): 0 to 0.10 minute (95:5), 0.10 to 1.20 minutes (95:5 to 5:95), 1.20 to 1.50 minutes (5:95).

A substance shown in parentheses in NMR data represents a solvent used for the measurement.

Each of the compounds used in the description was named using a computer program "ACD/Name" (registered trademark) manufactured by Advanced Chemistry Development (which generally names in accordance with the IUPAC nomenclature rule) or was named in accordance with the IUPAC nomenclature method.

Example 1: Isopropyl 3-(2-hydroxyphenyl)propanoate

Sulfuric acid (0.26 mL) was added to a solution of 3,4-dihydrocoumarin (50.0 g) in isopropyl alcohol (500 mL), and the reaction mixture was stirred at room temperature for 2 hours. The reaction mixture was concentrated under a reduced pressure, and the resultant residue was diluted with ethyl acetate. The solution was washed with a saturated aqueous sodium bicarbonate solution, water and saturated saline, was then dried over sodium sulfate, and was then concentrated under a reduced pressure. In this manner, the title compound (73.2 g) having the physical property values shown below was produced.
$^1$H-NMR (CDCl$_3$): δ 1.20, 2.66-2.70, 2.87-2.91, 4.95-5.08, 6.86-6.91, 7.06-7.15, 7.35.

Example 2: Isopropyl 3-(2-(2-(1,3-dioxan-2-yl)ethoxy)phenyl)propanoate

Potassium phosphate (2.85 g) was added to a solution of the compound produced in Example 1 (2.00 g) and 2-(2-bromoethyl)-1,3-dioxane (2.43 g) in DMF (4 mL), and the reaction mixture was stirred at 70° C. for 2 hours. The reaction mixture was poured into 1 M hydrochloric acid, and the resultant solution was extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=95:5→4:1). In this manner, the title compound (2.73 g) having the physical property value shown below was produced.
TLC: Rf 0.57 (hexane: ethyl acetate=2:1).

Example 3: Isopropyl 3-(2-(3-oxopropoxy)phenyl)propanoate

A solution of the compound produced in Example 2 (500 mg) and lutidine (0.40 mL) in dichloromethane (1.5 mL) was cooled to −15° C., and trimethylsilyltrifluoromethanesulfonate (0.42 mL) was added to the solution. The resultant reaction mixture was stirred at 0° C. for 2 hours. Ice (10 g) was added to the reaction solution, and the resultant solution was stirred at 0° C. for 15 minutes. Water and ethyl acetate were added to the solution, the resultant solution was stirred at 0° C. for 20 hours, the resultant reaction mixture was poured into 1 M hydrochloric acid and ethyl acetate, and the resultant solution was extracted with ethyl acetate. An organic layer was washed with water and saturated saline, was then dried over sodium sulfate, and was then concentrated under a reduced pressure. In this manner, the title compound (443 mg) having the physical property values shown below was produced.
$^1$H-NMR (CDCl$_3$): δ 1.20, 2.50-2.55, 2.93-2.96, 4.33, 4.98, 6.85-6.92, 7.14-7.19, 9.90.

Example 4: Isopropyl 3-(2-((3-hydroxy-5-(trimethylsilyl)pent-4-yn-1-yl)oxy)phenyl)propanoate A solution of trimethylsilylacetylene (5.0 mL) in THF (70 mL) was cooled to −70° C., then n-butyllithium (a 1.6 M hexane solution, 20 mL) was added to the solution, and the reaction mixture was the stirred at −70° C. for 30 minutes. A solution of the compound produced in Example 3 (7.15 g) in THF (10 mL) was added dropwise to the solution, and the resultant reaction mixture was stirred at 0° C. for 2 hours. The reaction mixture was poured into a saturated aqueous ammonium chloride solution, and the resultant solution was then extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=95:5→7:3). In this manner, the title compound (1.8 g) having the physical property values shown below was produced
$^1$H-NMR (CDCl$_3$): δ 0.17, 1.19, 2.22-2.33, 2.56, 2.87-2.98, 4.09-4.23, 4.70, 3.60-4.93-5.03, 6.86-6.91, 7.14-7.18.

Example 5: Isopropyl 3-(2-((3-hydroxypent-4-yn-1-yl)oxy)phenyl)propanoate

A solution of the compound produced in Example 4 (6.89 g) in THF (38 mL) was cooled to 0° C., and tetrabutylammonium fluoride (abbreviated as "TBAF", hereinafter) (a 1.0-M THF solution, 7.3 mL) was then added to the solution. The reaction mixture was stirred at 0° C. for 10 minutes. The reaction mixture was poured into 1 M hydrochloric acid, and the resultant solution was extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=95:5→1:1). In this manner, the title compound (5.06 g) having the physical property values shown below was produced.
$^1$H-NMR (CDCl$_3$): δ 1.19, 2.20-2.26, 2.43, 2.50-2.59, 2.87-2.96, 4.08-4.26, 4.74, 4.99, 6.86-6.91, 7.14-7.21.

Example 6: Isopropyl (R)-3-(2-((3-hydroxypent-4-yn-1-yl)oxy)phenyl)propanoate Vinyl acetate (4 mL) was added to a solution of the compound produced in Example 5 (1.2 g) in heptane (24 mL). CHIRAZYME L-5 CA (trade name) (0.4 g) was added to the solution, and he resultant reaction mixture was stirred at 45° C. for 9 hours. The reaction mixture was filtrated through Celite (trade name), and a filtrate was concentrated under a reduced pressure. The resultant residue was purified by silica gel column chromatography (hexane: ethyl acetate=95:5→1:1) to produce the title compound (0.54 g, >99% ee) having the physical property values shown below. The compound thus produced was analyzed by high-performance liquid chromatography (column used: Daicel Corporation, CHIRALPAK-IB (4.6 mm×250 mm), mobile phase: hexane: 2-propanol=95:5, flow rate: 1 mL/min, wavelength: 254 nm, column temperature: 40° C.). As a result, the retention time was 10.6 minutes.
$^1$H-NMR (CDCl$_3$): δ 1.19, 2.20-2.26, 2.41, 2.50-2.59, 2.90-2.96, 4.08-4.26, 4.74, 4.99, 6.86-6.91, 7.14-7.21.

Example 7: Isopropyl (R)-3-(2-((3-((trimethylsilyl)oxy)pent-4-yn-1-yl)oxy)phenyl)propanoate A solution of the compound produced in Example 6 (500 mg) in DMF (3.4 mL) was cooled to 0° C., and chlorotrimethylsilane (0.24 mL) was then added to the solution. The reaction mixture was stirred at room temperature for 2 hours. The reaction mixture was poured into water, and the resultant solution as extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=100: 0→9:1). In this manner, the title compound (600 mg) having the physical property values shown below was produced.

$^1$H-NMR (CDCl$_3$): δ 0.17, 1.21, 2.18, 2.43, 2.54-2.59, 2.90-2.95, 4.06-4.15, 4.67, 4.99, 6.83-6.89, 7.14-7.20.

Example 8: Isopropyl (R,E)-3-(2-((5-(4,4,5,5-tetramethyl-1,3,2-dioxaboran-2-yl)-3-((trimethylsilyl)oxy)pent-4-en-1-yl)oxy)phenyl)propanoate 4,4,5,5-Tetramethyl-1,3,2-dioxaborolane (2.09 g) and 4-dimethylaminobenzoic acid (53.9 mg) were added to a solution of the compound produced in Example 7 (2.45 g) in heptane (6 mL), and the resultant solution was stirred at 100° C. for 13 hours. The reaction solution was cooled to room temperature, and was then concentrated. The resultant residue was purified by silica gel column chromatography (hexane: ethyl acetate=20:1→3:1). In this manner, the title compound (1.45 g) having the physical property value shown below was produced.

HPLC retention time (min): 1.14.

Example 9: N-(3-Bromophenyl)benzenesulfonamide

Pyridine (0.95 mL), N,N-dimethylaminopyridine (abbreviated as "DMAP", hereinafter) (72.4 mg) and benzenesulfonyl chloride (1.10 g) were added to a solution of 3-bromoaniline (1.02 g) in dichloromethane (20 mL) at 0° C., and the resultant solution was stirred at room temperature for 2 hours. The reaction solution was concentrated, and the resultant residue was then purified by silica gel column chromatography (hexane: ethyl acetate=9:1→2:1). In this manner, the title compound (1.96 g) having the physical property value shown below was produced.

HPLC retention time (min): 0.98.

Example 10: Propan-2-yl 3-[2-[(E,3R)-5-[3-(benzenesulfonamido)phenyl]-3-hydroxypent-4-enoxy]phenyl]propanoate The compound produced in Example 9 (1.18 g), chloro(2-dicyclohexylphosphino-2',4',6'-triisopropyl-1,1'-biphenyl)[2-(2'-amino-1,1'-biphenyl)]palladium (II) (CAS Registry Number: 1310584-14-5) (0.30 g) and a 2-M aqueous tripotassium phosphate solution (5.7 mL) were added to a solution of the compound produced in Example 8 (2.00 g) in THF (18 mL), and the resultant solution was stirred at 60° C. for 2 hours. The reaction solution was cooled to room temperature, water was then added to the solution, and the resultant solution was extracted with ethyl acetate. An organic layer was dried over sodium sulfate, and was then concentrated under a reduced pressure. TBAF (a 1.0 M THF solution, 6.3 mL) was added to a solution of the resultant residue in THF (6 mL), and the solution was stirred at room temperature for 1 hour. Water was added to the reaction solution, and the resultant solution was extracted with ethyl acetate. An organic layer was dried over sodium sulfate, and was then concentrated under a reduced pressure. The resultant residue was purified by silica gel column chromatography (hexane: ethyl acetate=9:1→2:1). In this manner, the title compound (1.41 g) having the physical property values shown below was produced.

HPLC retention time (min): 1.10;
$^1$H-NMR (CDCl$_3$): δ 1.21, 2.05-2.17, 2.21, 2.57-2.61, 2.91-2.95, 4.11-4.19, 4.62, 5.02, 6.25, 6.55, 6.72, 6.85-6.91, 6.99, 7.09-7.22, 7.41-7.45, 7.53, 7.75-7.78.

Example 11: 3-[2-[(E,3R)-5-[3-(Benzenesulfonamido)phenyl]-3-hydroxypent-4-enoxy]phenyl]propanoic acid

[Formula 43]

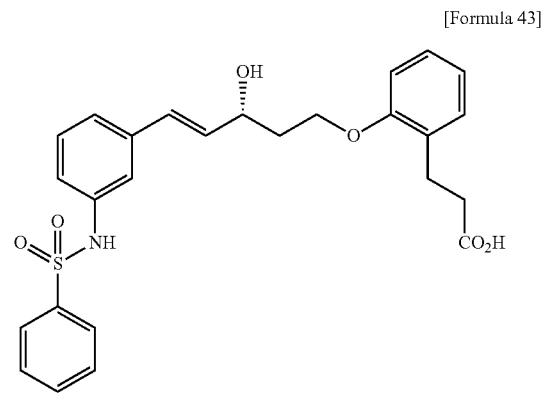 [SMILES: O=C(O)CCc1ccccc1OCC[C@@H](O)/C=C/c1cccc(NS(=O)(=O)c2ccccc2)c1]

A 1-M aqueous lithium hydroxide solution (5 mL) was added to a solution of the compound produced in Example 10 (680 mg) in THF (5 mL) and methanol (1 mL), and the resultant solution was stirred at 30° C. for 18 hours. 1 M Hydrochloric acid was added to the solution to render the solution acidic, and the resultant solution was extracted with ethyl acetate. An organic layer was dried over sodium sulfate, and was then concentrated under a reduced pressure. In this manner, the title compound (600 mg) having the physical property values shown below was produced.

HPLC retention time (min): 0.93;
$^1$H-NMR (CD$_3$OD): δ 2.05-2.10, 2.57-2.61, 2.91-2.95, 4.10, 4.17, 4.51-4.56, 6.24, 6.53, 6.86, 6.93, 6.98, 7.12-7.20, 7.45-7.50, 7.56, 7.75-7.78.

Examples 12(1) to (13)

The same designed procedures as in Example 10→Example 11 were carried out using, in place of N-(3-bromophenyl)benzenesulfonamide used in Example 10, corresponding halide compounds. In this manner, the following compounds of Examples were produced.

Example 12(1): 3-[2-[(E,3R)-5-(3-Benzamidophenyl)-3-hydroxypent-4-enoxy]phenyl]propanoic acid HPLC retention time (min): 0.95;
$^1$H-NMR (CD$_3$OD): δ 2.10-2.15, 2.59-2.63, 2.93-2.97, 4.13, 4.21, 4.60, 6.39, 6.67, 6.86, 6.95, 7.16, 7.24, 7.33, 7.52-7.63, 7.81, 7.95-7.97.

Example 12(2): 3-[2-[(E,3R)-5-[4-(Benzenesulfonamido)phenyl]-3-hydroxypent-4-enoxy]phenyl]propanoic acid

[Formula 44]

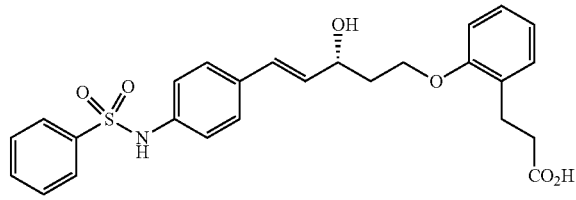

HPLC retention time (min): 0.92;
MS (ESI, Pos.): 464 (M+H–H$_2$O)$^+$.

Example 12(3): 3-[2-[(E,3R)-5-(4-Benzamidophenyl)-3-hydroxypent-4-enoxy]phenyl]propanoic acid HPLC retention time (min): 0.95;
$^1$H-NMR (CD$_3$OD): δ 2.10-2.14, 2.58-2.63, 2.93-2.97, 4.13, 4.20, 4.58, 6.32, 6.64, 6.86, 6.95, 7.15-7.20, 7.44-7.55, 7.60, 7.67-7.71, 7.93-7.97.

Example 12(4): 3-[2-[(E,3R)-5-[2-(Benzenesulfonamido)phenyl]-3-hydroxypent-4-enoxy]phenyl]propanoic acid HPLC retention time (min): 0.94;
MS (ESI, Pos.): 464 (M+H–H$_2$O)$^+$.

Example 12(5): 3-[2-[(E,3R)-5-(2-Benzamidophenyl)-3-hydroxypent-4-enoxy]phenyl]propanoic acid HPLC retention time (min): 0.89;
MS (ESI, Pos.): 428 (M+H–H$_2$O)$^+$.

Example 12(6): 3-[2-[(E,3R)-5-[3-(Benzylamino)phenyl]-3-hydroxypent-4-enoxy]phenyl]propanoic acid HPLC retention time (min): 0.85;
$^1$H-NMR (CD$_3$OD): δ 2.05-2.10, 2.57-2.61, 2.92-2.95, 4.10, 4.17, 4.33, 4.52, 6.19, 6.49-6.56, 6.69-6.71, 6.85, 6.93, 7.04, 7.15-7.24, 7.29-7.33, 7.37-7.39.

Example 12(7): 3-[2-[(E,3R)-3-Hydroxy-5-[3-(phenylsulfamoyl)phenyl]pent-4-enoxy]phenyl]propanoic acid HPLC retention time (min): 0.94;
MS (ESI, Pos.): 464 (M+H–H$_2$O)$^+$.

Example 12(8): 3-[2-[(E,3R)-3-Hydroxy-5-[3-(phenylcarbamoyl)phenyl]pent-4-enoxy]phenyl]propanoic acid HPLC retention time (min): 0.95;
MS (ESI, Pos.): 428 (M+H–H$_2$O)$^+$.

Example 12(9): 3-[2-[(E,3R)-3-Hydroxy-5-[3-(1-hydroxy-2-phenylethyl)phenyl]pent-4-enoxy]phenyl]propanoic acid HPLC retention time (min): 0.96;
$^1$H-NMR (CD$_3$OD): δ 2.08-2.13, 2.58-2.62, 2.93-2.98, 3.06, 4.11, 4.19, 4.56, 4.84, 6.27, 6.62, 6.86, 6.94, 7.10-7.31.

Example 12(10): 3-[2-[(E,3R)-5-[3-(Benzenesulfonamidomethyl)phenyl]-3-hydroxypent-4-enoxy]phenyl]propanoic acid HPLC retention time (min): 0.93;
MS (ESI, Pos.): 478 (M+H–H$_2$O)$^+$.

Example 12(11): 3-[2-[(E,3R)-5-[2-(Benzenesulfonamidomethyl)phenyl]-3-hydroxypent-4-enoxy]phenyl]propanoic acid HPLC retention time (min): 0.97;
$^1$H-NMR (CDCl$_3$): δ 1.99-2.07, 2.11-2.19, 2.68-2.72, 2.95-3.08, 4.12-4.26, 4.73-4.78, 6.12, 6.59, 6.86-6.92, 7.04-7.11, 7.16-7.23, 7.33-7.38, 7.44-7.48, 7.64-7.67.

Example 12(12): 3-[2-[(E,3R)-5-[1-(Benzenesulfonyl)-2-methylindol-4-yl]-3-hydroxypent-4-enoxy]phenyl]propanoic acid HPLC retention time (min): 1.10;
MS (ESI, Pos.): 502 (M+H–H$_2$O)$^+$.

Example 12(13): 3-[2-[(E,3R)-3-Hydroxy-5-[3-(2-hydroxy-1-phenylpropan-2-yl)phenyl]pent-4-enoxy]phenyl]propanoic acid HPLC retention time (min): 1.00;
$^1$H-NMR (CDCl$_3$): δ 2.10-2.15, 2.65-2.68, 2.94-3.14, 4.12-4.22, 4.62, 6.28, 6.64, 6.86-6.91, 7.00-7.02, 7.15-7.28, 7.44.

Examples 13(1) to (19)

The same designed procedures as in Example 9→Example 10→Example 11 were carried out using, in place of 3-bromoaniline used in Example 9, corresponding amine compounds. In this manner, the following compounds of Examples were produced.

Example 13(1): 3-[2-[(E,3R)-5-[3-(Benzenesulfonamido)-2-methylphenyl]-3-hydroxypent-4-enoxy]phenyl]propanoic acid

[Formula 45]

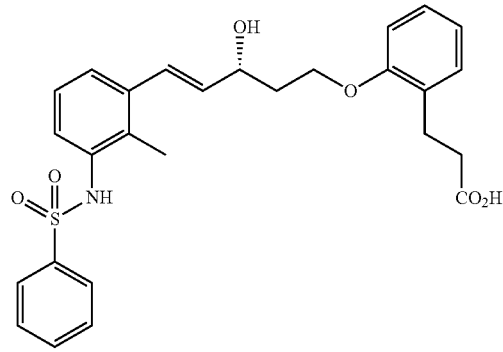

HPLC retention time (min): 0.94;
$^1$H-NMR (CD$_3$OD): δ 1.96, 2.07-2.12, 2.56-2.60, 2.90-2.94, 4.10, 4.18, 4.57, 6.12, 6.78, 6.84-6.93, 7.04, 7.15-7.20, 7.36, 7.47-7.51, 7.60, 7.65-7.67.

Example 13(2): 3-[2-[(E,3R)-5-[5-(Benzenesulfonamido)-2-methylphenyl]-3-hydroxypent-4-enoxy]phenyl]propanoic acid HPLC retention time (min): 0.95;
$^1$H-NMR (CD$_3$OD): δ 2.05-2.11, 2.19, 2.56-2.60, 2.91-2.95, 4.09, 4.19, 4.56, 6.01, 6.76, 6.84-6.94, 6.99, 7.12-7.20, 7.44-7.48, 7.56, 7.73-7.75.

Example 13(3): 3-[2-[(E,3R)-5-[3-(Benzenesulfonamido)-5-methylphenyl]-3-hydroxypent-4-enoxy]phenyl]propanoic acid HPLC retention time (min): 0.96;
$^1$H-NMR (CD$_3$OD): δ 1.93-1.98, 2.12, 2.45-2.49, 2.79-2.83, 3.98, 4.05, 4.41, 6.09, 6.37, 6.69, 6.74, 6.80-6.83, 7.03-7.08, 7.34-7.38, 7.44, 7.63-7.66.

Example 13(4): 3-[2-[(E,3R)-5-[3-(Benzenesulfonamido)-4-methylphenyl]-3-hydroxypent-4-enoxy]phenyl]propanoic acid HPLC retention time (min): 0.94;
$^1$H-NMR (CD$_3$OD): δ 1.89-1.97, 1.91, 2.46-2.50, 2.81-2.84, 3.98, 4.06, 4.40, 5.98, 6.37, 6.75, 6.83, 6.90, 6.97, 7.04-7.09, 7.34-7.38, 7.46, 7.56-7.58.

Example 13(5): 3-[2-[(E,3R)-5-[3-(Benzenesulfonamido)-2-fluorophenyl]-3-hydroxypent-4-enoxy]phenyl]propanoic acid HPLC retention time (min): 0.94;
$^1$H-NMR (CD$_3$OD): δ 2.03-2.09, 2.55-2.59, 2.89-2.93, 4.09, 4.16, 4.53, 6.36, 6.63, 6.86, 6.92, 7.06, 7.15-7.19, 7.30-7.37, 7.45-7.49, 7.57, 7.75-7.77.

Example 13(6): 3-[2-[(E,3R)-5-[5-(Benzenesulfonamido)-2-fluorophenyl]-3-hydroxypent-4-enoxy]phenyl]propanoic acid HPLC retention time (min): 0.94;
$^1$H-NMR (CD$_3$OD): δ 1.90-2.01, 2.45-2.49, 2.79-2.83, 3.99, 4.07, 4.43, 6.17, 6.56, 6.75, 6.81-6.88, 7.03-7.09, 7.34-7.38, 7.45, 7.60-7.63.

Example 13(7): 3-[2-[(E,3R)-5-[3-(Benzenesulfonamido)-5-fluorophenyl]-3-hydroxypent-4-enoxy]phenyl]propanoic acid HPLC retention time (min): 0.96;
$^1$H-NMR (CD$_3$OD): δ 1.92-1.98, 2.44-2.48, 2.78-2.82, 3.98, 4.06, 4.42, 6.17, 6.39, 6.68, 6.70-6.82, 7.03-7.08, 7.37-7.41, 7.47, 7.68-7.71.

Example 13(8): 3-[2-[(E,3R)-5-[3-(Benzenesulfonamido)-4-fluorophenyl]-3-hydroxypent-4-enoxy]phenyl]propanoic acid HPLC retention time (min): 0.92;
$^1$H-NMR (CD$_3$OD): δ 1.95-2.00, 2.45-2.49, 2.81-2.84, 4.00, 4.07, 4.44, 6.10, 6.45, 6.75, 6.81-6.86, 7.04-7.10, 7.34-7.39, 7.47, 7.64-7.66.

Example 13(9): 3-[2-[(E,3R)-5-[3-(Benzenesulfonamido)-2-(trifluoromethyl)phenyl]-3-hydroxypent-4-enoxy]phenyl]propanoic acid HPLC retention time (min): 0.95;
$^1$H-NMR (CD$_3$OD): δ 1.94-2.00, 2.43-2.47, 2.78-2.82, 3.99, 4.06, 4.45, 6.08, 6.74, 6.79-6.85, 7.03-7.10, 7.32-7.43, 7.50, 7.58-7.60.

Example 13(10) 3-[2-[(E,3R)-5-[5-(Benzenesulfonamido)-2-(trifluoromethyl)phenyl]-3-hydroxypent-4-enoxy]phenyl]propanoic acid HPLC retention time (min): 0.99;
$^1$H-NMR (CD$_3$OD): δ 1.94-2.00, 2.43-2.47, 2.79-2.83, 3.99, 4.07, 4.47, 6.09, 6.73-6.82, 7.04-7.08, 7.27, 7.38-7.42, 7.48, 7.73-7.76.

Example 13(11): 3-[2-[(E,3R)-5-[3-(Benzenesulfonamido)-5-(trifluoromethyl)phenyl]-3-hydroxypent-4-enoxy]phenyl]propanoic acid HPLC retention time (min): 0.99;
$^1$H-NMR (CD$_3$OD): δ 1.91-2.03, 2.42-2.46, 2.79-2.83, 3.99, 4.07, 4.46, 6.25, 6.49, 6.74, 6.81, 7.03-7.07, 7.16, 7.22-7.26, 7.37-7.41, 7.47, 7.67-7.70.

Example 13(12): 3-[2-[(E,3R)-5-[3-(Benzenesulfonamido)-4-(trifluoromethyl)phenyl]-3-hydroxypent-4-enoxy]phenyl]propanoic acid HPLC retention time (min): 0.97;
$^1$H-NMR (CD$_3$OD): δ 1.94-2.00, 2.46-2.50, 2.80-2.84, 4.00, 4.08, 4.46, 6.19, 6.49, 6.76, 6.84, 7.05-7.10, 7.24, 7.28, 7.39-7.52, 7.67-7.70.

Example 13(13): 3-[2-[(E,3R)-5-[6-(Benzenesulfonamido)pyridin-2-yl]-3-hydroxypent-4-enoxy]phenyl]propanoic Acid HPLC retention time (min): 0.85;
$^1$H-NMR (CD$_3$OD): δ 1.92-2.00, 2.45-2.49, 2.79-2.83, 3.96-4.10, 4.47, 6.42, 6.64, 6.75, 6.79-6.83, 6.88, 7.03-7.08, 7.36-7.49, 7.85-7.88.

Example 13(14): 3-[2-[(E,3R)-5-[1-(Benzenesulfonyl)-2,3-dihydroindol-6-yl]-3-hydroxypent-4-enoxy]phenyl]propanoic Acid HPLC retention time (min): 1.00;
$^1$H-NMR (CD$_3$OD): δ 2.11-2.16, 2.59-2.63, 2.82-2.86, 2.94-2.98, 3.94-3.98, 4.14, 4.22, 4.60, 6.34, 6.66, 6.87, 6.96, 7.05-7.09, 7.16-7.21, 7.48-7.52, 7.63, 7.66, 7.78-7.81.

Example 13(15): 3-[2-[(E,3R)-5-[1-(Benzenesulfonyl)-2,3-dihydroindol-4-yl]-3-hydroxypent-4-enoxy]phenyl]propanoic Acid HPLC retention time (min): 1.00;
$^1$H-NMR (CD$_3$OD): δ 2.04-2.09, 2.51-2.55, 2.70-2.89, 3.89-3.96, 4.08, 4.14, 4.53, 6.23, 6.50, 6.83, 6.90, 7.08-7.19, 7.48-7.53, 7.63, 7.78-7.81.

Example 13(16): 3-[2-[(E,3R)-5-[2-(Benzenesulfonyl)-1,3-dihydroisoindol-5-yl]-3-hydroxypent-4-enoxy]phenyl]Propanoic Acid HPLC retention time (min): 1.00;
$^1$H-NMR (CD$_3$OD): δ 2.06-2.10, 2.55-2.59, 2.89-2.93, 4.10, 4.17, 4.54, 4.60, 6.31, 6.60, 6.85, 6.92, 7.13-7.18, 7.28-7.30, 7.58-7.68, 7.90-7.93.

Example 13(17): 3-[2-[(E,3R)-5-[1-(Benzenesulfonyl)-3,4-dihydro-2H-quinolin-7-yl]-3-hydroxypent-4-enoxy]phenyl]propanoic Acid HPLC retention time (min): 1.00;
$^1$H-NMR (CD$_3$OD): δ 1.59-1.66, 2.10-2.15, 2.40-2.43, 2.59-2.63, 2.93-2.97, 3.82-3.85, 4.14, 4.21, 4.59, 6.31, 6.62, 6.86, 6.94-7.01, 7.16-7.21, 7.45-7.49, 7.59-7.63, 7.79.

Example 13(18): 3-[2-[(E,3R)-5-[1-(Benzenesulfonyl)-3,4-dihydro-2H-quinolin-5-yl]-3-hydroxypent-4-enoxy]phenyl]propanoic Acid HPLC retention time (min): 1.00;
$^1$H-NMR (CD$_3$OD): δ 1.50-1.57, 2.01-2.15, 2.19-2.37, 2.53-2.57, 2.88-2.92, 3.75-3.78, 4.07, 4.16, 4.56, 6.12, 6.67, 6.84, 6.90, 7.13-7.21, 7.32, 7.45-7.49, 7.56-7.65.

Example 13(19): 3-[2-[(E,3R)-5-[2-(Benzenesulfonyl)-3,4-dihydro-1H-isoquinolin-7-yl]-3-hydroxypent-4-enoxy]phenyl]propanoic Acid HPLC retention time (min): 1.00;
$^1$H-NMR (CD$_3$OD): δ 2.07-2.12, 2.57-2.61, 2.87-2.95, 3.36-3.39, 4.11, 4.18, 4.25, 4.55, 6.29, 6.57, 6.85, 6.93, 7.05, 7.14-7.19, 7.23, 7.59-7.70, 7.87-7.89.

Example 14: N-(3-Bromophenyl)-N-(oxetan-2-ylmethyl)benzenesulfonamide

Oxetan-2-ylmethanol (132 mg), triphenylphosphine (394 mg) and diethyl azodicarboxylate (a 40% toluene solution, 0.68 mL) were added a solution of the compound produced in Example 9 (313 mg) in THF (2 mL), and the resultant solution was stirred at room temperature for 2 hours. The reaction solution was purified by silica gel column chromatography (hexane: ethyl acetate=4:1→1:1). In this manner, the title compound (381 mg) having the physical property value shown below was produced.
TLC: Rf 0.34 (hexane: ethyl acetate=2:1)

Example 15: 3-[2-[(E,3R)-5-[3-[Benzenesulfonyl(oxetan-2-ylmethyl)amino]phenyl]-3-hydroxypent-4-enoxy]phenyl]propanoic acid The same designed procedures as in Example 10→Example 11 were carried out using, in place of N-(3-bromophenyl)benzenesulfonamide used in Example 10, the compound produced in Example 14. In this manner, the title compound having the physical property values shown below was produced.
HPLC retention time (min): 0.95;
$^1$H-NMR (CD$_3$OD): δ 2.06-2.10, 2.48-2.69, 2.91-2.95, 3.80, 4.00, 4.10, 4.18, 4.47-4.64, 4.83, 6.21, 6.55, 6.87, 6.94-6.96, 7.03, 7.17-7.21, 7.27, 7.38, 7.50-7.54, 7.60-7.65.

Examples 16(1) to (8)

The same designed procedures as in Example 14→Example 10→Example 11 were carried out using corresponding alcohol compounds in place of oxetan-2-ylmethanol used in Example 14 and using corresponding halide compounds in place of N-(3-bromophenyl)benzenesulfonamide used in Example 10. In this manner, the following compounds of Examples were produced.

Example 16(1): 3-[2-[(E,3R)-5-[3-[Benzenesulfonyl(oxetan-3-ylmethyl)amino]phenyl]-3-hydroxypent-4-enoxy]phenyl]propanoic acid HPLC retention time (min): 0.94;
$^1$H-NMR (CD$_3$OD): δ 2.06-2.11, 2.57-2.61, 2.91-2.95, 3.04, 3.95, 4.10, 4.18, 4.36-4.40, 4.55, 4.63-4.67, 6.22, 6.55, 6.85-6.97, 7.16-7.21, 7.29, 7.40, 7.52-7.56, 7.62-7.67.

Example 16(2): 3-[2-[(E,3R)-5-[3-[Benzenesulfonyl(oxolan-2-ylmethyl)amino]phenyl]-3-hydroxypent-4-enoxy]phenyl]propanoic acid HPLC retention time (min): 1.00;
$^1$H-NMR (CD$_3$OD): δ 1.72, 1.84-1.99, 2.06-2.11, 2.57-2.61, 2.92-2.95, 3.57, 3.66-3.80, 3.89, 4.10, 4.18, 4.55, 6.22, 6.56, 6.87, 6.94-6.97, 7.05, 7.16-7.21, 7.28, 7.38, 7.49-7.53, 7.58-7.64.

Example 16(3): 3-[2-[(E,3R)-5-[3-[benzenesulfonyl(oxolan-3-ylmethyl)amino]phenyl]-3-hydroxypent-4-enoxy]phenyl]propanoic acid HPLC retention time (min): 0.97;
$^1$H-NMR (CD$_3$OD): δ 1.74, 1.95, 2.06-2.11, 2.25, 2.57-2.61, 2.91-2.95, 3.57-3.61, 3.67-3.73, 3.87, 4.10, 4.19, 4.55, 6.23, 6.56, 6.87, 6.94-6.96, 7.02, 7.16-7.21, 7.30, 7.41, 7.50-7.54, 7.57-7.65.

Example 16(4)

3-[2-[(E,3R)-5-[3-[Benzenesulfonyl(oxan-2-ylmethyl)amino]phenyl]-3-hydroxypent-4-enoxy]phenyl]propanoic acid HPLC retention time (min): 1.10;
$^1$H-NMR (CD$_3$OD): δ 1.26, 1.39-1.55, 1.68, 1.82, 2.06-2.11, 2.57-2.61, 2.92-2.95, 3.23-3.30, 3.51, 3.70, 3.87, 4.10, 4.18, 4.55, 6.20, 6.56, 6.87, 6.93-6.96, 7.02, 7.16-7.21, 7.28, 7.38, 7.49-7.53, 7.58-7.63.

Example 16(5): 3-[2-[(E,3R)-5-[3-[Benzenesulfonyl(propan-2-yl)amino]phenyl]-3-hydroxypent-4-enoxy]phenyl]propanoic acid TLC: Rf 0.31 (hexane: ethyl acetate=1:2);
$^1$H-NMR (CDCl$_3$): δ 1.04, 1.98-2.21, 2.67, 2.89-3.01, 4.10-4.24, 4.55-4.66, 6.22, 6.59, 6.85-6.92, 7.07, 7.16-7.28, 7.38-7.57, 7.76.

Example 16(6): 3-[2-[(E,3R)-5-[3-[Benzenesulfonyl(2-methylpropyl)amino]phenyl]-3-hydroxypent-4-enoxy]phenyl]propanoic acid TLC: Rf 0.34 (hexane: ethyl acetate=1:2);
$^1$H-NMR (CDCl$_3$): δ 0.91, 1.57, 2.08-2.15, 2.67, 2.97, 3.30, 4.10-4.24, 4.62, 6.20, 6.57, 6.83-6.92, 7.08, 7.16-7.25, 7.31, 7.40-7.47, 7.51-7.60.

Example 16(7): 3-[2-[(E,3R)-5-[3-[Benzenesulfonyl(cyclopropylmethyl)amino]phenyl]-3-hydroxypent-4-enoxy]phenyl]propanoic acid TLC: Rf 0.79 (ethyl acetate);
$^1$H-NMR (CDCl$_3$): δ 0.09-0.13, 0.38-0.43, 0.80-0.90, 2.09-2.18, 2.67, 2.97, 3.42, 4.11-4.23, 4.63, 6.22, 6.58, 6.86-6.93, 7.14-7.26, 7.33, 7.44, 7.55, 7.63.

Example 16(8): 3-[2-[(E,3R)-5-[3-[Benzenesulfonyl (2-phenylethyl)amino]phenyl]-3-hydroxypent-4-enoxy]phenyl]propanoic acid TLC: Rf 0.74 (ethyl acetate);
$^1$H-NMR (CDCl$_3$): δ 2.07-2.21, 2.64-2.71, 2.74-2.81, 2.94-3.01, 3.72-3.80, 4.11-4.24, 4.63, 6.22, 6.59, 6.81-6.93, 7.09-7.26, 7.31-7.45, 7.51-7.60.

Example 17: N-(3-Bromophenyl)-N-(2-oxopropyl) benzenesulfonamide

Sodium hydride (60% in mineral oil, 141 mg) was added to a solution of the compound produced in Example 9 (1.00 g) in DMF (6 mL) under ice cooling, and the resultant solution was stirred at room temperature. After 30 minutes, chloroacetone (0.52 mL) was added to the solution, and was then stirred at room temperature for 4 hours. Water was added to the reaction solution, and the resultant solution was extracted with ethyl acetate. An organic layer was washed with saturated saline, was then dried over magnesium sulfate, and was then concentrated under a reduced pressure. The resultant residue was purified by silica gel column chromatography (hexane: ethyl acetate=80:20→50:50). In this manner, the title compound (1.10 g) having the physical property value shown below was produced.
TLC: Rf 0.42 (hexane: ethyl acetate=2:1)

Example 18: N-(3-Bromophenyl)-N-(2-hydroxy-2-methylpropyl)benzenesulfonamide Methylmagnesium bromide (a 0.95-M THE solution, 1.0 mL) was added to a solution of the compound produced in Example 17 (313 mg) in THF (3 mL) under ice cooling, and the resultant solution was stirred at room temperature overnight. A saturated aqueous ammonium chloride solution was added to the reaction solution, and the resultant solution was extracted with ethyl acetate. An organic layer was washed with water and saturated saline, was then dried over magnesium sulfate, and was then concentrated under a reduced pressure. The resultant residue was purified by silica gel column chromatography (hexane: ethyl acetate=80:20→50:50). In this manner, the title compound (50 mg) having the physical property value shown below was produced.
TLC: Rf 0.58 (hexane: ethyl acetate=1:1).

Example 19: 3-[2-[(E,3R)-5-[3-[Benzenesulfonyl-(2-hydroxy-2-methylpropyl)amino]phenyl]-3-hydroxypent-4-enoxy]phenyl]propanoic acid The same designed procedures as in Example 10→Example 11 were carried out using, in place of N-(3-bromophenyl)benzenesulfonamide used in Example 10, the compound produced in Example 18. In this manner, the title compound having the physical property values shown below was produced.
HPLC retention time (min): 0.93;
$^1$H-NMR (CD$_3$OD): δ 1.18, 2.06-2.10, 2.58-2.62, 2.92-2.96, 3.66, 4.10, 4.18, 4.54, 6.20, 6.55, 6.87, 6.95, 6.99, 7.05, 7.17-7.21, 7.25, 7.35, 7.46-7.54, 7.60.

Examples 20(1) to (4) The same designed procedures as in Example 17→Example 10→Example 11 were carried out using corresponding halide compounds in place of chloroacetone used in Example 17 and using corresponding halide compounds in place of N-(3-bromophenyl)benzenesulfonamide used in Example 10. In this manner, the following compounds of Examples were produced.

Example 20(1): 3-[2-[(E,3R)-5-[3-[Benzenesulfonyl (methyl)amino]phenyl]-3-hydroxypent-4-enoxy] phenyl]propanoic acid HPLC retention time (min): 0.99;
$^1$H-NMR (CDCl$_3$): δ 2.06-2.11, 2.57-2.61, 2.91-2.95, 3.20, 4.10, 4.19, 4.55, 6.24, 6.57, 6.87, 6.93-7.00, 7.08, 7.17-7.20, 7.27, 7.36, 7.50-7.56, 7.63.

Example 20(2): 3-[2-[(E,3R)-5-[3-[Benzenesulfonyl (ethyl)amino]phenyl]-3-hydroxypent-4-enoxy]phenyl]propanoic acid HPLC retention time (min): 1.01;
$^1$H-NMR (CDCl$_3$): δ 1.07, 2.06-2.11, 2.57-2.61, 2.92-2.96, 3.66, 4.11, 4.19, 4.55, 6.22, 6.57, 6.87, 6.92-6.96, 7.01, 7.16-7.21, 7.29, 7.39, 7.50-7.54, 7.59-7.65.

Example 20(3): 3-[2-[(E,3R)-5-[3-[Benzenesulfonyl (benzyl)amino]phenyl]-3-hydroxypent-4-enoxy] phenyl]propanoic acid HPLC retention time (min): 1.07;
$^1$H-NMR (CDCl$_3$): δ 2.04-2.09, 2.57-2.61, 2.91-2.95, 4.08, 4.16, 4.52, 4.80, 6.14, 6.48, 6.85-6.89, 6.93-6.96, 7.14-7.28, 7.54-7.58, 7.63-7.69.

Example 20(4): 3-[2-[(E,3R)-5-[3-[Benzenesulfonyl (2,2,2-trifluoroethyl)amino]phenyl]-3-hydroxypent-4-enoxy]phenyl]propanoic Acid TLC: Rf 0.49 (hexane: ethyl acetate=1:2);
$^1$H-NMR (CDCl$_3$): δ 2.08-2.17, 2.62-2.70, 2.94-3.00, 4.11-4.26, 4.62, 6.21, 6.57, 6.83-6.93, 7.10, 7.17-7.25, 7.36, 7.47, 7.57-7.63.

Example 21: (R)-1-(3-Bromophenyl)-2-phenylethan-1-ol (R)-Methyloxazaborolidine (a 1.0-M toluene solution, 3.6 mL) and borane-dimethyl sulfide (a 2.0-M THF solution, 3.6 mL) were added to a solution of 1-(3-bromophenyl)-2-phenylethanone (CAS Registry Number: 40396-53-0) (2.00 g) in THF (70 mL) at −20° C., and the resultant solution was stirred at the same temperature for 1 hour. Methanol (1 mL) was added to the reaction solution at −20° C., and the resultant solution was concentrated under a reduced pressure. The resultant residue was purified by silica gel column chromatography (hexane: ethyl acetate=9:1→2:1). In this manner, the title compound (1.91 g, 96% ee) having the physical property value shown below was produced. The compound thus produced was analyzed by SFC (column used: Daicel Corporation, CHIRALPAK-IA (10 mm×250 mm), mobile phase: CO$_2$: acetonitrile: methanol=90:9:1, flow rate: 30 mL/min, pressure: 100 bar, wavelength: 220 nm, column temperature: 35° C.). As a result, the retention time was 5.6 minutes.
HPLC retention time (min): 1.08.

Example 22: Isopropyl 3-(2-(((R,E)-3-hydroxy-5-(3-((R)-1-hydroxy-2-phenylethyl)phenyl)pent-4-en-1-yl)oxy)phenyl)propanoate The same designed procedure as in Example 10 was carried out using, in place of N-(3-bromophenyl)benzenesulfonamide used in Example 10, the compound produced in Example 21. In this manner, the title compound having the physical property value shown below was produced.

HPLC retention time (min): 1.21.

Example 23: 3-[2-[(E,3R)-3-Hydroxy-5-[3-[(1R)-1-hydroxy-2-phenylethyl]phenyl]pent-4-enoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the compound produced in Example 22. In this manner, the title compound having the physical property values shown below was produced.

HPLC retention time (min): 0.95;
$^1$H-NMR (CD$_3$OD): δ 2.08-2.13, 2.58-2.62, 2.93-2.98, 3.06, 4.11, 4.19, 4.56, 4.84, 6.28, 6.62, 6.86, 6.94, 7.10-7.31.

Example 24: 3-[2-[(E,3R)-3-Hydroxy-5-[3-[(1S)-1-hydroxy-2-phenylethyl]phenyl]pent-4-enoxy]phenyl]propanoic acid The same designed procedures as in Example 21→Example 10→Example 11 were carried out using (S)-methyloxazaborolidine in place of (R)-methyloxazaborolidine used in Example 21 and using a corresponding halide compound in place of N-(3-bromophenyl)benzenesulfonamide used in Example 10. In this manner, the title compound having the physical property values shown below was produced.

HPLC retention time (min): 0.97;
$^1$H-NMR (CD$_3$OD): δ 2.08-2.13, 2.58-2.62, 2.93-2.98, 3.06, 4.11, 4.19, 4.56, 4.84, 6.27, 6.61, 6.86, 6.94, 7.10-7.31.

Example 25: 3-[2-[(E,3R)-3-Hydroxy-5-[3-[(2R)-2-hydroxy-2-phenylethyl]phenyl]pent-4-enoxy]phenyl]propanoic acid The same designed procedures as in Example 21→Example 10→Example 11 were carried out using 2-(3-bromophenyl)-1-phenylethanone (CAS Registry Number: 27798-44-3) in place of 1-(3-bromophenyl)-2-phenylethanone used in Example 21 and using a corresponding halide compound in place of N-(3-bromophenyl)benzenesulfonamide used in Example 10. In this manner, the title compound having the physical property values shown below was produced.

HPLC retention time (min): 0.99;
$^1$H-NMR (CDCl$_3$): δ 2.10-2.15, 2.64-2.68, 2.94-3.05, 4.10-4.21, 4.59-4.64, 4.92, 6.27, 6.61, 6.86-6.91, 7.05-7.24, 7.27-7.37.

Example 26: 3-[2-[(E,3R)-3-Hydroxy-5-[3-[(2S)-2-hydroxy-2-phenylethyl]phenyl]pent-4-enoxy]phenyl]propanoic acid The same designed procedure as in Example 25 was carried out using (S)-methyloxazaborolidine in place of (R)-methyloxazaborolidine used in Example 25 and using a corresponding halide compound in place of N-(3-bromophenyl)benzenesulfonamide used in Example 10. In this manner, the title compound having the physical property values shown below was produced.

HPLC retention time (min): 0.98;
$^1$H-NMR (CDCl$_3$): δ 2.10-2.15, 2.63-2.67, 2.94-3.05, 4.10-4.22, 4.59-4.64, 4.91, 6.27, 6.61, 6.86-6.91, 7.06-7.08, 7.14-7.24, 7.28-7.38.

Example 27: 1-(3-Bromophenyl)-3-phenylpropan-1-ol

A solution of 3-bromobenzaldehyde (500 mg) in THF (13.5 mL) was cooled to 0° C., phenylmagnesium chloride (a 1.0-M THF solution, 3.5 mL) was added to the solution, and the resultant reaction mixture was stirred at 0° C. for 30 minutes. The reaction mixture was poured into a saturated ammonium chloride solution, and the resultant solution was extracted with methyl-tert-butyl ether. An organic layer was washed with saturated saline, was then dried over sodium sulfate, and was then concentrated under a reduced pressure. The resultant residue was purified by silica gel column chromatography (hexane: ethyl acetate=10:0→2:1). In this manner, the title compound (610 mg) having the physical property values shown below was produced.

$^1$H-NMR (CDCl$_3$): δ 1.85, 1.98-2.15, 2.65-2.80, 4.65-4.69, 7.18-7.31, 7.39-7.42, 7.51.

Example 28: 3-[2-[(E,3R)-3-Hydroxy-5-[3-(1-hydroxy-3-phenylpropyl)phenyl]pent-4-enoxy]phenyl]propanoic acid The same designed procedure as in Example 10→Example 11 were carried out using, in place of N-(3-bromophenyl)benzenesulfonamide used in Example 10, the compound produced in Example 27. In this manner, the title compound having the physical property values shown below was produced.

HPLC retention time (min): 1.00;
$^1$H-NMR (CD$_3$OD): δ 1.82-2.03, 2.36-2.40, 2.47-2.63, 2.81-2.85, 3.96-4.09, 4.46-4.51, 6.22, 6.54, 6.69-6.79, 6.98-7.29.

Example 29: 1-(3-Bromophenyl)-2-methyl-2-phenylpropan-1-ol

Potassium hydroxide (179 mg), 18-crown-6-ether (4 mg) and methyl iodide (0.29 mL) were added to a solution of 1-(3-bromophenyl)-2-phenyl-ethanone (CAS Registry Number: 40396-53-0) (220 mg) in toluene (0.4 mL), and the resultant reaction mixture was stirred at 70° C. for 4 hours. Water was added to the reaction mixture, and the resultant solution was extracted with 2-methoxy-2-methylpropane. An organic layer was dried over sodium sulfate, and was then concentrated under a reduced pressure. Sodium borohydride (61 mg) was added to a solution of the resultant residue in methanol (1.5 mL), and the resultant reaction mixture was stirred at room temperature for 1 hour. Water was added to the reaction mixture, and was then extracted with ethyl acetate. An organic layer was dried over sodium sulfate, and was then concentrated under a reduced pressure. The resultant residue was purified by silica gel column chromatography (hexane: ethyl acetate=9:1). In this manner, the title compound (129 mg) having the physical property value shown below was produced.

HPLC retention time (min): 1.15 (conditioned).

Example 30: 3-[2-[(E,3R)-3-Hydroxy-5-[3-(1-hydroxy-2-methyl-2-phenylpropyl)phenyl]pent-4-enoxy]phenyl]propanoic acid The same designed procedures as in Example 10→Example 11 were carried out using, in place of N-(3- bromophenyl)benzenesulfonamide used in Example 10, the compound produced in Example 29. In this manner, the title compound having the physical property values shown below was produced.

HPLC retention time (min): 1.10;

$^1$H-NMR (CDCl$_3$): δ 2.08-2.13, 2.64-2.68, 2.94-2.97, 4.08-4.21, 4.59, 4.75, 6.15, 6.56, 6.86-6.91, 6.97-7.00, 7.09, 7.15-7.25, 7.30-7.38.

Example 31: 3-[2-[(E,3R)-5-[3-(Benzenesulfonamido)phenyl]-3-hydroxypent-4-enoxy]phenyl]propanamide Triethylamine (0.021 mL) and isobutyl chloroformate (0.016 mL) were added to a solution of the compound produced in Example 11 (50 mg) in THE (1 mL) under ice cooling, and the reaction mixture was stirred at 0° C. for 10 minutes. Ammonia (a 0.5-M 1,4-dioxane solution, 0.4 mL) was added to the solution at 0° C., and the resultant solution was stirred at room temperature for 30 minutes. The reaction mixture was concentrated under a reduced pressure, and the resultant residue was purified by silica gel column chromatography (hexane: ethyl acetate=1:1→0:1). In this manner, the title compound (38 mg) having the physical property values shown below was produced.

HPLC retention time (min): 0.88;

$^1$H-NMR (CDCl$_3$): δ 2.09-2.21, 2.54-2.63, 3.01, 4.13-4.23, 4.59, 5.70, 6.36, 6.54, 6.87-6.94, 7.00-7.22, 7.40-7.53, 7.79-7.82, 7.93.

Examples 32(1) to (3)

The same designed procedure as in Example 31 was carried out using, in place of ammonia used in Example 31, corresponding amine compounds. In this manner, the following compounds of Examples were produced.

Example 32(1): N-[3-[(E,3R)-3-Hydroxy-5-[2-(3-morpholin-4-yl-3-oxopropyl)phenoxy]pent-1-enyl]phenyl]benzenesulfonamide HPLC retention time (min): 0.94;

$^1$H-NMR (CDCl$_3$): δ 2.09-2.19, 2.60-2.65, 2.92-2.99, 3.41, 3.50-3.70, 4.09-4.23, 4.57, 6.30, 6.52, 6.85-6.91, 7.02-7.20, 7.40-7.56, 7.78-7.81.

Example 32(2): 3-[2-[(E,3R)-5-[3-(Benzenesulfonamido)phenyl]-3-hydroxypent-4-enoxy]phenyl]-N,N-dimethylpropanamide HPLC retention time (min): 0.95;

$^1$H-NMR (CDCl$_3$): δ 2.09-2.19, 2.60-2.65, 2.86-3.03, 4.09-4.22, 4.55, 6.33, 6.51, 6.84-6.91, 6.98-7.00, 7.12-7.20, 7.23-7.26, 7.40-7.52, 7.78-7.83, 7.98.

Example 32(3): 3-[2-[(E,3R)-5-[3-(Benzenesulfonamido)phenyl]-3-hydroxypent-4-enoxy]phenyl]-N-methylpropanamide HPLC retention time (min): 0.90;

$^1$H-NMR (CDCl$_3$): δ 2.07-2.19, 2.41-2.53, 2.82, 2.93-2.97, 4.10-4.22, 4.60, 5.58, 6.31, 6.54, 6.86-6.90, 7.02-7.20, 7.40-7.54, 7.78.

Example 33: 3-[2-[(3S)-5-[3-(Benzenesulfonamido)phenyl]-3-hydroxypentoxy]phenyl]propanoic acid

[Formula 46]

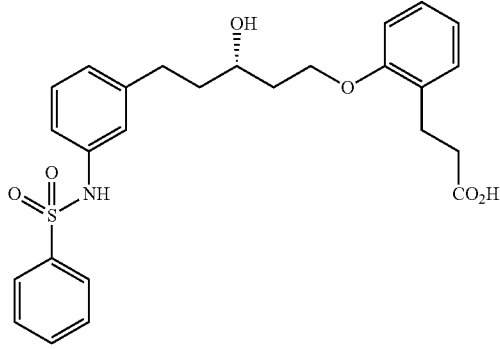

5% Palladium-carbon (200 mg) was added to a solution of the compound produced in Example 11 (1.1 g) in methanol (10 mL), and the resultant solution was stirred at room temperature for 1 hour under a hydrogen atmosphere. The reaction solution was filtrated, then a filtrate was concentrated under a reduced pressure, and the resultant residue was purified by silica gel column chromatography (hexane: ethyl acetate=70:30→ethyl acetate: methanol=95:5). In this manner, the title compound (1.05 g) having the physical property values shown below was produced.

TLC: Rf 0.30 (hexane: ethyl acetate=1:2);

$^1$H-NMR (CDCl$_3$): δ 1.69-2.02, 2.59-2.75, 2.90-2.96, 3.89, 4.05-4.18, 6.85-7.00, 7.11-7.22, 7.36-7.43, 7.44-7.53, 7.76.

Example 34: 3-[2-[(3S)-5-[3-(Benzylamino)phenyl]-3-hydroxypentoxy]phenyl]propanoic acid The same designed procedure as in Example 33 was carried out using the compound produced in Example 12(6) in place of 3-[2-[(E,3R)-5-[3-(benzenesulfonamido)phenyl]-3-hydroxypent-4-enoxy]phenyl]propanoic acid used in Example 33. In this manner, the following compound of Example were produced.

HPLC retention time (min): 0.81;

$^1$H-NMR (CD$_3$OD): δ 1.74-1.90, 2.00, 2.51-2.55, 2.59, 2.70, 2.85-2.89, 3.85, 4.07-4.16, 4.31, 6.47-6.56, 6.85, 6.92, 7.00, 7.13-7.23, 7.28-7.32, 7.36-7.38.

Example 35: Isopropyl 3-(2-(((S)-3-hydroxy-5-(3-((R)-1-hydroxy-2-phenylethyl)phenyl)pentyl)oxy)phenyl)propanoate p-Toluenesulfonyl hydrazide (2.66 g) and sodium acetate (1.17 g) were added to a solution of the compound produced in Example 22 (782 mg) in THE (10 mL) at room temperature, and the resultant solution was stirred at 80° C. for 19 hours. The reaction solution was cooled to room temperature, water was then added to the solution, and the resultant solution was extracted with ethyl acetate. An organic layer was dried over sodium sulfate, and was then concentrated under a reduced pressure. The resultant residue was purified by silica gel column chromatography (hexane: ethyl acetate=7:3→1:1). In this manner, the title compound (515 mg) having the physical property value shown below was produced.

HPLC retention time (min): 1.22.

Example 36: 3-[2-[(3S)-3-Hydroxy-5-[3-[(1R)-1-hydroxy-2-phenylethyl]phenyl]pentoxy]phenyl]propanoic acid

[Formula 47]

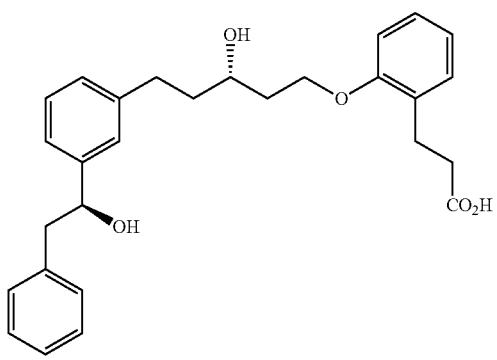

The same designed procedure as in Example 11 was carried out using the compound produced in Example 35 in place of propan-2-yl 3-[2-[(E,3R)-5-[3-(benzenesulfonamido)phenyl]-3-hydroxypent-4-enoxy]phenyl]propanoate used in Example 11. In this manner, the title compound having the physical property values shown below was produced.

HPLC retention time (min): 0.99;

$^1$H-NMR (CD$_3$OD): δ 1.74-1.81, 1.89, 2.02, 2.52-2.56, 2.66, 2.79, 2.86-2.90, 2.94, 3.05, 3.86, 4.08-4.19, 4.82, 6.85, 6.94, 7.08-7.23.

Example 37: 3-[2-[(3S)-3-Hydroxy-5-[3-[(1S)-1-hydroxy-2-phenylethyl]phenyl]pentoxy]phenyl]propanoic acid

[Formula 48]

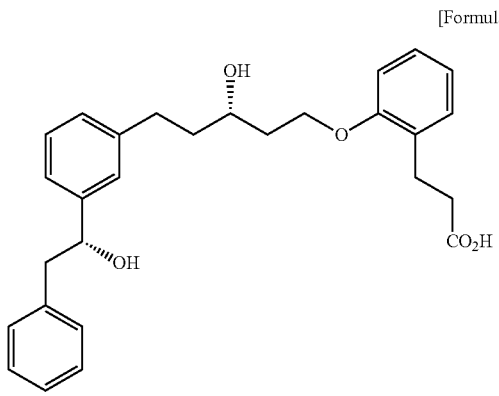

The same designed procedures as in Example 21→Example 10→Example 35→Example 11 were carried out using (S)-methyloxazaborolidine in place of (R)-methyloxazaborolidine used in Example 21 and using a corresponding halide compound in place of N-(3-bromophenyl)benzenesulfonamide used in Example 10. In this manner, the title compound having the physical property values shown below was produced.

HPLC retention time (min): 0.99;

$^1$H-NMR (CD$_3$OD): δ 1.74-1.81, 1.89, 2.02, 2.52-2.56, 2.66, 2.79, 2.86-2.90, 2.94, 3.05, 3.86, 4.08-4.19, 4.81, 6.85, 6.94, 7.08-7.23.

Example 38: Isopropyl 3-(2-((3R)-3-hydroxy-3-(2-(3-(phenylsulfonamido)phenyl)cyclopropyl)propoxy)phenyl)propanoate A solution of the compound produced in Example 10 (50 mg) in dichloromethane (2 mL) was cooled to 0° C., diethylzinc (a 1-M hexane solution, 0.5 mL) was then added to the solution, and then diiodomethane (128 mg) reaction mixture was stirred at 0° C. for 1 hour and a half A saturated aqueous ammonium chloride solution was added to the solution at 0° C., and the resultant solution was stirred at room temperature for 5 minute. The reaction mixture was poured into water, the resultant solution was extracted with ethyl acetate, and an organic layer was washed with saturated saline, was then dried over sodium sulfate, and was then concentrated under a reduced pressure. The resultant residue was purified by silica gel column chromatography (hexane: ethyl acetate=10:0→2:1). In this manner, the title compound (15 mg) having the physical property value shown below was produced.

HPLC retention time (min): 1.10.

Example 39: 3-[2-[(3R)-3-[2-[3-(Benzenesulfonamido)phenyl]cyclopropyl]-3-hydroxypropoxy]phenyl]propanoic acid The same designed procedure as in Example 11 was carried out using the compound produced in Example 38 in place of propan-2-yl 3-[2-[(E,3R)-5-[3-(benzenesulfonamido)phenyl]-3-hydroxypent-4-enoxy]phenyl]propanoate used in Example 11. In this manner, the title compound having the physical property values shown below was produced.

HPLC retention time (min): 0.92;

$^1$H-NMR (CD$_3$OD): δ 0.85-0.92, 1.03-1.08, 1.72-1.75, 2.03-2.09, 2.57, 2.91, 4.06-4.15, 6.68-6.69, 6.73-6.75, 6.84-6.89, 7.06, 7.14-7.20, 7.44-7.57, 7.72-7.74.

Example 40:
5-((3-nitrobenzyl)sulfonyl)-1-phenyl-1H-tetrazole

A solution of 5-[(3-nitrobenzyl)thio]-1-phenyl-1H-tetrazole [J. Org. Chem. (2001), 80, pp. 11611-11617](8.50 g) in acetonitrile (150 mL) and ethanol (150 mL) was cooled to 0° C., and a solution of ammonium molybdate tetrahydrate (3.35 g) in an aqueous hydrogen peroxide solution (35%, 26 mL) was added dropwise to the resultant solution over 10 minutes. The resultant reaction mixture was stirred at 0° C. for 2 hours and then at room temperature for 2 hours and a half. The reaction solution was cooled to 0° C. again, and an aqueous sodium thiosulfate solution (1 M, 150 mL) was then added to the reaction solution slowly over 20 minutes. The resultant solution was concentrated under a reduced pressure, the residue was extracted with ethyl acetate, and an organic layer was washed with saturated saline, was then dried over sodium sulfate, and was then concentrated under a reduced pressure. An oily product thus produced was suspended in a mixed solvent composed of hexane and ethyl acetate, and a blue solid material was filtrated out. The solid material was dissolved in dichloromethane to produce a solid material, and the solid material was filtrated out, and a filtrate was concentrated under a reduced pressure. In this manner, the title compound (7.71 g) having the physical property values shown below was produced.

$^1$H-NMR (CDCl$_3$): δ 5.12, 7.46-7.64, 7.82, 8.27, 8.35.

Example 41: (R)-1-((tert-Butyldimethylsilyl)oxy)-4-((4-methoxybenzil)oxy)butan-2-ol DMAP (0.73 g) and imidazole (6.08 g) were added to a solution of (R)-4-[(4-methoxybenzil)oxy]butan-1,2-diol (CAS Registry Number: 213978-61-1) (13.5 g) in DMF (300 mL), and the resultant reaction mixture was stirred at 0° C. for 5 minutes. Chloro-tert-butyl-dimethylsilane (8.93 g) was added to the solution, and the resultant solution was stirred at room temperature overnight. Ethyl acetate was added to the reaction solution to diluted the reaction solution, and an organic layer was washed with a saturated aqueous ammonium chloride solution and saturated saline, was dried over sodium sulfate, and was then concentrated under a reduced pressure. In this manner, the title compound (18.1 g) having the physical property values shown below was produced.

$^1$H-NMR (CDCl$_3$): δ 0.02, 0.83, 1.65-1.71, 2.73, 3.62-3.41, 3.74, 3.74-3.76, 4.39, 6.82, 7.18-7.21.

Example 42: (R)-1-((tert-Butyldimethylsilyl)oxy)-4-((4-methoxybenzil)oxy)butan-2-yl benzoate A solution of the compound produced in Example 41 (5.60 g) and pyridine (27 mL) in dichloromethane (55 mL) was cooled to 0° C., and N,N-diisopropylethylamine (27 mL) and DMAP (0.2 g) were then added to the solution. Benzyl chloride (2.5 mL) was added to the resultant reaction solution, the solution was stirred at room temperature overnight, and was then concentrated under a reduced pressure. The resultant residue was poured into ethyl acetate, an organic layer was then washed with 1-M hydrochloric acid and saturated aqueous sodium hydrogen carbonate, was then dried over sodium sulfate, and was then concentrated under a reduced pressure. The resultant residue was purified by silica gel column chromatography (hexane: ethyl acetate=10:0→7:3). In this manner, the title compound (6.31 g) having the physical property values shown below was produced.

$^1$H-NMR (CDCl$_3$): δ 0.00, 0.01, 0.85, 2.02-2.08, 3.53-3.57, 3.76, 3.79, 4.40, 5.27-5.30, 6.81, 7.21, 7.42, 7.53-7.56, 8.01.

Example 43: (R)-1-hydroxy-4-((4-methoxybenzil)oxy)butan-2-yl benzoate

A solution of the compound produced in Example 42 (6.31 g) in THE (170 mL) was cooled to 0° C., acetic acid (3.6 mL) and tetrabutylammonium fluoride (a 1.0-M THE solution, 21.2 mL) were added to the solution, and the resultant solution was stirred at room temperature overnight. The resultant residue was poured into ethyl acetate, an organic layer was washed with saturated aqueous ammonia and saturated aqueous sodium hydrogen carbonate, was then dried over sodium sulfate, and was then concentrated under a reduced pressure. The resultant residue was purified by silica gel column chromatography (hexane: ethyl acetate=10:0→1:1). In this manner, the title compound (4.10 g) having the physical property values shown below was produced.

$^1$H-NMR (CDCl$_3$): δ 2.06-2.09, 2.57, 3.54-3.65, 3.78, 3.80-3.86, 4.41-4.46, 5.27-5.30, 6.84, 7.23, 7.43, 7.56, 8.02.

Example 44: (R)-4-((4-Methoxybenzil)oxy)-1-oxobutan-2-yl benzoate

Pyridinium dichromate (10.6 g) and Molecular Sieve (trade name) (21.7 g) were suspended in dichloromethane (30 mL), and a solution of the compound produced in Example 43 (3.1 g) in dichloromethane (100 mL) was added dropwise to the resultant solution. The resultant solution was stirred at room temperature for 2 hours and a half and was then diluted with diethyl ether, and the resultant solution was filtrated. A filtrate was concentrated under a reduced pressure. In this manner, the title compound having the physical property values shown below was produced.

$^1$H-NMR (CDCl$_3$): δ 2.27-2.40, 3.57-3.70, 3.76, 4.43, 5.40, 6.82, 7.15-7.24, 7.45, 7.60, 8.03, 9.64.

Example 45: (R,E)-5-((4-Methoxybenzil)oxy)-1-(3-nitrophenyl)pent-1-en-3-yl benzoate A solution of the compound produced in Example 40 (3.56 g) in THE (70 mL) was cooled to −70° C., and potassium hexamethyldisilazide (a 0.5-M toluene solution, 22.5 mL) was added to the solution. The resultant reaction solution was stirred at −70° C. for 30 minutes, a solution of the compound produced in Example 44 (3.09 g) in THE (20 mL) was then added dropwise to the reaction solution over 5 minutes, and the reaction solution was then stirred at room temperature overnight. Ethyl acetate was added to the reaction solution to dilute the reaction solution, an organic layer was washed with saturated saline, was then dried over sodium sulfate, and was then concentrated under a reduced pressure, and the resultant residue was purified by silica gel column chromatography (hexane: ethyl acetate=10:0→1:1). In this manner, the title compound (2.23 g) having the physical property values shown below was produced.

$^1$H-NMR (CDCl$_3$): δ 2.11-2.24, 3.60, 3.75, 6.81, 7.22, 7.43-7.47, 7.56-7.63, 8.04-8.09, 8.21.

Example 46: (R,E)-5-Hydroxy-1-(3-nitrophenyl)pent-1-en-3-yl benzoate or (S,E)-5-hydroxy-1-(3-nitrophenyl)pent-1-en-3-yl benzoate 2,3-Dichloro-5,6-dicyano-1,4-benzoquinone (2.26 g) was added to a solution of the compound produced in Example 45 (2.23 g) in dichloromethane (100 mL) and a phosphate buffer (pH7,100 mL) at room temperature, and the resultant solution was stirred vigorously at room temperature for 3 hours and a half. The reaction mixture was poured into ethyl acetate, and an organic layer was then washed with saturated saline, was then dried over sodium sulfate, and was then concentrated under a reduced pressure. The resultant residue was purified by silica gel column chromatography (hexane: ethyl acetate=10:0→1:4) to produce a mixture of the title compounds (1.25 g). The resultant mixture was subjected to optical resolution employing SFC (column used: Daicel Corporation, CHIRALPAK-IA (20 mm×250 mm), mobile phase: CO$_2$: methanol=90:10, flow rate: 100 mL/min, pressure: 120 bar, wavelength: 254 nm, column temperature: 35° C.). Optically active substances produced under the optical resolution conditions were analyzed by SFC (column used: Daicel Corporation, CHIRALPAK-IA (10 mm×250 mm), mobile phase: CO$_2$: methanol=75:22.5:2.5, flow rate: 30 mL/min, pressure: 100 bar, wavelength: 220 nm, column temperature: 35° C.). As a result, the retention times for (R,E)-5-hydroxy-1-(3-nitrophenyl)pent-1-en-3-yl benzoate and (S,E)-5-hydroxy-1-(3-nitrophenyl)pent-1-en-3-yl benzoate were 5.4 minutes and 8.5 minutes, respectively.

¹H-NMR (CDCl₃): δ 2.04, 2.10-2.14, 3.77-3.82, 5.92-5.95, 6.47, 6.79, 7.46-7.51, 7.60, 7.68, 8.08-8.12, 8.26.

Example 47: Methyl 2-(2-hydroxyphenyl)-2-methylpropanoate

Lithium diisopropylamide (a 2.0-M THE solution, 18 mL) was added to a solution of methyl 2-(2-hydroxyphenyl) acetate (CAS Registry Number: 22446-37-3) (1.5 g) in THE (120 mL) at −78° C., the resultant solution was stirred at the same temperature for 1.5 hours. Methyl iodide (5.2 g) was added to the reaction solution at −78° C., the resultant solution was stirred at room temperature for 30 minutes. Water (40 mL) and acetic acid (1 mL) were added to the reaction solution, and the resultant solution was extracted with ethyl acetate. An organic layer was washed with saturated saline, was dried over sodium sulfate, and was then concentrated under a reduced pressure. The resultant residue (1.8 g) was dissolved in THF (150 mL), lithium diisopropylamide (a 2.0-M THE solution, 10 mL) was then added to the solution −78° C., and the resultant solution was stirred at the same temperature for 1.5 hours. Methyl iodide (2.85 g) was added to the reaction solution at −78° C., and the resultant solution was stirred at room temperature for 30 minutes. Water (40 mL) and acetic acid (1 mL) were added to the reaction solution, and the resultant solution was extracted with ethyl acetate. An organic layer was washed with a saturated aqueous sodium bicarbonate solution and saturated saline, was then dried over sodium sulfate, and was then concentrated under a reduced pressure. The resultant residue was purified by silica gel column chromatography (petroleum ether: ethyl acetate=7:1). In this manner, the title compound (538 mg) having the physical property values shown below was produced.
¹H-NMR (DMSO-d6): δ 1.42, 3.51, 6.70-6.83, 7.05, 7.19, 9.49.

Example 48: Methyl 1-(2-hydroxybenzil)cyclopropane-1-carboxylate

Sodium bis(trimethylsilyl)amide (a 1.0-M THE solution, 75 mL) was added to a solution of cyclopropylcarbonitrile (CAS Registry Number: 5500-21-0) (3.35 g) in THE (50 mL) at room temperature, and the resultant solution was stirred for 20 minutes. 1-(Chloromethyl)-2-methoxybenzene (CAS Registry Number: 7035-02-1) (7.83 g) was added to the reaction solution at room temperature, and the resultant solution was stirred for 3 hours under heating to reflux. The solution was cooled to room temperature, a saturated aqueous ammonium chloride solution was added to the reaction solution, and the resultant solution was extracted with ethyl acetate. An organic layer was dried over sodium sulfate, and was then concentrated under a reduced pressure. The resultant residue was purified by silica gel column chromatography (petroleum ether: ethyl acetate=10:1) to produce a crude product (6.00 g) of a nitrile compound. Conc. sulfuric acid (20 mL) was added to a solution of the crude product (4.50 g) of the nitrile compound in methanol (50 mL) at room temperature, and the resultant solution was stirred for 5 hours under heating to reflux. The reaction solution was cooled to room temperature, and was then concentrated under a reduced pressure. Ice-cooled water was added to the resultant residue, and the resultant solution was extracted with ethyl acetate. An organic layer was dried over sodium sulfate, and was then concentrated under a reduced pressure to produce a crude product (3.20 g) of an ester compound. Boron tribromide (a 1.0-M dichloromethane solution, 18.2 mL) was added dropwise to a solution of the crude product (2.00 g) of the ester compound in dichloromethane (30 mL) at −10° C., and the resultant solution was stirred at room temperature for 1 hour. The reaction solution was concentrated under a reduced pressure, and the resultant residue was preparatively purified by high-performance liquid chromatography (mobile phase A (a 0.1% aqueous solution of trifluoroacetic acid (abbreviated as "TFA", hereinafter)): mobile phase B (0.1% TFA/acetonitrile)=95:5→5:95). In this manner, the title compound (550 mg) having the physical property values shown below was produced.
¹H-NMR (CDCl₃): δ 1.11, 1.39, 2.90, 3.67, 6.87, 6.99, 7.18, 8.45.

Example 49: Methyl 4-(2-hydroxyphenyl)-2,2-dimethylbutanoate

A lithium diisopropylamide solution (a 2.0-M THE solution, 22.5 mL) was added to a solution of methyl 4-(2-hydroxyphenyl)butanoate (CAS Registry Number: 93108-07-7) (3.00 g) in THE (150 mL) −78° C., and the resultant solution was stirred at the same temperature for 30 minutes. Methyl iodide (6.3 g) was added to the reaction solution at −78° C., the resultant solution was stirred at room temperature for 2 hours. A saturated aqueous ammonium chloride solution was added to the reaction solution, and the resultant solution was extracted with ethyl acetate. An organic layer was dried over sodium sulfate, and was then concentrated under a reduced pressure. The resultant residue was preparatively purified by high-performance liquid chromatography (mobile phase A (a 0.1% aqueous TFA solution): mobile phase B (0.1% TFA/acetonitrile)=95:5→5:95). In this manner, the title compound (538 mg) having the physical property values shown below was produced.
¹H-NMR (DMSO-d6): δ 1.17, 1.67-1.73, 2.38-2.43, 3.59, 6.66-6.76, 6.95-7.00, 9.19.

Example 50: Methyl 1-(2-methoxyphenethyl)cyclopropane-1-carboxylate

Zinc (18.2 g) was added to a solution of bis(cyclopentadienyl)titanium(IV) dichloride (CAS Registry Number: 1271-19-8) (34.6 g) in THE (200 mL) at room temperature, and the resultant solution was stirred at the same temperature for 1 hour. A solution of methyl 2-(1-acetoxymethyl)-2-propenoate (CAS Registry Number: 30982-08-2) (11.0 g) and 1-(chloromethyl)-2-methoxybenzene (CAS Registry Number: 7035-02-1) (10.9 g) in THE (200 mL) was added to the reaction solution at room temperature, the resultant solution was stirred at the same temperature overnight. Water was added to the reaction solution, and the resultant solution was extracted with diethyl ether. An organic layer was dried over sodium sulfate, and was then concentrated under a reduced pressure. The resultant residue was purified by silica gel column chromatography (petroleum ether: ethyl acetate=5:1→2:1) to produce a crude product (13.0 g) of an ester compound. Palladium (II) acetate and diazomethane (a 0.5-M diethyl ether solution, 32.6 mL) were added to a solution of the crude product of the ester compound (3.00 g) in diethyl ether (100 mL) under ice cooling, and the resultant solution was stirred at room temperature for 4 hours. Acetic acid (4 mL) and water were added to the reaction solution, and the resultant solution was extracted with diethyl ether. An organic layer was dried over sodium sulfate, and was then concentrated under a reduced pressure. In this manner, the title compound (3.00 g) having the physical property values shown below was produced.

Example 51: Methyl 1-(2-hydroxyphenethyl)cyclopropane-1-carboxylate

Boron tribromide (a 1.0-M dichloromethane solution, 38.4 mL) was added dropwise to a solution of the compound produced in Example 50 (3.00 g) in dichloromethane (100 mL) −78° C., and the resultant solution was stirred at the same temperature for 5 hours. Methanol (30 mL) and water were added to the reaction solution, and the resultant solution was extracted with dichloromethane. An organic layer was dried over sodium sulfate, and was then concentrated under a reduced pressure. The resultant residue was preparatively purified by high-performance liquid chromatography (mobile phase A (a 0.5% aqueous ammonium hydrogen carbonate solution): mobile phase B (acetonitrile)=80:20→25:75). In this manner, the title compound (515 mg) having the physical property values shown below was produced.

$^1$H-NMR (DMSO-d6): δ 0.73, 1.06, 1.67-1.79, 2.58-2.70, 3.58, 6.63-6.80, 6.95-7.01, 9.17.

Example 52: Ethyl (E)-3-(2-(benziloxy)-5-fluorophenyl)acrylate

A solution prepared by suspending sodium hydride (60% in mineral oil, 1.80 g) in DMF (30 mL) was cooled to 0° C. Triethyl phosphonoacetate (10.0 g) was added to the solution, and the resultant solution was stirred at 0° C. for 30 minutes, and a solution of 2-benziloxy-5-fluoro-benzaldehyde (CAS Registry Number: 312314-37-7) (8.70 g) in DMF (10 mL) was added dropwise to the solution, and the resultant solution was stirred at 0° C. for 1 hour. The reaction mixed solution was poured into ice-cold water, and the resultant solution was extracted with ethyl acetate. An organic layer was washed with water and saturated saline, was then dried over sodium sulfate, and was then concentrated under a reduced pressure. In this manner, the title compound (13.2 g) having the physical property values shown below was produced.

$^1$H-NMR (CDCl$_3$): δ 1.33, 4.24, 5.13, 6.47, 6.85-7.00, 7.21-7.41, 7.99-8.05.

Example 53: Ethyl 3-(5-fluoro-2-hydroxyphenyl)propanoate

Palladium carbon (1.95 g) was added to a solution of the compound produced in Example 52 (11.0 g) in ethanol (18 mL), and the resultant solution was stirred at room temperature for 3 hours under a hydrogen atmosphere. The reaction solution was filtrated through Celite (trade name), and a filtrate was concentrated under a reduced pressure. The resultant residue was purified by silica gel column chromatography (hexane: ethyl acetate=4:1→2:1). In this manner, the title compound (5.8 g) having the physical property values shown below was produced.

$^1$H-NMR (CDCl$_3$): δ 1.24, 2.71, 2.86, 4.15, 6.77-6.83, 7.23.

Example 54: (R,E)-5-(2-((E)-3-Methoxy-3-oxoprop-1-en-1-yl)phenoxy)-1-(3-nitrophenyl)pent-1-en-3-yl benzoate Diisopropyl azodicarboxylate (abbreviated as "DIAD", hereinafter) (0.1 mL) was added to a solution of (R,E)-5-hydroxy-1-(3-nitrophenyl)pent-1-en-3-yl benzoate (110 mg) produced in Example 46, methyl (E)-3-(2-hydroxyphenyl)prop-2-enoate (CAS Registry Number: 6236-69-7) (90 mg) and triphenylphosphine (130 mg) in THF (1 mL), and the resultant solution was stirred at room temperature overnight. The solution was concentrated under a reduced pressure, and the resultant residue was purified by silica gel column chromatography (hexane: ethyl acetate=10:0→1:2). In this manner, the title compound (200 mg) having the physical property values shown below was produced.

$^1$H-NMR (CDCl$_3$): δ 2.43-2.55, 3.78, 4.24, 5.94-5.98, 6.46-6.53, 6.82, 6.90, 6.96, 7.29-7.33, 7.44-7.51, 7.57-7.60, 7.68, 8.00, 8.07-8.10, 8.23-8.24.

Example 55: (R,E)-1-(3-Aminophenyl)-5-(2-((E)-3-methoxy-3-oxoprop-1-en-1-yl)phenoxy)pent-1-en-3-yl benzoate Tin (IV) chloride (310 mg) was added to a solution of the compound produced in Example 54 (160 mg) in ethanol (7 mL), and the resultant solution was stirred at 70° C. for 3 hours and a half. The reaction solution was cooled to room temperature and was then poured into ethyl acetate, and an organic layer was washed with a saturated aqueous sodium bicarbonate solution and saturated saline, was then dried over sodium sulfate, and was then concentrated under a reduced pressure. The resultant residue was purified by silica gel column chromatography (hexane: ethyl acetate=10:0→1:2). In this manner, the title compound (120 mg) having the physical property values shown below was produced.

$^1$H-NMR (CDCl$_3$): δ 2.39-2.52, 3.66, 3.79, 4.20, 5.90, 6.28, 6.53, 6.57-6.59, 6.68, 6.73, 6.79, 6.89, 6.94, 7.09, 7.28-7.32, 7.42-7.47, 7.49-7.50, 7.54-7.58, 8.01, 8.05-8.07.

Example 56: (R,E)-5-(2-((E)-3-Methoxy-3-oxoprop-1-en-1-yl)phenoxy)-1-(3-(phenylsulfonamido)phenyl)pent-1-en-3-yl benzoate A solution of the compound produced in Example 55 (60 mg) and pyridine (0.016 mL) in dichloromethane (1 mL) was cooled to 0° C., phenylsulfonyl chloride (0.018 mL) was then added to the resultant solution, and the resultant solution was stirred overnight while warming the solution to room temperature. 1 M hydrochloric acid and saturated saline were added to the reaction solution, and the resultant solution was extracted with ethyl acetate. An organic layer was washed with saturated saline, was then dried over sodium sulfate, and was then concentrated under a reduced pressure. The resultant residue was purified by silica gel column chromatography (hexane: ethyl acetate=10:0→1:1). In this manner, the title compound (62 mg) having the physical property values shown below was produced.

$^1$H-NMR (CDCl$_3$): δ 2.41-2.45, 3.87, 4.18-4.22, 5.84-5.88, 6.30-6.34, 6.51, 6.64, 6.89, 6.99, 7.05-7.19, 7.30-7.34, 7.38-7.50, 7.50-7.52, 7.56-7.59, 7.74-7.77, 8.04-8.07.

Example 57: (E)-3-[2-[(E,3R)-5-[3-(Benzenesulfonamido)phenyl]-3-hydroxypent-4-enoxy]phenyl] prop-2-enoic acid A 1-M aqueous lithium hydroxide solution (0.5 mL) was added to a solution of the compound produced in Example 56 (62 mg) in THF (1.5 mL) and methanol (0.5 mL), and the resultant solution was stirred at room temperature for 7 hours. 1 M hydrochloric acid and saturated saline were added to the reaction solution, and the resultant solution was extracted with ethyl acetate. An organic layer was washed with saturated saline, was then dried over sodium sulfate, and was then concentrated under a reduced pressure. The resultant residue was purified by silica gel column chromatography (dichloromethane: methanol=10:0→9:1). In this manner, the title compound (29 mg) having the physical property values shown below was produced.

HPLC retention time (min): 0.89;

¹H-NMR (DMSO-d6): δ 1.91-2.04, 4.10-4.22, 4.36, 5.12, 6.21-6.25, 6.44, 6.55, 6.93-6.99, 7.08-7.11, 7.16, 7.36-7.40, 7.52-7.55, 7.58-7.61, 7.66-7.68, 7.75-7.77, 7.85, 10.27, 12.31.

Example 58: N-[3-[(E,3R)-5-[2-(2-Cyanoethyl)phenoxy]-3-hydroxypent-1-enyl]phenyl]benzenesulfonamide The same designed procedures as in Example 54→Example 55→Example 56 were carried out using, in place of methyl (E)-3-(2-hydroxyphenyl)prop-2-enoate used in Example 54, a corresponding phenol compound. In this manner, the title compound having the physical property values shown below was produced.

HPLC retention time (min): 0.99;

¹H-NMR (CDCl₃): δ 2.07-2.19, 2.60-2.65, 2.89-3.00, 4.10-4.23, 4.58, 6.24, 6.44, 6.56, 6.89-6.95, 7.10-7.27, 7.42-7.46, 7.52-7.56, 7.75-7.78.

Example 59: Methyl 1-[2-[2-[(E,3R)-5-[3-(benzenesulfonamido)phenyl]-3-hydroxypent-4-enoxy]phenyl]ethyl]cyclopropane-1-carboxylate The same designed procedures as in Example 54→Example 55→Example 56 were carried out using, in place of methyl (E)-3-(2-hydroxyphenyl)prop-2-enoate used in Example 54, the phenol compound produced in Example 51. In this manner, the title compound having the physical property values shown below was produced.

HPLC retention time (min): 1.10;

¹H-NMR (CDCl₃): δ 0.71, 1.22, 1.79-1.83, 2.07-2.15, 2.44, 2.77-2.81, 3.65, 4.10-4.23, 6.24, 6.44, 6.55, 6.83-6.94, 7.08-7.20, 7.41-7.45, 7.51-7.55, 7.75-7.77.

Example 60: Methyl 4-[2-[(E,3R)-5-[3-(benzenesulfonamido)phenyl]-3-hydroxypent-4-enoxy]phenyl]-2,2-dimethylbutanoate The same designed procedures as in Example 54→Example 55→Example 56 were carried out using, in place of methyl (E)-3-(2-hydroxyphenyl)prop-2-enoate used in Example 54, the phenol compound produced in Example 49. In this manner, the title compound having the physical property values shown below was produced.

HPLC retention time (min): 1.10;

¹H-NMR (CDCl₃): δ 1.53, 1.56, 2.33-2.45, 3.63, 4.10-4.19, 5.95, 6.46, 6.71-6.91, 7.17-7.24, 7.45-7.52, 7.57-7.68.

Examples 61(1) to (8)

The same designed procedures as in Example 54→Example 55→Example 56→Example 57 were carried out using, in place of methyl (E)-3-(2-hydroxyphenyl)prop-2-enoate used in Example 54, corresponding phenol compounds. In this manner, the following compounds of Examples were produced.

Example 61(1): (E)-3-[4-[(E,3R)-5-[3-(Benzenesulfonamido)phenyl]-3-hydroxypent-4-enoxy]phenyl]prop-2-enoic acid HPLC retention time (min): 0.85;

¹H-NMR (DMSO-d6): δ 1.84-1.92, 4.06-4.17, 4.32-4.33, 5.07, 5.60-6.00, 6.10, 6.21, 6.37, 6.44, 6.94-6.97, 7.09-7.11, 7.16, 7.48-7.63, 7.75, 10.27, 12.15.

Example 61(2): 3-[4-[(E,3R)-5-[3-(Benzenesulfonamido)phenyl]-3-hydroxypent-4-enoxy]phenyl]propanoic acid HPLC retention time (min): 0.86;

¹H-NMR (DMSO-d6): δ 1.80-1.84, 1.87-1.96, 2.48, 2.74, 3.95-4.01, 4.01-4.08, 4.28-4.34, 5.04, 6.21, 6.43, 6.82-6.94, 6.93-6.96, 7.08-7.13, 7.17, 7.51-7.56, 7.57-7.59, 7.75-7.78, 10.27, 12.04.

Example 61(3): (E)-3-[3-[(E,3R)-5-[3-(Benzenesulfonamido)phenyl]-3-hydroxypent-4-enoxy]phenyl]prop-2-enoic acid HPLC retention time (min): 0.89;

¹H-NMR (DMSO-d6): δ 1.83-1.98, 4.06-4.17, 4.31-4.35, 5.06, 6.20-6.25, 6.44, 6.54, 6.94-6.99, 7.09-7.11, 7.17, 7.23-7.26, 7.31, 7.52-7.61, 7.75-7.77, 10.27, 12.35.

Example 61(4): 3-[3-[(E,3R)-5-[3-(Benzenesulfonamido)phenyl]-3-hydroxypent-4-enoxy]phenyl]propanoic acid HPLC retention time (min): 0.89;

¹H-NMR (DMSO-d6): δ 1.81-1.95, 2.51, 2.78, 4.31, 5.05, 6.21, 6.43, 6.73-6.79, 6.93-6.96, 7.09-7.10, 7.14-7.18, 7.52-7.55, 7.58-7.61, 7.75-7.78, 10.25, 12.10.

Example 61(5) 2-[3-[(E,3R)-5-[3-(Benzenesulfonamido)phenyl]-3-hydroxypent-4-enoxy]phenyl]-2-methylpropanoic acid HPLC retention time (min): 0.93;

¹H-NMR (DMSO-d6): δ 1.44, 1.81-1.97, 3.99-4.10, 4.30-4.35, 5.05, 6.21, 6.44, 6.79-6.82, 6.84-6.85, 6.88-6.90, 6.93-6.96, 7.08-7.10, 7.16, 7.23, 7.51-7.55, 7.57-7.61, 7.75-7.78, 10.25, 12.30.

Example 61(6): 2-[4-[(E,3R)-5-[3-(Benzenesulfonamido)phenyl]-3-hydroxypent-4-enoxy]phenyl]-2-methylpropanoic acid HPLC retention time (min): 0.92;

¹H-NMR (DMSO-d6): δ 1.44, 1.83-1.93, 3.99-4.08, 4.29-4.33, 5.04, 6.21, 6.42, 6.86-6.88, 6.93-6.95, 7.16, 7.23-7.25, 7.51-7.55, 7.57-7.60, 7.75-7.77, 10.25, 12.30.

Example 61(7): 4-[2-[(E,3R)-5-[3-(Benzenesulfonamido)phenyl]-3-hydroxypent-4-enoxy]phenyl]butanoic acid

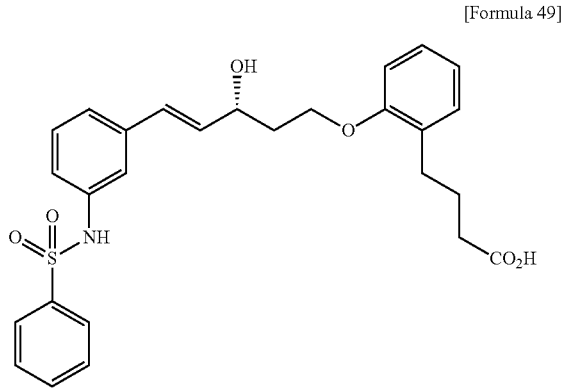 [SMILES: O=C(O)CCCc1ccccc1OCC[C@@H](O)/C=C/c1cccc(NS(=O)(=O)c2ccccc2)c1]

[Formula 49]

HPLC retention time (min): 0.95;
¹H-NMR (CDCl₃): δ 1.92-2.00, 2.12, 2.28-2.42, 2.68-2.71, 4.07-4.20, 4.63, 6.85-6.96, 7.08-7.19, 7.40-7.59, 7.59-7.63, 7.75-7.77.

Example 61(8): 3-[2-[(E,3R)-5-[3-(Benzenesulfonamido)phenyl]-3-hydroxypent-4-enoxy]phenyl]-2,2-dimethylpropanoic acid HPLC retention time (min): 0.95
¹H-NMR (CDCl₃): δ 1.21, 2.05-2.15, 2.96, 4.07-4.15, 4.60, 6.23, 6.53, 6.85-7.00, 7.07-7.20, 7.40-7.63, 7.76-7.78.

Example 62: 2-[2-[(E,3R)-5-[3-(Benzenesulfonamido)phenyl]-3-hydroxypent-4-enoxy]phenyl]-2-methylpropanoic acid The same designed procedures as in Example 54→Example 55→Example 56→Example 57 were carried out using, in place of methyl (E)-3-(2-hydroxyphenyl)prop-2-enoate used in Example 54, the phenol compound produced in Example 47. In this manner, the title compound having the physical property values shown below was produced.
HPLC retention time (min): 0.95;
¹H-NMR (CDCl₃): δ 1.63-1.65, 2.09-2.14, 4.13-4.21, 4.58, 6.28, 6.52, 6.82-6.84, 7.00-7.06, 7.15-7.19, 7.40-7.62, 7.76-7.78.

Example 63: 1-[[2-[(E,3R)-5-[3-(Benzenesulfonamido)phenyl]-3-hydroxypent-4-enoxy]phenyl]methyl]cyclopropane-1-carboxylic acid The same designed procedures as in Example 54→Example 55→Example 56→Example 57 were carried out using, in place of methyl (E)-3-(2-hydroxyphenyl)prop-2-enoate used in Example 54, the compound produced in Example 48. In this manner, the title compound having the physical property values shown below was produced.
HPLC retention time (min): 0.96;
¹H-NMR (CDCl₃): δ 1.38-1.40, 2.11-2.16, 4.13-4.18, 4.58, 6.28, 6.54, 6.85-7.20, 7.38-7.52, 7.74-7.76.

Example 64: 4-[2-[(E,3R)-5-[3-(Benzenesulfonamido)phenyl]-3-hydroxypent-4-enoxy]phenyl]-2,2-dimethylbutanoic acid The same designed procedures as in Example 54→Example 55→Example 56→Example 57 were carried out using, in place of methyl (E)-3-(2-hydroxyphenyl)prop-2-enoate used in Example 54, the compound produced in Example 49. In this manner, the title compound having the physical property values shown below was produced.
HPLC retention time (min): 1.00;
¹H-NMR (CDCl₃): δ 1.28, 1.74-1.91, 2.08-2.17, 2.61, 4.01-4.16, 4.62, 6.22, 6.51, 6.81-7.17, 7.39-7.43, 7.48-7.53, 7.75-7.78.

Example 65: 1-[2-[2-[(E,3R)-5-[3-(Benzenesulfonamido)phenyl]-3-hydroxypent-4-enoxy]phenyl]ethyl]cyclopropane-1-carboxylic acid The same designed procedures as in Example 54→Example 55→Example 56→Example 57 were carried out using, in place of methyl (E)-3-(2-hydroxyphenyl)prop-2-enoate used in Example 54, the phenol compound produced in Example 51. In this manner, the title compound having the physical property values shown below was produced.
HPLC retention time (min): 1.00;
¹H-NMR (CDCl₃): δ 0.66-0.76, 1.19-1.30, 1.64-1.72, 1.79-1.88, 2.08-2.14, 2.75-2.89, 4.10-4.21, 4.65, 6.28, 6.55, 6.83-6.90, 6.96-7.00, 7.07-7.18, 7.35-7.39, 7.46-7.52, 7.73-7.76.

Examples 66(1) to (3)

The same designed procedures as in Example 1→Example 54→Example 55→Example 56→Example 57 were carried out using, in place of 3,4-dihydrocoumarin used in Example 1, corresponding lactone compounds. In this manner, the following compounds of Examples were produced.

Example 66(1): 3-[2-[(E,3R)-5-[3-(Benzenesulfonamido)phenyl]-3-hydroxypent-4-enoxy]-5-bromophenyl]propanoic acid HPLC retention time (min): 0.99;
¹H-NMR (CD₃OD): δ 2.06-2.10, 2.56-2.60, 2.88-2.92, 4.07-4.19, 4.51, 6.23, 6.53, 6.86-6.88, 6.97-7.00, 7.11-7.19, 7.29-7.32, 7.46-7.50, 7.54-7.58, 7.76-7.78.

Example 66(2): 3-[2-[(E,3R)-5-[3-(Benzenesulfonamido)phenyl]-3-hydroxypent-4-enoxy]-5-methylphenyl]propanoic acid HPLC retention time (min): 0.98;
¹H-NMR (CD₃OD): δ 1.92-1.96, 2.13, 2.42-2.46, 2.75-2.79, 3.63-4.03, 4.41, 6.11, 6.42, 6.69, 6.84-6.89, 6.99-7.06, 7.34-7.46, 7.64-7.66.

Example 66(3): 3-[2-[(E,3R)-5-[3-(Benzenesulfonamido)phenyl]-3-hydroxypent-4-enoxy]-4-methylphenyl]propanoic acid HPLC retention time (min): 0.97;
¹H-NMR (CD₃OD): δ 1.92-1.97, 2.18, 2.41-2.45, 2.74-2.78, 3.93-4.06, 4.42, 6.11, 6.41, 6.56, 6.64, 6.86-6.92, 7.00-7.07, 7.33-7.46, 7.64-7.66.

Example 67: 3-[2-[(E,3R)-5-[3-(Benzenesulfonamido)phenyl]-3-hydroxypent-4-enoxy]-5-fluorophenyl]propanoic acid The same designed procedures as in Example 54→Example 55→Example 56→Example 57 were carried out using, in place of methyl (E)-3-(2-hydroxyphenyl)prop-2-enoate used in Example 54, the phenol compound produced in Example 53. In this manner, the title compound having the physical property values shown below was produced.

HPLC retention time (min): 0.94;

$^1$H-NMR (CDCl$_3$): δ 2.09-2.15, 2.67-2.71, 2.93-2.97, 4.10-4.15, 4.59, 6.27, 6.54, 6.77-6.80, 6.84-6.90, 6.95-7.00, 7.08-7.10, 7.16, 7.40-7.44, 7.50-7.55, 7.76-7.78.

Examples 68(1) to (2)

The same designed procedures as in Example 52→Example 53→Example 54→Example 55→Example 56→Example 57 were carried out using corresponding aldehyde compounds in place of 2-benziloxy-5-fluoro-benzaldehyde used in Example 52 and using corresponding phenol compounds in place of methyl (E)-3-(2-hydroxyphenyl)prop-2-enoate used in Example 54. In this manner, the following compounds of Examples were produced.

Example 68(1): 3-[2-[(E,3R)-5-[3-(Benzenesulfonamido)phenyl]-3-hydroxypent-4-enoxy]-6-fluorophenyl]propanoic acid HPLC retention time (min): 0.95;

$^1$H-NMR (CDCl$_3$): δ 2.09-2.15, 2.61-2.65, 2.97-3.01, 4.10-4.17, 4.60, 6.26, 6.54, 6.65-6.70, 6.97-7.00, 7.05-7.18, 7.41-7.44, 7.50-7.54, 7.76-7.79.

Example 68(2): 3-[2-[(E,3R)-5-[3-(Benzenesulfonamido)phenyl]-3-hydroxypent-4-enoxy]-3-fluorophenyl]propanoic acid HPLC retention time (min): 0.94;

$^1$H-NMR (CDCl$_3$): δ 2.09-2.15, 2.69-2.73, 3.01-3.05, 4.22-4.24, 4.67, 6.30, 6.58, 6.95-7.01, 7.10-7.20, 7.42-7.45, 7.51-7.54, 7.77-7.79.

Example 69: 3-[2-[(E,3S)-5-[3-(Benzenesulfonamido)phenyl]-3-hydroxypent-4-enoxy]phenyl]propanoic acid The same designed procedures as in Example 54→Example 55→Example 56→Example 57 were carried out using the compound produced in Example 1 in place of methyl (E)-3-(2-hydroxyphenyl)prop-2-enoate used in Example 54 and using (S,E)-5-hydroxy-1-(3-nitrophenyl)pent-1-en-3-yl benzoate produced in Example 54 in place of (R,E)-5-hydroxy-1-(3-nitrophenyl)pent-1-en-3-yl benzoate used in Example 54. In this manner, the title compound having the physical property values shown below was produced.

HPLC retention time (min): 0.93;

$^1$H-NMR (CD$_3$OD): δ 2.05-2.10, 2.57-2.61, 2.91-2.95, 4.10, 4.17, 4.51-4.56, 6.24, 6.53, 6.86, 6.93, 6.98, 7.12-7.20, 7.45-7.50, 7.56, 7.75-7.78.

Example 70: 3-[2-[(3R)-5-[3-(Benzenesulfonamido)phenyl]-3-hydroxypentoxy]phenyl]propanoic acid

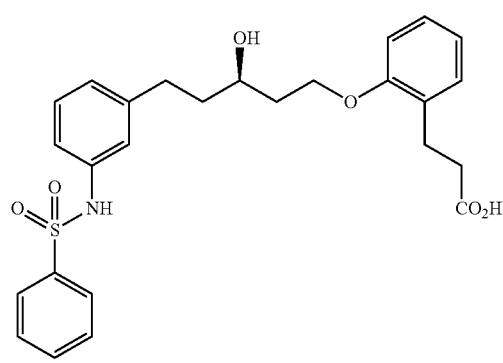

[Formula 50]

The same designed procedure as in Example 33 was carried out using the compound produced in Example 69. In this manner, the title compound having the physical property values shown below was produced.

HPLC retention time (min): 0.93;

$^1$H-NMR (CD$_3$OD): δ 1.69-2.02, 2.59-2.75, 2.90-2.96, 3.89, 4.05-4.18, 6.85-7.00, 7.11-7.22, 7.36-7.43, 7.44-7.53, 7.76.

Example 71: Isopropyl (R,E)-3-(2-((5-(3-aminophenyl)-3-((trimethylsilyl)oxy)pent-4-en-1-yl)oxy)phenyl)propanoate 3-Bromoaniline (421 mg), chloro(2-dicyclohexylphosphino-2',4',6'-triisopropyl-1,1'-biphenyl)[2-(2'-amino-1,1'-biphenyl)]palladium (II) (0.30 g) and a 2-M aqueous tripotassium phosphate solution (5.7 mL) were added to a solution of the compound produced in Example 8 (1.00 g) in THF (10 mL), and the resultant solution was stirred at 70° C. for 19 hours. The reaction solution was cooled to room temperature, water was then added to the solution, and the resultant solution was extracted with ethyl acetate. An organic layer was dried over sodium sulfate, and was then concentrated under a reduced pressure. The resultant residue was purified by silica gel column chromatography (hexane:ethyl acetate=9:1→2:1). In this manner, the title compound (515 mg) having the physical property value shown below was produced.

HPLC retention time (min): 0.82.

Example 72: Isopropyl (R,E)-3-(2-((5-(3-((4-fluorophenyl)sulfonamido)phenyl)-3-hydroxypent-4-en-1-yl)oxy)phenyl)propanoate Pyridine (0.018 mL), DMAP (2.7 mg) and 4-fluorobenzenesulfonyl chloride (CAS Registry Number: 349-88-2) (25.6 mg) were added to a solution of the compound produced in Example 71 (50 mg) in THF (1 mL) at room temperature, and the resultant solution was stirred at the same temperature for 16 hours. TBAF (a 1.0-M THF solution, 0.27 mL) was added to the reaction solution at room temperature, and the resultant solution was stirred at the same temperature for 1 hour. Water was added to the reaction solution, and the resultant solution was extracted with ethyl acetate. An organic layer was dried over sodium sulfate, and was then concentrated under a reduced pressure.

The resultant residue was preparatively purified by high-performance liquid chromatography (mobile phase A (a 0.1% aqueous TFA solution): mobile phase B (0.1% TFA/acetonitrile)=90:0→10:90). In this manner, the title compound (515 mg) having the physical property values shown below was produced.

HPLC retention time (min): 1.11.

Example 73: 3-[2-[(E,3R)-5-[3-[(4-Fluorophenyl)sulfonylamino]phenyl]-3-hydroxypent-4-enoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the compound produced in Example 72. In this manner, the title compound having the physical property values shown below was produced.

HPLC retention time (min): 0.94
$^1$H-NMR (CD$_3$OD): δ 2.06-2.11, 2.57-2.61, 2.91-2.95, 4.10, 4.18, 4.55, 6.26, 6.55, 6.86, 6.93, 6.99, 7.13-7.25, 7.79-7.82.

Examples 74(1) to (21) The same designed procedures as in Example 72→Example 11 were carried out using, in place of 4-fluorobenzenesulfonyl chloride used in Example 72, corresponding sulfonyl compounds. In this manner, the following compounds of Examples were produced.

Example 74(1) 3-[2-[(E,3R)-5-[3-[(4-Chlorophenyl)sulfonylamino]phenyl]-3-hydroxypent-4-enoxy]phenyl]propanoic acid HPLC retention time (min): 0.98;
$^1$H-NMR (CD$_3$OD): δ 2.06-2.11, 2.57-2.61, 2.91-2.95, 4.10, 4.18, 4.55, 6.26, 6.55, 6.86, 6.93, 6.99, 7.13-7.21, 7.48-7.51, 7.71-7.75.

Example 74(2)

3-[2-[(E,3R)-3-Hydroxy-5-[3-[(4-methylphenyl)sulfonylamino]phenyl]pent-4-enoxy]phenyl]propanoic acid HPLC retention time (min): 0.96;
$^1$H-NMR (CD$_3$OD): δ 2.06-2.11, 2.37, 2.57-2.61, 2.91-2.95, 4.10, 4.18, 4.54, 6.24, 6.54, 6.86, 6.93, 6.98, 7.11-7.20, 7.27-7.30, 7.63-7.66.

Example 74(3): 3-[2-[(E,3R)-3-Hydroxy-5-[3-[[4-(trifluoromethyl)phenyl]sulfonylamino]phenyl]pent-4-enoxy]phenyl]propanoic acid HPLC retention time (min): 1.01;
$^1$H-NMR (CD$_3$OD): δ 2.06-2.10, 2.57-2.61, 2.91-2.95, 4.10, 4.18, 4.54, 6.27, 6.55, 6.86, 6.93, 6.99, 7.15-7.22, 7.80-7.83, 7.93-7.95.

Example 74(4): 3-[2-[(E,3R)-5-[3-[(4-Butylphenyl)sulfonylamino]phenyl]-3-hydroxypent-4-enoxy]phenyl]propanoic acid HPLC retention time (min): 1.08;
$^1$H-NMR (CD$_3$OD): δ 0.93, 1.31-1.36, 1.55-1.63, 2.06-2.10, 2.57-2.67, 2.91-2.95, 4.11, 4.18, 4.54, 6.24, 6.54, 6.86, 6.93, 6.98, 7.11-7.20, 7.28-7.30, 7.65-7.68.

Example 74(5): 3-[2-[(E,3R)-5-[3-[(3-Fluorophenyl)sulfonylamino]phenyl]-3-hydroxypent-4-enoxy]phenyl]propanoic acid HPLC retention time (min): 0.96;
MS (ESI, Pos.): 482 (M+H–H$_2$O)$^+$.

Example 74(6): 3-[2-[(E,3R)-5-[3-[(3-Chlorophenyl)sulfonylamino]phenyl]-3-hydroxypent-4-enoxy]phenyl]propanoic acid HPLC retention time (min): 1.00;
MS (ESI, Pos.): 498 (M+H–H$_2$O)$^+$.

Example 74(7): 3-[2-[(E,3R)-3-Hydroxy-5-[3-[(3-methylphenyl)sulfonylamino]phenyl]pent-4-enoxy]phenyl]propanoic acid HPLC retention time (min): 0.97;
MS (ESI, Pos.): 478 (M+H–H$_2$O)$^+$.

Example 74(8): 3-[2-[(E,3R)-3-Hydroxy-5-[3-[[3-(trifluoromethyl)phenyl]sulfonylamino]phenyl]pent-4-enoxy]phenyl]propanoic acid HPLC retention time (min): 1.00;
MS (ESI, Pos.): 532 (M+H–H$_2$O)$^+$.

Example 74(9): 3-[2-[(E,3R)-5-[3-[(2-Fluorophenyl)sulfonylamino]phenyl]-3-hydroxypent-4-enoxy]phenyl]propanoic acid HPLC retention time (min): 0.94;
MS (ESI, Pos.): 482 (M+H–H$_2$O)$^+$.

Example 74(10): 3-[2-[(E,3R)-5-[3-[(2-Chlorophenyl)sulfonylamino]phenyl]-3-hydroxypent-4-enoxy]phenyl]propanoic acid HPLC retention time (min): 0.97;
MS (ESI, Pos.): 498 (M+H–H$_2$O)$^+$.

Example 74(11): 3-[2-[(E,3R)-3-Hydroxy-5-[3-[(2-methylphenyl)sulfonylamino]phenyl]pent-4-enoxy]phenyl]propanoic acid HPLC retention time (min): 0.97;
MS (ESI, Pos.): 478 (M+H–H$_2$O)$^+$.

Example 74(12): 3-[2-[(E,3R)-3-Hydroxy-5-[3-[[2-(trifluoromethyl)phenyl]sulfonylamino]phenyl]pent-4-enoxy]phenyl]propanoic acid HPLC retention time (min): 0.99;
MS (ESI, Pos.): 532 (M+H–H$_2$O)$^+$.

Example 74(13): 3-[2-[(E,3R)-5-[3-(Cyclopentylsulfonylamino)phenyl]-3-hydroxypent-4-enoxy]phenyl]propanoic acid

[Formula 51]

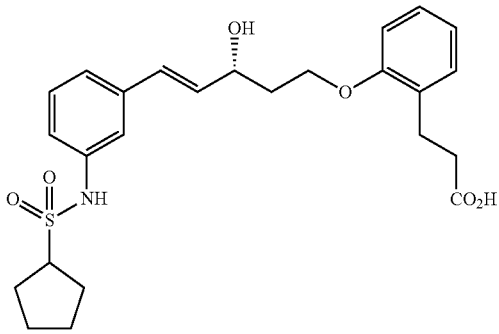

HPLC retention time (min): 0.93;
$^1$H-NMR (CD$_3$OD): δ 1.60-1.67, 1.74-1.81, 1.90-2.05, 2.08-2.13, 2.58-2.62, 2.92-2.96, 3.56, 4.13, 4.20, 4.58, 6.35, 6.62, 6.86, 6.94, 7.14-7.20, 7.26-7.32.

Example 74(14): 3-[2-[(E,3R)-3-Hydroxy-5-[3-(oxan-4-ylsulfonylamino)phenyl]pent-4-enoxy]phenyl]propanoic acid TLC: Rf 0.48 (ethyl acetate);
$^1$H-NMR (CDCl$_3$): δ 1.88-2.00, 2.15-2.20, 2.63-2.74, 2.90-3.02, 3.22-3.35, 4.04, 4.17, 6.38, 6.60, 6.88, 7.13-7.28.

Example 74(15): 3-[2-[(E,3R)-5-[3-(Benzilsulfonylamino)phenyl]-3-hydroxypent-4-enoxy]phenyl]propanoic acid TLC: Rf 0.55 (hexane: ethyl acetate=1:2);
$^1$H-NMR (CDCl$_3$): δ 2.13-2.18, 2.67, 2.96, 4.13-4.22, 4.34, 4.64, 6.35, 6.61, 6.89, 6.96, 7.06, 7.13-7.36.

Example 74(16): 3-[2-[(E,3R)-3-Hydroxy-5-[3-(pyridin-2-ylsulfonylamino)phenyl]pent-4-enoxy]phenyl]propanoic acid TLC: Rf 0.36 (ethyl acetate);
$^1$H-NMR (CDCl$_3$): δ 2.06-2.23, 2.72, 3.02, 4.16, 4.60, 6.31, 6.52, 6.86-6.93, 7.01, 7.10-7.22, 7.46, 7.85, 7.97, 8.41, 8.65.

Example 74(17): 3-[2-[(E,3R)-5-[3-(1-Benzofuran-3-ylsulfonylamino)phenyl]-3-hydroxypent-4-enoxy]phenyl]propanoic acid HPLC retention time (min): 0.98;
$^1$H-NMR (CDCl$_3$): δ 2.08-2.13, 2.69, 2.96, 4.11, 4.55-4.62, 6.21, 6.52, 684-6.92, 6.99-7.03, 7.09-7.19, 7.30-7.40, 7.50, 7.70, 8.05.

Example 74(18): 3-[2-[(E,3R)-5-[3-[(4-Butoxyphenyl)sulfonylamino]phenyl]-3-hydroxypent-4-enoxy]phenyl]propanoic Acid TLC: Rf 0.40 (hexane: ethyl acetate=1:2);
$^1$H-NMR (CDCl$_3$): δ 0.95, 1.40-1.50, 1.68-1.79, 2.10-2.14, 2.68, 2.96, 3.93, 4.10-4.19, 4.60, 6.26, 6.52, 6.81-6.91, 6.97-7.09, 7.12-7.24, 7.68.

Example 74(19): 3-[2-[(E,3R)-3-Hydroxy-5-[3-(thiophen-3-ylsulfonylamino)phenyl]pent-4-enoxy]phenyl]propanoic Acid TLC: Rf 0.35 (hexane: ethyl acetate=1:2);
$^1$H-NMR (CDCl$_3$): δ 2.10-2.15, 2.68, 2.96, 4.09-4.20, 4.62, 6.27, 6.54, 6.84-6.92, 7.00-7.23, 7.27-7.32, 7.86.

Example 74(20): 3-[2-[(E,3R)-3-Hydroxy-5-[3-[(2-propylphenyl)sulfonylamino]phenyl]pent-4-enoxy]phenyl]propanoic Acid TLC: Rf 0.38 (hexane: ethyl acetate=1:2);
$^1$H-NMR (CDCl$_3$): δ 1.00, 1.64-1.74, 2.10-2.15, 2.70, 2.93-3.01, 4.10-4.19, 4.60, 6.26, 6.53, 6.85-6.92, 7.02-7.06, 7.10-7.24, 7.33, 7.45, 7.95.

Example 74(21): 3-[2-[(E,3R)-5-[3-[(3-Butylphenyl)sulfonylamino]phenyl]-3-hydroxypent-4-enoxy]phenyl]propanoic Acid TLC: Rf 0.38 (hexane: ethyl acetate=1:2);
$^1$H-NMR (CDCl$_3$): δ 0.86, 1.18-1.28, 1.42-1.53, 2.08-2.14, 2.57, 2.69, 2.97, 4.10-4.21, 4.61, 6.25, 6.53, 6.84-6.92, 6.98, 7.04-7.21, 7.29-7.32, 7.55-7.60.

Example 75: 3-[2-[(3S)-5-[3-(Cyclopentylsulfonylamino)phenyl]-3-hydroxypentoxy]phenyl]propanoic Acid The same designed procedure as in Example 33 was carried out using, in place of 3-[2-[(E,3R)-5-[3-(benzenesulfonamido)phenyl]-3-hydroxypent-4-enoxy]phenyl]propanoic acid used in Example 33, the compound produced in Example 74(13). In this manner, the following compound of Example was produced.

HPLC retention time (min): 0.93;
$^1$H-NMR (CD$_3$OD): δ 1.55-1.63, 1.74-2.07, 2.52-2.56, 2.73, 2.84, 2.85-2.89, 3.53, 3.89, 4.09-4.19, 6.85, 6.93, 7.02, 7.08-7.19, 7.23.

Example 76: Methyl (R,E)-3-(2-((3-hydroxy-5-(3-(phenylsulfonamido)phenyl)pent-4-en-1-yl)oxy)phenyl)propanoate Trimethylsilyldiazomethane (a 2.0-M hexane solution, 2.6 mL) was added to a solution of the compound produced in Example 11 (500 mg) in methanol (10 mL) under ice cooling, and the resultant solution was stirred at room temperature for 30 minutes. Acetic acid was added to the reaction solution under ice cooling, and the resultant solution was concentrated under a reduced pressure. The resultant residue was purified by silica gel column chromatography (hexane: ethyl acetate=7:3→1:1). In this manner, the title compound (495 mg) having the physical property value shown below was produced.

HPLC retention time (min): 1.03.

Example 77: Methyl 3-[2-[(E)-5-[3-(benzenesulfonamido)phenyl]-3-oxopent-4-enoxy]phenyl]propanoate Manganese dioxide (868 mg) was added to a solution of the compound produced in Example 76 (495 mg) in dichloromethane (10 mL) at room temperature, and the resultant solution was stirred at the same temperature for 20 hours. The reaction solution was filtrated through Celite (trade name), and a filtrate was concentrated under a reduced pressure. The resultant residue was purified by silica gel column chromatography (hexane: ethyl acetate=7:3→1:1). In this manner, the title compound (439 mg) having the physical property values shown below was produced.

HPLC retention time (min): 1.10.

$^1$H-NMR (CDCl$_3$): δ 2.59-2.63, 2.88-2.92, 3.08-3.11, 3.68, 4.31-4.34, 6.80, 6.85-6.92, 7.12, 7.18-7.34, 7.42-7.56, 7.77-7.80.

Example 78: 3-[2-[(E)-5-[3-(Benzenesulfonamido)phenyl]-3-oxopent-4-enoxy]phenyl]propanoic acid The same designed procedure as in Example 77 was carried out using, in place of methyl (R,E)-3-(2-((3-hydroxy-5-(3-(phenylsulfonamido)phenyl)pent-4-en-1-yl)oxy)phenyl)propanoate used in Example 77, the compound produced in Example 11. In this manner, the title compound having the physical property values shown below was produced.

HPLC retention time (min): 0.97;

$^1$H-NMR (CD$_3$OD): δ 2.44-2.48, 2.81-2.85, 3.22, 3.25, 4.33-4.37, 6.82, 6.86, 6.97, 7.14-7.21, 7.29, 7.33-7.39, 7.48-7.52, 7.56-7.63, 7.79-7.81.

Example 79: 3-[2-[5-[3-(Benzenesulfonamido)phenyl]-3-oxopentoxy]phenyl]propanoic acid The same designed procedure as in Example 33 was carried out using, in place of 3-[2-[(E,3R)-5-[3-(benzenesulfonamido)phenyl]-3-hydroxypent-4-enoxy]phenyl]propanoic acid used in Example 33, the compound produced in Example 78. In this manner, the title compound having the physical property values shown below was produced.

HPLC retention time (min): 0.97;

$^1$H-NMR (CD$_3$OD): δ 2.47-2.51, 2.80-2.85, 2.88-2.91, 4.21-4.24, 6.85-6.95, 7.09-7.21, 7.44-7.48, 7.54, 7.74-7.76.

Example 80: 3-[2-[5-[3-(1-Hydroxy-2-phenylethyl)phenyl]-3-oxopentoxy]phenyl]propanoic acid The same designed procedures as in Example 78→Example 79 were carried out using, in place of 3-[2-[(E,3R)-5-[3-(benzenesulfonamido)phenyl]-3-hydroxypent-4-enoxy]phenyl]propanoic acid used in Example 78, the compound produced in Example 12(9). In this manner, the title compound having the physical property values shown below was produced.

HPLC retention time (min): 1.00;

$^1$H-NMR (CD$_3$OD): δ 2.48-2.52, 2.80-2.96, 3.03-3.08, 4.25, 4.82, 6.85-6.94, 7.08-7.22.

Example 81: Isopropyl 3-(2-(pent-4-yn-1-yloxy)phenyl)propanoate

Cesium carbonate (9.39 g) was added to a solution of the compound produced in Example 1 (3.00 g) in N,N-dimethylacetamide (25 mL) at room temperature, and the resultant solution was stirred at the same temperature for 15 minutes. 5-Chloro-1-penthyne (CAS Registry Number: 14267-92-6) (1.63 g) was added to the reaction solution at room temperature, and the resultant solution was stirred at 60° C. for 3 hours. Water was added to the reaction solution, and the resultant solution was extracted with diethyl ether. An organic layer was dried over sodium sulfate, and was then concentrated under a reduced pressure. The resultant residue was purified by silica gel column chromatography (hexane: ethyl acetate=1:0→5:1). In this manner, the title compound (2.40 g) having the physical property value shown below was produced.

HPLC retention time (min): 1.13.

Example 82: Isopropyl (E)-3-(2-((5-(4,4,5,5-tetramethyl-1,3,2-dioxaboran-2-yl)pent-4-en-1-yl)oxy)phenyl)propanoate 4,4,5,5-Tetramethyl-1,3,2-dioxaborolane (1.17 g) and 4-dimethylaminobenzoic acid (60.2 mg) were added to a solution of the compound produced in Example 81 (1.00 g) in heptane (2 mL) at room temperature, and the resultant solution was stirred at 100° C. for 4 hours. The reaction solution was cooled to room temperature, and was then concentrated. The resultant residue was purified by silica gel column chromatography (hexane: ethyl acetate=20:1→4:1). In this manner, the title compound (503 mg) having the physical property value shown below was produced.

HPLC retention time (min): 1.38.

Example 83: Isopropyl (E)-3-(2-((5-(3-(phenylsulfonamido)phenyl)pent-4-en-1-yl)oxy)phenyl)propanoate The compound produced in Example 9 (168 mg), chloro(2-dicyclohexylphosphino-2',4',6'-triisopropyl-1,1'-biphenyl)[2-(2'-amino-1,1'-biphenyl)]palladium (II) (0.035 g) and a 2-M aqueous tripotassium phosphate solution (0.67 mL) were added to a solution of the compound produced in Example 82 (180 mg) in THF (3 mL), and the resultant solution was stirred at 60° C. for 1 hour. The reaction solution was cooled to room temperature, water was then added to the solution, and the resultant solution was extracted with ethyl acetate. An organic layer was dried over sodium sulfate, and was then concentrated under a reduced pressure. The resultant residue was purified by silica gel column chromatography (hexane: ethyl acetate=7:1→2:1). In this manner, the title compound (113 mg) having the physical property value shown below was produced.

HPLC retention time (min): 1.24.

Example 84: 3-[2-[(E)-5-[3-(Benzenesulfonamido)phenyl]pent-4-enoxy]phenyl]propanoic acid

[Formula 52]

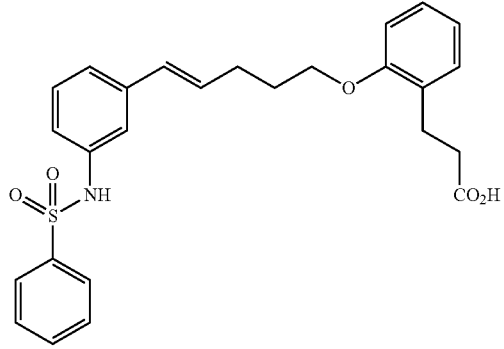

A 1-M aqueous lithium hydroxide solution (0.5 mL) was added to a solution of the compound produced in Example 83 (146 mg) in THF (0.5 mL) and methanol (0.1 mL), and the resultant solution was stirred at 50° C. for 8 hours. 1 M Hydrochloric acid was added to the solution to render the solution acidic, and the resultant solution was extracted with ethyl acetate. An organic layer was dried over sodium sulfate, and was then concentrated under a reduced pressure. In this manner, the title compound (105 mg) having the physical property values shown below was produced.

HPLC retention time (min): 1.10
$^1$H-NMR (CD$_3$OD): δ 1.95-2.03, 2.41-2.46, 2.57-2.61, 2.92-2.95, 4.03-4.06, 6.24, 6.36, 6.86, 6.90-6.95, 7.06-7.08, 7.11-7.19, 7.45-7.49, 7.55, 7.75-7.78.

Example 85: 3-[2-[(E)-5-[4-(1-Hydroxy-2-phenylethyl)phenyl]pent-4-enoxy]phenyl]propanoic acid The same designed procedures as in Example 83→Example 84 were carried out using, in place of N-(3-bromophenyl)benzenesulfonamide used in Example 83, 1-(4-bromophenyl)-2-phenylethan-1-ol (CAS Registry Number: 20498-64-0). In this manner, the following compound of Example was produced.

HPLC retention time (min): 1.10;
$^1$H-NMR (CDCl$_3$): δ 1.97-2.03, 2.41-2.45, 2.67-2.71, 2.96-3.03, 4.04, 4.86-4.90, 6.23-6.30, 6.44, 6.83-6.89, 7.16-7.34.

Example 86: 3-[2-[(E)-5-[3-[(1R)-1-Hydroxy-2-phenylethyl]phenyl]pent-4-enoxy]phenyl]propanoic acid The same designed procedures as in Example 83→Example 84 were carried out using, in place of N-(3-bromophenyl)benzenesulfonamide used in Example 83, the compound produced in Example 21. In this manner, the title compound having the physical property values shown below was produced.

HPLC retention time (min): 1.20;
$^1$H-NMR (CDCl$_3$): δ 2.00, 2.43, 2.64-2.70, 2.95-3.07, 4.04, 4.89, 6.28, 6.44, 6.83-6.89, 7.15-7.39.

Example 87: 3-[2-[(E)-5-[3-[(1S)-1-Hydroxy-2-phenylethyl]phenyl]pent-4-enoxy]phenyl]propanoic acid The same designed procedures as in Example 21→Example 83→Example 84 were carried out using (S)-methyloxazaborolidine in place of (R)-methyloxazaborolidine used in Example 21 and using a corresponding halide compound in place of N-(3-bromophenyl)benzenesulfonamide used in Example 83. In this manner, the title compound having the physical property values shown below was produced.

HPLC retention time (min): 1.20;
$^1$H-NMR (CDCl$_3$): δ 2.00, 2.44, 2.66-2.70, 2.95-3.07, 4.04, 4.89, 6.28, 6.45, 6.83-8.89, 7.15-7.40.

Examples 87(1) to (10)

The same designed procedures as in Example 9→Example 83→Example 84 were carried out using, in place of 3-bromoaniline used in Example 9, corresponding amine compounds. In this manner, the title compounds having the physical property values shown below were produced.

Example 87(1): 3-[2-[(E)-5-[3-(Benzenesulfonamido)-2-(trifluoromethyl)phenyl]pent-4-enoxy]phenyl]propanoic acid HPLC retention time (min): 1.08;
$^1$H-NMR (CDCl$_3$): δ 1.92-1.99, 2.36-2.42, 2.64-2.68, 2.93-2.97, 3.99, 5.98, 6.02, 6.58-6.65, 6.81, 6.88, 7.00, 7.15-7.20, 7.39-7.45, 7.51-7.56, 7.65, 7.70-7.73.

Example 87(2): 3-[2-[(E)-5-[5-(Benzenesulfonamido)-2-(trifluoromethyl)phenyl]pent-4-enoxy]phenyl]propanoic acid HPLC retention time (min): 1.10;
$^1$H-NMR (CDCl$_3$): δ 1.97-2.04, 2.43-2.49, 2.74-2.78, 3.00-3.04, 4.04, 6.25-6.32, 6.66, 6.85, 6.91, 7.10-7.25, 7.44-7.48, 7.53-7.58, 7.84-7.87.

Example 87(3): 3-[2-[(E)-5-[3-(Benzenesulfonamido)-5-(trifluoromethyl)phenyl]pent-4-enoxy]phenyl]propanoic acid HPLC retention time (min): 1.11;
$^1$H-NMR (CDCl$_3$): δ 1.96-2.02, 2.41-2.46, 2.72-2.76, 2.97-3.01, 4.03, 6.31-6.40, 6.84, 6.90, 7.15-7.25, 7.43-7.48, 7.52-7.57, 7.79-7.82.

Example 87(4): 3-[2-[(E)-5-[3-(Benzenesulfonamido)-4-(trifluoromethyl)phenyl]pent-4-enoxy]phenyl]propanoic acid HPLC retention time (min): 1.10;
$^1$H-NMR (CDCl$_3$): δ 1.98-2.05, 2.45-2.50, 2.68-2.72, 2.97-3.01, 4.04, 6.36-6.47, 6.80-6.91, 7.15-7.22, 7.37-7.44, 7.51-7.55, 7.74-7.79.

Example 87(5): 3-[2-[(E)-5-[3-(Benzenesulfonamido)-2-cyanophenyl]pent-4-enoxy]phenyl]propanoic acid HPLC retention time (min): 1.01;
$^1$H-NMR (CDCl$_3$): δ 1.95-2.02, 2.44-2.49, 2.64-2.68, 2.93-2.97, 4.01, 6.44, 6.60, 6.82, 6.88, 7.15-7.20, 7.31-7.32, 7.42-7.50, 7.52-7.60, 7.82-7.85.

Example 87(6): 3-[2-[(E)-5-[3-(Benzenesulfonamido)-4-cyanophenyl]pent-4-enoxy]phenyl]propanoic acid HPLC retention time (min): 1.00;
$^1$H-NMR (CD$_3$OD): δ 1.98-2.04, 2.46-2.51, 2.57-2.61, 2.92-2.96, 4.04-4.07, 6.38-6.46, 6.87, 6.92, 7.16-7.20, 7.24, 7.34, 7.49-7.55, 7.60, 7.75-7.78.

Example 87(7): 3-[2-[(E)-5-[3-(Benzenesulfonamido)-2,4-dichlorophenyl]pent-4-enoxy]phenyl]propanoic acid HPLC retention time (min): 1.07;
$^1$H-NMR (CD$_3$OD): δ 1.87-1.94, 2.36-2.41, 2.44-2.48, 2.81, 3.95, 6.25, 6.59, 6.74, 6.79, 7.03-7.08, 7.22, 7.39-7.43, 7.49-7.53, 7.67-7.70.

Example 87(8): 3-[2-[(E)-5-[3-(Benzenesulfonamido)-4-methylsulfonylphenyl]pent-4-enoxy]phenyl]propanoic acid HPLC retention time (min): 1.10;
$^1$H-NMR (CDCl$_3$): δ 1.98-2.05, 2.46-2.50, 2.67-2.50, 2.77, 2.96-3.00, 4.03, 6.40-6.42, 6.84, 6.90, 7.16-7.22, 7.47-7.52, 7.58, 7.64, 7.71, 7.91-7.94.

Example 87(9): 3-[2-[(E)-5-[3-(Benzenesulfonamido)-5-methylsulfonylphenyl]pent-4-enoxy]phenyl]propanoic acid HPLC retention time (min): 0.99;
$^1$H-NMR (CDCl$_3$): δ 1.97-2.03, 2.44-2.49, 2.72-2.76, 2.97-3.03, 4.04, 6.36, 6.41-6.48, 6.84, 6.90, 7.15-7.22, 7.40, 7.45-7.49, 7.54-7.58, 7.77, 7.82-7.84.

Example 87(10): 3-[2-[(E)-5-[3-(Benzenesulfonamidomethyl)phenyl]pent-4-enoxy]phenyl]propanoic acid HPLC retention time (min): 1.10;
$^1$H-NMR (CDCl$_3$): δ 1.96-2.02, 2.39-2.44, 2.66-2.70, 2.93-2.97, 4.03, 4.12, 5.33, 6.24, 6.36, 6.83-6.90, 6.96-6.99, 7.14-7.21, 7.47-7.52, 7.54-7.59, 7.84-7.88.

Examples 88(1) to (2) The same designed procedure as in Example 83→Example 35→Example 84 were carried out using, in place of N-(3-bromophenyl)benzenesulfonamide used in Example 83, corresponding halide compounds. In this manner, the title compounds having the physical property values shown below were produced.

Example 88(1): 3-[2-[5-[3-(1-Hydroxy-2-phenylethyl)phenyl]pentoxy]phenyl]propanoic acid TLC: Rf 0.61 (hexane: ethyl acetate=1:2);
$^1$H-NMR (CDCl$_3$): δ 1.47-1.55, 1.67-1.74, 1.79-1.85, 2.58, 2.65, 2.88, 2.97-3.07, 3.96, 4.89, 6.79-6.88, 7.09-7.33.

Example 88(2): 3-[2-[5-[4-(1-Hydroxy-2-phenylethyl)phenyl]pentoxy]phenyl]propanoic acid HPLC retention time (min): 1.1;
$^1$H-NMR (CDCl$_3$): δ 1.47-1.80, 2.48-2.56, 2.64-2.69, 2.82-2.88, 3.02-3.06, 3.95, 4.89-4.93, 6.79-6.87, 7.11-7.34.

Example 89: (R)-3-[2-[5-[3-(1-Hydroxy-2-phenylethyl)phenyl]pentoxy]phenyl]propanoic acid, or (S)-3-[2-[5-[3-(1-hydroxy-2-phenylethyl)phenyl]pentoxy]phenyl]propanoic acid The compound produced in Example 88(1) was subjected to optical resolution employing SFC (column used: Daicel Corporation CHIRALPAK-IF (10 mm×250 mm), mobile phase: CO$_2$: acetonitrile: methanol=75:22.5:2.5, flow rate: 30 mL/min, pressure: 100 bar, wavelength: 220 nm, column temperature: 35° C.). Optically active substances of Example 88(1) produced under the optical resolution conditions were analyzed by SFC (column used: Daicel Corporation CHIRALPAK-IF (10 mm×250 mm), mobile phase: CO$_2$: acetonitrile: methanol=75:22.5:2.5, flow rate: 30 mL/min, pressure: 100 bar, wavelength: 220 nm, column temperature: 35° C.). As a result, the retention times for a first peak and a second peak were 14.9 minutes and 19.1 minutes, respectively.

Example 90: 4-Bromo-N-methoxy-N-methylthiazole-2-carboxamide

N,O-Dimethylhydroxylamine hydrochloride (609 mg), diisopropylethylamine (2.5 mL) and 1-(chloro-1-pyrrolidinylmethylene)pyrrolidinium hexafluorophosphate (2.4 g) were added to a solution of 4-bromothiazole-2-carboxylic acid (1.0 g) in dichloromethane (9.6 mL), and the resultant solution was stirred at room temperature for 5 hours. The reaction mixture was concentrated under a reduced pressure, and the resultant residue was purified by silica gel column chromatography (hexane: ethyl acetate=2:1). In this manner, the title compound (1.0 g) having the physical property value shown below was produced.
TLC: Rf 0.3 (hexane: ethyl acetate=2:1).

Example 91: 1-(4-Bromothiazol-2-yl)-2-phenylethan-1-one

Benzylmagnesium bromide (a 0.1-M diethyl ether solution, 40 mL) was added to a solution of the compound produced in Example 90 (300 mg) in diethyl ether (1 mL) at 0° C., and the resultant solution was stirred at room temperature for 1 hour. A saturated ammonium chloride solution was added to the reaction mixture, and the resultant solution was extracted with diethyl ether. An organic layer was dried over sodium sulfate, and was then concentrated under a reduced pressure. The resultant residue was purified by silica gel column chromatography (hexane: ethyl acetate=8:1). In this manner, the title compound (181 mg) having the physical property value shown below was produced.
TLC: Rf 0.7 (hexane: ethyl acetate=4:1).

Example 92: 3-[2-[(E)-5-[2-(1-Hydroxy-2-phenylethyl)-1,3-thiazol-4-yl]pent-4-enoxy]phenyl]propanoic acid The same designed procedures as in Example 21→Example 83→Example 84 were carried out using the compound produced in Example 91 in place of 1-(3-bromophenyl)-2-phenylethanone used in Example 21, using (RS)-methyloxazaborolidine in place of (R)-methyloxazaborolidine used in Example 21, and using a corresponding halide compound in place of N-(3-bromophenyl)benzenesulfonamide used in Example 83. In this manner, the title compound having the physical property values shown below was produced.
HPLC retention time (min): 0.98;
$^1$H-NMR (DMSO-d6): δ 1.92-2.00, 2.41-2.48, 2.80-2.84, 2.85-2.90, 3.10-3.15, 4.01-4.06, 4.80-4.85, 5.83, 6.60-6.72, 6.85, 6.95, 7.14-7.18, 7.21-7.25.

Example 93: 3-[2-[(E)-5-[4-(1-Hydroxy-2-phenylethyl)-1,3-thiazol-2-yl]pent-4-enoxy]phenyl]propanoic acid The same designed procedures as in Example 90→Example 91→Example 21 (in which (RS)-methyloxazaborolidine was used in place of (R)-methyloxazaborolidine)→Example 83→Example 84 were carried out using 2-bromothiazole-4-carboxylic acid in place of 4-bromothiazole-2-carboxylic acid used in Example 90, and using a corresponding halide compound in place of N-(3-bromophenyl)benzenesulfonamide used in Example 83. In this manner, the title compound having the physical property values shown below was produced.
HPLC retention time (min): 1.00;

$^1$H-NMR (CDCl$_3$): δ 1.98-2.05, 2.41-2.47, 2.66-2.70, 2.96-3.00, 3.08, 3.34, 4.03, 5.18, 6.42-6.46, 6.58, 6.62, 6.83-6.89, 6.93, 7.16-7.25, 7.27-7.34.

Example 94: 3-[2-[5-[5-(1-Hydroxy-2-phenylethyl)-1,3-thiazol-2-yl]pentoxy]phenyl]propanoic acid The same designed procedure as in Example 35 was carried out using, in place of isopropyl 3-(2-(((R,E)-3-hydroxy-5-(3-((R)-1-hydroxy-2-phenylethyl)phenyl)pent-4-en-1-yl)oxy)phenyl)propanoate used in Example 35, the compound produced in Example 93. In this manner, the following compound of Example was produced.

HPLC retention time (min): 0.96;
$^1$H-NMR (CDCl$_3$): δ 1.56-1.64, 1.80-1.90, 2.57-2.61, 2.94, 3.05, 3.09-3.11, 3.96, 5.14, 6.80, 6.86, 7.14-7.25, 7.29-7.33, 7.46.

Example 95: 3-[2-[5-[2-(1-Hydroxy-2-phenylethyl)-1,3-thiazol-5-yl]pentoxy]phenyl]propanoic acid The same designed procedure as in Example 35 was carried out using, in place of isopropyl 3-(2-(((R,E)-3-hydroxy-5-(3-((R)-1-hydroxy-2-phenylethyl)phenyl)pent-4-en-1-yl)oxy)phenyl)propanoate used in Example 35, the compound produced in Example 92. In this manner, the following compound of Example was produced.

HPLC retention time (min): 1.00;
$^1$H-NMR (CDCl$_3$): δ 1.51-1.59, 1.68-1.85, 2.57-2.61, 2.84, 2.90, 3.09, 3.27, 3.97, 5.14, 6.81, 6.86, 7.13-7.25, 7.28-7.32, 7.39.

Example 95(1): 3-[2-[(E)-5-[3-(Benzenesulfonamido)phenyl]pent-4-enoxy]phenyl]-N-methylsulfonylpropanamide Methanesulfonamide (102 mg), 1-ethyl-3-(3-Dimethylaminopropyl)carbodiimide hydrochloride (124 mg) and DMAP (78.7 mg) were added to a solution of the compound produced in Example 84 (100 mg) in DMF (1 mL), and the resultant solution was stirred at room temperature for 23 hours. 1 M hydrochloric acid was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=9:1→0:1). In this manner, the title compound (80.7 mg) having the physical property values shown below was produced. HPLC retention time (min): 1.00;
$^1$H-NMR (CDCl$_3$): δ 1.97-2.04, 2.37-2.42, 2.64-2.67, 2.96-2.99, 3.19, 4.05, 6.22, 6.33, 6.73, 6.85-6.92, 7.06-7.08, 7.13-7.17, 7.21, 7.41-7.45, 7.50-7.54, 7.76-7.78.

Example 95(2): 3-[2-[(E)-5-[3-(Benzenesulfonamido)phenyl]pent-4-enoxy]phenyl]propanamide The same designed procedure as in Example 31 was carried out using, in place of 3-[2-[(E,3R)-5-[3-(benzenesulfonamido)phenyl]-3-hydroxypent-4-enoxy]phenyl]propanoic acid used in Example 31, the compound produced in Example 84. In this manner, the title compound having the physical property values shown below was produced.

HPLC retention time (min): 0.98;
$^1$H-NMR (CDCl$_3$): δ 1.95-2.02, 2.40-2.45, 2.60-2.64, 3.03-3.07, 4.04, 5.55, 5.82, 6.29, 6.34-6.41, 6.86, 6.89-6.95, 7.03-7.06, 7.11-7.22, 7.41-7.44, 7.49-7.53, 7.82-7.85, 8.25.

Example 95(3): N-[3-[(E)-5-[2-(2-Cyanoethyl)phenoxy]pent-1-enyl]phenyl]benzenesulfonamide Pyridine (0.052 mL) and trifluoroacetic acid anhydride (67.8 mg) were added to a solution of the compound produced in Example 95(2) (100 mg) in THF (1 mL) under ice cooling, and the resultant solution was stirred at the same temperature for 1 hour. Methanol and a 1-M aqueous sodium hydroxide solution were added to the reaction solution, and the resultant solution was stirred at room temperature for 1 hour. The reaction solution was poured into water, and the resultant solution was extracted with ethyl acetate. An organic layer was dried over sodium sulfate, and was then concentrated under a reduced pressure. The resultant residue was purified by silica gel column chromatography (hexane: ethyl acetate=4:1→1:1). In this manner, the title compound (91.0 mg) having the physical property values shown below was produced.

HPLC retention time (min): 1.10;
$^1$H-NMR (CDCl$_3$): δ 1.95-2.02, 2.37-2.42, 2.61-2.65, 2.95-2.99, 4.03, 6.20, 6.34, 6.49, 6.84-6.94, 7.05-7.25, 7.41-7.46, 7.51-7.55, 7.75-7.78.

Example 95(4): N-[3-[(E)-5-[2-[2-(1H-Tetrazol-5-yl)ethyl]phenoxy]pent-1-enyl]phenyl]benzenesulfonamide trimethylsilyl azide (44.0 mg) and dibutyltin oxide (24.0 mg) were added to a solution of the compound produced in Example 95(3) (43.0 mg) in toluene (0.5 mL), and the resultant solution was stirred at 100° C. overnight. The reaction solution was purified by silica gel column chromatography (hexane: ethyl acetate: methanol=50:50:3→0:100:3). In this manner, the title compound (15.0 mg) having the physical property values shown below was produced.

HPLC retention time (min): 0.99;
$^1$H-NMR (CDCl$_3$): δ 1.92-1.99, 2.34-2.39, 3.11-3.15, 3.30-3.34, 4.02, 6.20, 6.30, 6.83-6.90, 7.30-7.22, 7.39-7.43, 7.49-7.53, 7.76-7.78.

Example 95(5): Isobutyl (E)-(3-(5-(2-(3-amino-3-oxopropyl)phenoxy)pent-1-en-1-yl)phenyl) (phenylsulfonyl)carbamate Triethylamine (0.20 mL) and isobutyl chloroformate (110 mg) were added to a solution of the compound produced in Example 84 (100 mg) in THF (1 mL) under ice cooling, and the reaction mixture was stirred at room temperature for 10 minutes. Ammonia (a 28% aqueous solution, 0.5 mL) was added to the reaction solution under ice cooling, and the resultant solution was stirred at room temperature for 30 minutes. The reaction solution was poured into water, and the resultant solution was extracted with ethyl acetate. An organic layer was dried over sodium sulfate, and was then concentrated under a reduced pressure. The resultant residue was purified by silica gel column chromatography (hexane: ethyl acetate=1:1→0:1). In this manner, the title compound (120 mg) having the physical property value shown below was produced.

HPLC retention time (min): 1.11.

Example 95(6): N-[3-[(E)-5-[2-[2-(1H-1,2,4-Triazol-5-yl)ethyl]phenoxy]pent-1-enyl]phenyl]benzenesulfonamide N,N-Dimethylformamide dimethyl acetal (0.5 mL) was added to a solution of the compound produced in Example 95(5) (120 mg) in DMF (0.2 mL), and the resultant solution was stirred at 100° C. for 4 hours. The reaction solution was concentrated under a reduced pressure, then acetic acid (1 mL) and hydrazine monohydrate (0.1 mL) were added to the solution, and the resultant solution was stirred at 100° C. for 3 hours. The solution was cooled to room temperature, then a saturated aqueous sodium bicarbonate solution was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=1:1→0:1). A 2-M aqueous sodium hydroxide solution (0.2 mL) was added to a solution of the resultant residue (48 mg) in methanol (1 mL), and the resultant solution was stirred at room temperature overnight. The reaction mixture was neutralized with a 1-M aqueous sodium dihydrogen phosphate solution, and the resultant solution was extracted with ethyl acetate. An organic layer was dried over sodium sulfate, and was then concentrated under a reduced pressure. The resultant residue was purified by silica gel column chromatography (hexane: ethyl acetate: methanol=50:50:3→0:100:3). In this manner, the title compound (24.0 mg) having the physical property values shown below was produced.

HPLC retention time (min): 0.90;
$^1$H-NMR (CDCl$_3$): δ 1.95-2.02, 2.38-2.43, 3.08-3.18, 4.04, 6.22, 6.32, 6.84-6.89, 6.94-6.97, 7.02, 7.07-7.21, 7.39-7.43, 7.49-7.53, 7.67, 7.75-7.77, 8.04.

Example 96: Isopropyl (E)-3-(2-((4-hydroxy-6-(3-(phenylsulfonamido)phenyl)hex-5-en-1-yl)oxy)phenyl)propanoate The same designed procedures as in Example 2→Example 3→Example 4→Example 5→Example 7→Example 8→Example 10 were carried out using, in place of 2-(2-bromoethyl)-1,3-dioxane used in Example 2, 2-(3-bromopropyl)-1,3-dioxane. In this manner, the title compound having the physical property value shown below was produced.

TLC: Rf 0.43 (hexane: ethyl acetate=1:1).

Example 97: 3-[2-[(E)-6-[3-(Benzenesulfonamido) phenyl]-4-hydroxyhex-5-enoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy] phenyl]propanoate used in Example 11, the compound produced in Example 96. In this manner, the title compound having the physical property values shown below was produced.

HPLC retention time (min): 0.96;
$^1$H-NMR (CDCl$_3$): δ 1.82-1.95, 2.67-2.71, 2.98-3.02, 3.97-4.04, 4.36-4.40, 6.20, 6.52, 6.83, 6.87-6.91, 7.00-7.04, 7.10-7.21, 7.40-7.45, 7.49-7.54, 7.66, 7.78-7.81.

Example 98: Isopropyl (R,E)-3-(2-((4-hydroxy-6-(3-(phenylsulfonamido)phenyl)hex-5-en-1-yl)oxy) phenyl)propanoate, or isopropyl (S,E)-3-(2-((4-hydroxy-6-(3-(phenylsulfonamido)phenyl)hex-5-en-1-yl)oxy)phenyl)propanoate The compound produced in Example 96 was subjected to optical resolution employing SFC (column used: Daicel Corporation CHIRALPAK-IC (20 mm×250 mm), mobile phase: CO$_2$: methanol=85:15, flow rate: 100 mL/min, pressure: 120 bar, wavelength: 220 nm, column temperature: 35° C.). Optically active substances of Example 96 produced under the optical resolution conditions were analyzed by SFC (column used: Daicel Corporation CHIRALPAK-IC(10 mm×250 mm), mobile phase: CO$_2$: methanol=85:15, flow rate: 30 mL/min, pressure: 120 bar, wavelength: 220 nm, column temperature: 35° C.). As a result, the retention times for a first peak and a second peak were 13.6 minutes and 15.8 minutes, respectively.

Example 99: (R)-3-[2-[(E)-6-[3-(Benzenesulfonamido)phenyl]-4-hydroxyhex-5-enoxy]phenyl]propanoic acid, or (S)-3-[2-[(E)-6-[3-(benzenesulfonamido)phenyl]-4-hydroxyhex-5-enoxy]phenyl] propanoic acid The same designed procedure as in Example 11 was carried out using, in place of propan-2-yl 3-[2-[(E,3R)-5-[3-(benzenesulfonamido)phenyl]-3-hydroxypent-4-enoxy] phenyl]propanoate used in Example 11, the optically active substance corresponding to the first peak which had been produced in Example 98. In this manner, the title compound having the physical property values shown below was produced.

HPLC retention time (min): 0.96;
$^1$H-NMR (CDCl$_3$): δ 1.82-1.95, 2.67-2.71, 2.98-3.02, 3.97-4.04, 4.36-4.40, 6.20, 6.52, 6.83, 6.87-6.91, 7.00-7.04, 7.10-7.21, 7.40-7.45, 7.49-7.54, 7.66, 7.78-7.81.

Example 100: (R)-3-[2-[(E)-6-[3-(Benzenesulfonamido)phenyl]-4-hydroxyhex-5-enoxy]phenyl]propanoic acid, or (S)-3-[2-[(E)-6-[3-(benzenesulfonamido)phenyl]-4-hydroxyhex-5-enoxy]phenyl] propanoic acid The same designed procedure as in Example 11 was carried out using, in place of propan-2-yl 3-[2-[(E,3R)-5-[3-(benzenesulfonamido)phenyl]-3-hydroxypent-4-enoxy] phenyl]propanoate used in Example 11, the optically active substance corresponding to the second peak which had been produced in Example 98. In this manner, the title compound having the physical property values shown below was produced.

HPLC retention time (min): 0.96;
$^1$H-NMR (CDCl$_3$): δ 1.82-1.95, 2.67-2.71, 2.98-3.02, 3.97-4.04, 4.36-4.40, 6.20, 6.52, 6.83, 6.87-6.91, 7.00-7.04, 7.10-7.21, 7.40-7.45, 7.49-7.54, 7.66, 7.78-7.81.

Example 101: 3-[2-[6-[3-(Benzenesulfonamido) phenyl]-4-hydroxyhexoxy]phenyl]propanoic acid The same designed procedure as in Example 33 was carried out using, in place of 3-[2-[(E,3R)-5-[3-(benzenesulfonamido)phenyl]-3-hydroxypent-4-enoxy]phenyl]propanoic acid used in Example 33, the compound produced in Example 97. In this manner, the title compound having the physical property values shown below was produced.

HPLC retention time (min): 0.96;
$^1$H-NMR (CDCl$_3$): δ 1.58-1.67, 1.72-2.00, 2.65-2.09, 2.93-3.07, 3.59-3.65, 3.95-4.05, 6.82-6.93, 6.98-7.01, 7.12-7.22, 7.40-7.45, 7.50-7.54, 7.77-7.80.

Example 102: (R)-3-[2-[6-[3-(Benzenesulfonamido) phenyl]-4-hydroxyhexoxy]phenyl]propanoic acid or (S)-3-[2-[6-[3-(benzenesulfonamido)phenyl]-4-hydroxyhexoxy]phenyl]propanoic acid The compound produced in Example 101 was subjected to optical resolution employing SFC (column used: Daicel Corporation CHIRALPAK-IB (20 mm×250 mm), mobile phase: $CO_2$: acetonitrile: methanol=80:18:2, flow rate: 100 mL/min, pressure: 120 bar, wavelength: 220 nm, column temperature: 35° C.). Optically active substances of Example 101 produced under the optical resolution conditions were analyzed by SFC (column used: Daicel Corporation CHIRALPAK-IB (20 mm×250 mm), mobile phase: $CO_2$: acetonitrile: methanol=80:18:2, flow rate: 100 mL/min, pressure: 120 bar, wavelength: 220 nm, column temperature: 35° C.). As a result, the retention times for a first peak and a second peak were 9.6 minutes and 12.3 minutes, respectively.

Example 103: 3-[2-[6-[3-(Benzenesulfonamido) phenyl]-4-oxohexoxy]phenyl]propanoic acid The same designed procedures as in Example 78→Example 79 were carried out using, in place of 3-[2-[(E,3R)-5-[3-(benzenesulfonamido)phenyl]-3-hydroxypent-4-enoxy]phenyl]propanoic acid used in Example 78, the compound produced in Example 97. In this manner, the title compound having the physical property values shown below was produced.

TLC: Rf 0.45 (hexane: ethyl acetate=1:2);

$^1$H-NMR ($CDCl_3$): δ 2.01-2.10, 2.61-2.75, 2.83, 2.96, 3.96, 6.78-6.82, 6.86-6.91, 6.96, 7.10, 7.14-7.21, 7.42, 7.51, 7.68-7.84.

Examples 104(1) to (2)

The same designed procedures as in Example 81→Example 82→Example 83→Example 84 were carried out using, in place of isopropyl 3-(2-hydroxyphenyl)propanoate used in Example 81, corresponding phenol compounds. In this manner, the following compounds of Examples were produced.

Example 104(1): 2-[2-[(E)-5-[3-(Benzenesulfonamido)phenyl]pent-4-enoxy]phenyl]acetic acid HPLC retention time (min): 1.01;

$^1$H-NMR ($CDCl_3$): δ 1.89-1.96, 2.33-2.38, 3.67, 4.01, 6.14, 6.29, 6.68, 6.85-6.94, 7.00-7.28, 7.39-7.43, 7.48-7.52, 7.74-7.77.

Example 104(2): 4-[2-[(E)-5-[3-(Benzenesulfonamido)phenyl]pent-4-enoxy]phenyl]butanoic acid HPLC retention time (min): 1.07;

$^1$H-NMR ($CDCl_3$): δ 1.93-2.00, 2.37-2.43, 2.70, 4.00, 6.21, 6.33, 6.82-6.92, 7.04-7.19, 7.40-7.44, 7.49-7.53, 7.75-7.78.

Examples 105(1) to (3)

The same designed procedure as in Example 81→Example 82→Example 83→Example 84 were carried out using, in place of 5-chloro-1-penthyne used in Example 81, corresponding halide compounds. In this manner, the following compounds of Examples were produced.

Example 105(1): 3-[2-[(E)-4-[3-(Benzenesulfonamido)phenyl]but-3-enoxy]phenyl]propanoic acid HPLC retention time (min): 1.01;

$^1$H-NMR ($CD_3OD$): δ 2.52-2.56, 2.67-2.71, 2.88-2.92, 4.10-4.13, 6.31, 6.46, 6.86, 6.93-6.98, 7.09-7.20, 7.44-7.49, 7.52-7.57, 7.75-7.78.

Example 105(2): 3-[2-[(E)-6-[3-(Benzenesulfonamido)phenyl]hex-5-enoxy]phenyl]propanoic acid TLC: Rf 0.44 (hexane: ethyl acetate=1:1);

$^1$H-NMR ($CDCl_3$): δ 1.65-1.76, 1.77-1.88, 2.25-2.31, 2.69-2.75, 2.99-3.05, 3.99, 6.18, 6.33, 6.83, 6.89, 6.95-7.00, 7.10-7.21, 7.44, 7.53, 7.67, 7.81.

Example 105(3): 3-[2-[(E)-7-[3-(Benzenesulfonamido)phenyl]hept-6-enoxy]phenyl]propanoic acid TLC: Rf 0.44 (hexane: ethyl acetate=1:1);

$^1$H-NMR ($CDCl_3$): δ 1.61-1.73, 1.77-1.88, 2.27, 2.76-2.82, 3.02-3.07, 4.01, 6.29-6.33, 6.83-6.93, 7.08-7.23, 7.45, 7.53, 7.84, 8.75.

Example 106: Methyl 3-(2-((4-hydroxy-5-(3-(phenylsulfonamido)phenyl)pentyl)oxy)phenyl)propanoate The compound produced in Example 84 (200 mg) was dissolved in ethyl acetate (1 mL). Methanol (1 mL) and trimethylsilyldiazomethane (a 2-M hexane solution, 0.3 mL) were added to the reaction solution, and the resultant solution was stirred at room temperature overnight. The reaction solution was concentrated under a reduced pressure, and the resultant residue was dissolved in dichloromethane (2 mL). A saturated aqueous sodium bicarbonate solution (2 mL) and m-chloroperoxybenzoic acid (171 mg) were added to the solution, and the resultant solution was stirred at room temperature for 5 hours. A saturated aqueous sodium thiosulfate solution was added to the reaction solution, and the resultant solution was extracted with ethyl acetate. An organic layer was washed with water and saturated saline, was then dried over sodium sulfate, and was then concentrated under a reduced pressure. The residue was dissolved in methanol (2 mL), 5% palladium-carbon (20 mg) was then added to the solution, and the resultant solution was stirred at room temperature for 3 hours under a hydrogen atmosphere. The reaction solution was filtrated, a filtrate was concentrated under a reduced pressure, and the resultant residue was purified by silica gel column chromatography (hexane: ethyl acetate=70:30→ethyl acetate). In this manner, the title compound (53 mg) having the physical property value shown below was produced.

TLC: Rf 0.31 (hexane: ethyl acetate=1:1).

Example 107: 3-[2-[5-[3-(Benzenesulfonamido) phenyl]-4-hydroxypentoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy] phenyl]propanoate used in Example 11, the compound produced in Example 106. In this manner, the title compound having the physical property values shown below was produced.

TLC: Rf 0.60 (ethyl acetate);

$^1$H-NMR ($CDCl_3$): δ 1.50-1.68, 1.68-1.74, 1.77-2.00, 2.61-2.70, 2.72-2.79, 2.92-2.99, 3.87, 3.95-4.05, 6.82-7.03, 7.15-7.21, 7.38-7.45, 7.48-7.53, 7.77.

Example 108: Ethyl 3-(2-(4-oxobutyl)phenyl)propanoate

Sodium hydrogen carbonate (0.56 g) and 1,1,1-triacetoxy-1,1-dihydro-1,2-benziodoxol-3(1H)-one (CAS Registry Number: 87413-09-0) (1.13 g) were added to a solution of ethyl 3-[2-(4-hydroxybutyl)phenyl]propanoate (CAS Registry Number: 864677-94-1) (0.56 g) in dichloromethane (9 mL) at 0° C., and the resultant reaction mixture was stirred at room temperature for 1 hour. The reaction mixture was poured into a saturated aqueous sodium bicarbonate solution, and the resultant solution was then extracted with dichloromethane. An organic layer washes with a saturated aqueous sodium thiosulfate solution, was then dried over sodium sulfate, and was then concentrated under a reduced pressure. The resultant residue was purified by silica gel column chromatography (hexane: ethyl acetate=4:1). In this manner, the title compound (0.34 g) having the physical property value shown below was produced.

TLC: Rf 0.30 (hexane: ethyl acetate=4:1).

Example 109: 3-[2-[(E)-6-[3-(Benzenesulfonamido)phenyl]-4-hydroxyhex-5-enyl]phenyl]propanoic acid The same designed procedures as in Example 4→Example 5→Example 7→Example 8→Example 10→Example 11 were carried out using, in place of isopropyl 3-(2-(3-oxopropoxy)phenyl)propanoate used in Example 4, the compound produced in Example 108. In this manner, the title compound having the physical property values shown below was produced.

HPLC retention time (min): 0.95;

$^1$H-NMR (CDCl$_3$): δ 1.60-1.79, 2.66-2.72, 2.97-3.01, 4.30-4.35, 6.16, 6.49, 6.98-7.07, 7.13-7.17, 7.40-7.53, 7.77-7.79.

Example 110: (R)-3-[2-[(E)-6-[3-(Benzenesulfonamido)phenyl]-4-hydroxyhex-5-enyl]phenyl]propanoic acid, or (S)-3-[2-[(E)-6-[3-(benzenesulfonamido)phenyl]-4-hydroxyhex-5-enyl]phenyl]propanoic acid

[Formula 53]

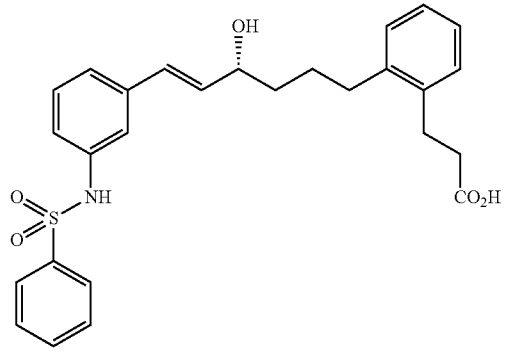

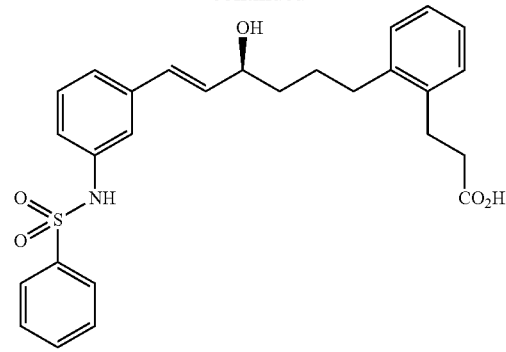

The compound produced in Example 109 was subjected to optical resolution employing SFC (column used: Daicel Corporation CHIRALPAK-IC (20 mm×250 mm), mobile phase: CO$_2$: methanol=85:15, flow rate: 100 mL/min, pressure: 120 bar, wavelength: 220 nm, column temperature: 35° C.). Optically active substances of Example 109 produced under the optical resolution conditions were analyzed by SFC (column used: Daicel Corporation CHIRALPAK-IC(10 mm×250 mm), mobile phase: CO$_2$: methanol=85:15, flow rate: 30 mL/min, pressure: 100 bar, wavelength: 220 nm, column temperature: 35° C.). As a result, the retention times for a first peak and a second peak were 12.4 minutes and 14.4 minutes, respectively.

Example 111: 3-[2-[6-[3-(Benzenesulfonamido)phenyl]-4-hydroxyhexyl]phenyl]propanoic acid The same designed procedure as in Example 33 was carried out using, in place of 3-[2-[(E,3R)-5-[3-(benzenesulfonamido)phenyl]-3-hydroxypent-4-enoxy]phenyl]propanoic acid used in Example 33, the compound produced in Example 109. In this manner, the title compound having the physical property values shown below was produced.

HPLC retention time (min): 0.95;

$^1$H-NMR (CD$_3$OD): δ 1.37-1.61, 2.39-2.58, 2.84, 6.79-6.81, 6.98-7.08, 7.30-7.42, 7.61-7.63.

Example 112: 3-[2-[6-[3-(Benzenesulfonamido)phenyl]-4-oxohexyl]phenyl]propanoic acid

[Formula 54]

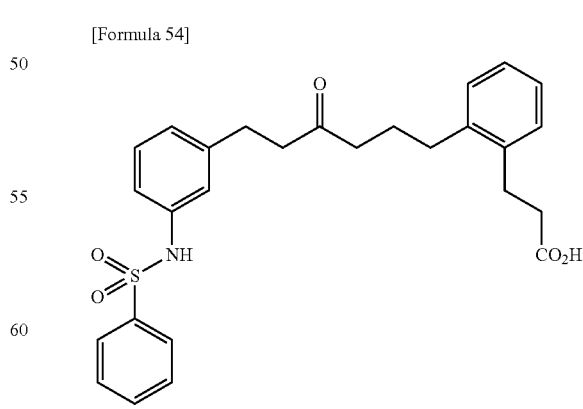

The same designed procedures as in Example 78→Example 79 were carried out using, in place of 3-[2-[(E,3R)-5-[3-(benzenesulfonamido)phenyl]-3-hydroxypent- 4-enoxy]phenyl]propanoic acid used in Example 78, the compound produced in Example 109. In this manner, the title compound having the physical property values shown below was produced.

HPLC retention time (min): 1.00;
$^1$H-NMR (CD$_3$OD): δ 1.75-1.83, 2.44-2.47, 2.54-2.61, 2.65-2.69, 2.75-2.79, 2.92-2.96, 6.90-6.94, 7.09-7.14, 7.18, 7.43-7.48, 7.54, 7.74-7.76.

Example 113: Isopropyl 3-(2-((5-(3-(phenylsulfonamido)phenyl)pent-4-yn-1-yl)oxy)phenyl)propanoate Triethylamine (6 mL), bis(triphenylphosphine)palladium (II) dichloride (100 mg) and copper (I) iodide (50 mg) were added to a solution of the compound produced in Example 81 (1.5 g) and the compound produced in Example 9 (1.7 g) in DMF (6 mL), and the resultant solution was stirred at 60° C. overnight. Water was added to the reaction solution, then the resultant solution was extracted with ethyl acetate. An organic layer was washed with saturated saline, was then dried over magnesium sulfate, and was then concentrated under a reduced pressure. The resultant residue was purified by silica gel column chromatography (hexane: ethyl acetate=9:1→0:1). In this manner, the title compound (1.57 g) having the physical property value shown below was produced.

TLC: Rf 0.39 (hexane: ethyl acetate=2:1).

Example 114: 3-[2-[5-[3-(Benzenesulfonamido) phenyl]pent-4-ynoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy] phenyl]propanoate used in Example 11, the compound produced in Example 113. In this manner, the title compound having the physical property values shown below was produced.

HPLC retention time (min): 1.00;
$^1$H-NMR (CD$_3$OD): δ 2.06-2.12, 2.55-2.59, 2.64-2.67, 2.92-2.96, 4.13-4.16, 6.87, 6.95, 7.03-7.07, 7.12-7.20, 7.45-7.50, 7.56, 7.74-7.77.

Example 115: Isopropyl (R)-3-(2-((5-(3-(phenylsulfonamido)phenyl)-3-((trimethylsilyl)oxy)pent-4-yn-1-yl)oxy)phenyl)propanoate The same designed procedure as in Example 113 was carried out using, in place of isopropyl 3-(2-(pent-4-yn-1-yl oxy)phenyl)propanoate used in Example 113, the compound produced in Example 7. In this manner, the title compound having the physical property value shown below was produced.

HPLC retention time (min): 1.12.

Example 116: Isopropyl (R)-3-(2-((3-hydroxy-5-(3-(phenylsulfonamido)phenyl)pent-4-yn-1-yl)oxy) phenyl)propanoate TBAF (a 1.0-M THF solution, 0.48 mL) was added to a solution of the compound produced in Example 115 (170 mg) in THF (1 mL) at room temperature, and the resultant solution was stirred at the same temperature for 20 minutes. The reaction solution was purified by silica gel column chromatography (hexane: ethyl acetate=7:3→hexane:ethyl acetate=1:1). In this manner, the title compound (82.8 mg) having the physical property value shown below was produced.

HPLC retention time (min): 1.12.

Example 117: 3-[2-[(3R)-5-[3-(Benzenesulfonamido)phenyl]-3-hydroxypent-4-ynoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy] phenyl]propanoate used in Example 11, the compound produced in Example 116. In this manner, the title compound having the physical property values shown below was produced.

HPLC retention time (min): 0.93;
$^1$H-NMR (CD$_3$OD): δ 2.19-2.30, 2.57-2.60, 2.91-2.95, 4.16-4.26, 4.85, 6.88, 6.96, 7.07-7.22, 7.46-7.51, 7.57, 7.75-7.77.

Example 118: 3-[2-[5-[3-(Benzenesulfonamido) phenyl]pentoxy]phenyl]propanoic acid

[Formula 55]

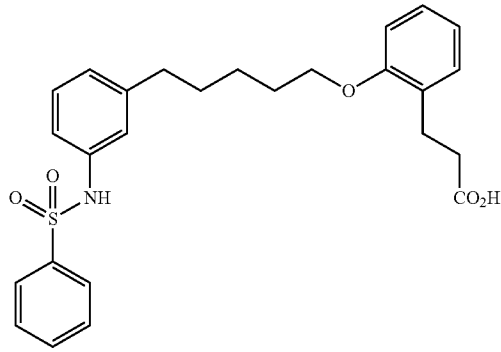

The same designed procedure as in Example 33 was carried out using, in place of 3-[2-[(E,3R)-5-[3-(benzenesulfonamido)phenyl]-3-hydroxypent-4-enoxy]phenyl]propanoic acid used in Example 33, the compound produced in Example 114. In this manner, the title compound having the physical property values shown below was produced.

TLC: Rf 0.42 (hexane: ethyl acetate=1:2);
$^1$H-NMR (CDCl$_3$): δ 1.42-1.49, 1.58-1.65, 1.75-1.82, 2.55, 2.67, 2.95, 3.95, 6.80-6.97, 7.10-7.21, 7.27, 7.40, 7.49, 7.76.

Example 119: Isopropyl (Z)-3-(2-((5-(3-(phenylsulfonamido)phenyl)pent-4-en-1-yl)oxy)phenyl) propanoate Lindlar's catalyst (containing palladium in an amount of 5% by weight) (10.0 mg) and quinoline (12.8 mg) were added to a solution of the compound produced in Example 113 (100 mg) in ethyl acetate (10 mL) at room temperature, and the resultant solution was stirred at the same temperature for 5 hours under a hydrogen atmosphere. The reaction solution was purified by silica gel column chromatography (hexane: ethyl acetate=7:3→1:1). In this manner, the title compound (92.3 mg) having the physical property value shown below was produced.

HPLC retention time (min): 1.23.

Example 120: 3-[2-[(Z)-5-[3-(Benzenesulfonamido)phenyl]pent-4-enoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the compound produced in Example 119. In this manner, the title compound having the physical property values shown below was produced.

HPLC retention time (min): 1.10;
$^1$H-NMR (CD$_3$OD): δ 1.89-1.95, 2.37-2.43, 2.49-2.53, 2.83-2.87, 3.97-4.00, 5.74, 6.38, 6.83-6.89, 6.96-7.02, 7.13-7.19, 7.41-7.45, 7.51, 7.72-7.76.

Example 121: 3-[2-[(Z,3R)-5-[3-(Benzenesulfonamido)phenyl]-3-hydroxypent-4-enoxy]phenyl]propanoic acid The same designed procedures as in Example 119→Example 11 were carried out using, in place of isopropyl 3-(2-((5-(3-(phenylsulfonamido)phenyl)pent-4-yn-1-yl)oxy)phenyl)propanoate used in Example 119, the compound produced in Example 116. In this manner, the title compound having the physical property values shown below was produced.

HPLC retention time (min): 0.92;
$^1$H-NMR (CD$_3$OD): δ 2.00-2.07, 2.44-2.48, 2.77-2.80, 4.02, 4.11, 4.75, 5.72, 6.46, 6.83-6.88, 6.92-7.04, 7.12-7.18, 7.42-7.47, 7.52, 7.74-7.77.

Example 122: Ethyl (E)-3-(2-(3-(benziloxy)-2-hydroxypropoxy)phenyl)acrylate

Benzyl glycidyl ether (6.57 g) was added to a solution of ethyl (E)-3-(2-hydroxyphenyl)prop-2-enoate (CAS Registry Number: 6236-62-0) (1.92 g) and diisopropylethylamine (0.69 mL) in hexamethylphorphoramide (20 mL), and the reaction mixture was stirred at 80° C. for 19 hours. The reaction solution was cooled to room temperature, and was then poured into water, and the resultant solution was extracted with ethyl acetate. An organic layer was washed with saturated saline, was then dried over sodium sulfate, and was then concentrated under a reduced pressure. The resultant residue was purified by silica gel column chromatography (hexane: ethyl acetate=2:1). In this manner, the title compound (2.66 g) having the physical property value shown below was produced.

TLC: Rf 0.33 (hexane: ethyl acetate=2:1).

Example 123: Ethyl (E)-3-(2-(3-(benziloxy)-2-((tert-butyldimethylsilyl)oxy)propoxy)phenyl)acrylate tert-Butyldimethylsilyl chloride (330 mg) was added to a solution of the compound produced in Example 122 (300 mg) and imidazole (200 mg) in DMF (3 mL) at 0° C., and the reaction mixture was stirred at room temperature for 5 days. The reaction mixture was poured into water, and the resultant solution as extracted with ethyl acetate. An organic layer was washed with saturated saline, was then dried over sodium sulfate, and was then concentrated under a reduced pressure. The resultant residue was purified by silica gel column chromatography (hexane: ethyl acetate=9:1). In this manner, the title compound (380 mg) having the physical property value shown below was produced.

TLC: Rf 0.41 (hexane: ethyl acetate=9:1).

Example 124: Ethyl 3-(2-(2-((tert-butyldimethylsilyl)oxy)-3-hydroxypropoxy)phenyl)propanoate A solution of the compound produced in Example 123 (380 mg) and 5% palladium on carbon (50% wet, 180 mg) in ethanol (8 mL) was stirred at room temperature for 1.5 hours under a hydrogen atmosphere. The reaction mixture was filtrated through Celite (trade name), and a filtrate was concentrated. In this manner, the title compound (290 mg) having the physical property value shown below was produced.

TLC: Rf 0.34 (hexane: ethyl acetate=4:1).

Example 125: Ethyl 3-(2-(2-((tert-Butyldimethylsilyl)oxy)-3-oxopropoxy)phenyl)propanoate 1,1,1-Triacetoxy-1,1-Dihydro-1,2-benziodoxol-3(1H)-one (390 mg) was added to a solution of the compound produced in Example 124 (290 mg) and sodium hydrogen carbonate (190 mg) in methylene chloride (3 mL) at 0° C., and the reaction mixture was stirred at room temperature for 1 hour. The reaction mixture was poured into a saturated aqueous sodium bicarbonate solution, and the resultant solution was extracted with methylene chloride. An organic layer washes with a saturated aqueous sodium thiosulfate solution, was then dried over sodium sulfate, and was then concentrated under a reduced pressure. The resultant residue was purified by silica gel column chromatography (hexane: ethyl acetate=4:1). In this manner, the title compound (250 mg) having the physical property value shown below was produced.

TLC: Rf 0.40 (hexane: ethyl acetate=4:1).

Example 126: Ethyl (E)-3-(2-((2-hydroxy-4-(3-(phenylsulfonamido)phenyl)but-3-en-1-yl)oxy)phenyl)propanoate The same designed procedures as in Example 45→Example 55→Example 56→Example 116 were carried out using, in place of (R)-4-((4-methoxybenzil)oxy)-1-oxobutan-2-yl benzoate used in Example 45, the compound produced in Example 125. In this manner, the title compound having the physical property value shown below was produced.

TLC: Rf 0.43 (hexane: ethyl acetate=1:1).

Example 127: 3-[2-[(E)-4-[3-(Benzenesulfonamido)phenyl]-2-hydroxybut-3-enoxy]phenyl]propanoic acid

[Formula 56]

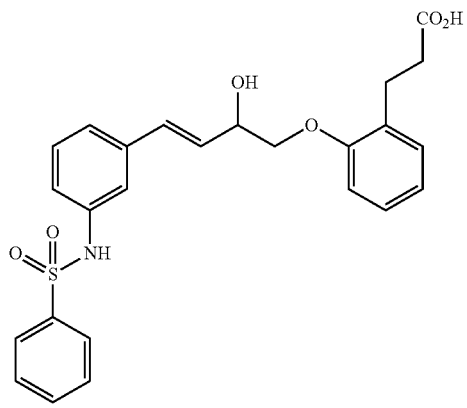

The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the compound produced in Example 126. In this manner, the title compound having the physical property values shown below was produced.

HPLC retention time (min): 0.95;

$^1$H-NMR (CDCl$_3$): δ 2.59-2.72, 2.93-3.08, 4.00, 4.17, 4.68-4.72, 6.40, 6.64, 6.84, 6.90-6.94, 7.03-7.07, 7.13-7.22, 7.38-7.52, 7.76-7.79.

Example 128: Ethyl (S,E)-3-(2-((2-hydroxy-4-(3-(phenylsulfonamido)phenyl)but-3-en-1-yl)oxy)phenyl)propanoate, or ethyl (R,E)-3-(2-((2-hydroxy-4-(3-(phenylsulfonamido)phenyl)but-3-en-1-yl)oxy)phenyl)propanoate The compound produced in Example 126 was subjected to optical resolution employing SFC (column used: Daicel Corporation CHIRALPAK-IB (20 mm×250 mm), mobile phase: CO$_2$: 2-propanol=83:17, flow rate: 100 mL/min, pressure: 120 bar, wavelength: 220 nm, column temperature: 35° C.). Optically active substances of Example 126 produced under the under the optical resolution conditions were analyzed by SFC (column used: Daicel Corporation CHIRALPAK-IB(10 mm×250 mm), mobile phase: CO$_2$: 2-propanol=83:17, flow rate: 30 mL/min, pressure: 100 bar, wavelength: 220 nm, column temperature: 35° C.). As a result, the retention times for a first peak and a second peak were 12.6 minutes and 14.6 minutes, respectively.

Example 129: 3-[2-[(E)-4-[3-(Benzenesulfonamido)phenyl]-2-hydroxybut-3-enoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the optically active substance corresponding to the first peak which had been produced in Example 128. In this manner, the title compound having the physical property values shown below was produced.

HPLC retention time (min): 0.95;

$^1$H-NMR (CDCl$_3$): δ 2.59-2.72, 2.93-3.08, 4.00, 4.17, 4.68-4.72, 6.40, 6.64, 6.84, 6.90-6.94, 7.03-7.07, 7.13-7.22, 7.38-7.52, 7.76-7.79.

Example 130: 3-[2-[(E)-4-[3-(Benzenesulfonamido)phenyl]-2-hydroxybut-3-enoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the optically active substance corresponding to the second peak which had been produced in Example 128. In this manner, the title compound having the physical property values shown below was produced.

HPLC retention time (min): 0.95;

$^1$H-NMR (CDCl$_3$): δ 2.59-2.72, 2.93-3.08, 4.00, 4.17, 4.68-4.72, 6.40, 6.64, 6.84, 6.90-6.94, 7.03-7.07, 7.13-7.22, 7.38-7.52, 7.76-7.79.

Example 131: N-(3-Bromophenyl)-N-(phenylsulfonyl)benzenesulfonamide

Triethylamine (1.6 mL), DMAP (177 mg) and benzenesulfonic acid anhydride (1.9 g) were added to a solution of 3-bromoaniline (500 mg) in dichloromethane (10 mL), and the resultant solution was stirred at room temperature for 18 hours. Water was added to the reaction mixture, and the resultant solution was extracted with dichloromethane. An organic layer was dried over sodium sulfate, and was then concentrated under a reduced pressure. The resultant residue was purified by silica gel column chromatography (hexane: ethyl acetate=4:1). In this manner, the title compound (950 mg) having the physical property value shown below was produced.

TLC: Rf 0.30 (hexane: ethyl acetate=4:1).

Example 132: N-(3-(4-Hydroxybut-1-in-1-yl)phenyl)-N-(phenylsulfonyl)benzenesulfonamide Triethylamine (1.5 mL), 3-butyn-1-ol (220 mg), copper iodide (40 mg) and bis(triphenylphosphine palladium) dichloride (147 mg) were added to a solution of the compound produced in Example 131 (949 mg) in DMF (4 mL), and the resultant solution was stirred at 80° C. for 2 hours. A saturated aqueous ammonium chloride solution was added to the reaction mixture, and the resultant solution was extracted with ethyl acetate. An organic layer was washed with water, was then dried over sodium sulfate, and was then concentrated under a reduced pressure. The resultant residue was purified by silica gel column chromatography (hexane: ethyl acetate=2:1). In this manner, the title compound (771 mg) having the physical property value shown below was produced.

TLC: Rf 0.30 (hexane: ethyl acetate=2:1).

Example 133: N-(3-(4-Hydroxybutyl)phenyl)-N-(phenylsulfonyl)benzenesulfonamide

A solution of the compound produced in Example 132 (600 mg) and 20% palladium hydroxide on carbon (50% wet, 150 mg) in methanol (5 mL) was stirred at room temperature for 9 hours under a hydrogen atmosphere. The reaction mixture was filtrated through Celite (trade name), and a filtrate was concentrated. In this manner, the title compound (575 mg) having the physical property value shown below was produced.

HPLC retention time (min): 1.00.

Example 134: 3-[3-[4-[3-(Benzenesulfonamido)phenyl]butoxy]phenyl]propanoic acid

Methyl 3-(3-hydroxyphenyl)propanoate (22 mg), DIAD (82 mg) and triphenylphosphine (40 mg) were added to a solution of the compound produced in Example 133 (45 mg) in THF (0.5 mL), and the resultant solution was stirred at room temperature for 2 hours. The reaction mixture was concentrated under a reduced pressure. A 5-N aqueous sodium hydroxide solution (0.4 mL) was added to a solution of the resultant residue in methanol (0.5 mL) and 1,2-dimethoxyethane (0.5 mL), and the resultant solution was stirred at 45° C. for 19 hours. 2 M Hydrochloric acid was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=1:1). In this manner, the title compound (14 mg) having the physical property values shown below was produced.

HPLC retention time (min): 0.97;
$^1$H-NMR (CDCl$_3$): δ 1.66-1.75, 2.61, 2.74, 2.94, 3.94, 6.71-6.73, 6.79-6.86, 6.91-7.00, 7.14, 7.21, 7.37-7.41, 7.47-7.52, 7.72-7.74.

Examples 135(1) to (6) The same designed procedure as in Example 134 was carried out using, in place of methyl 3-(3-hydroxyphenyl)propanoate used in Example 134, corresponding phenol compounds. In this manner, the following compounds of Examples were produced.

Example 135(1): 3-[4-[4-[3-(Benzenesulfonamido)phenyl]butoxy]phenyl]propanoic acid HPLC retention time (min): 0.96;
$^1$H-NMR (CD$_3$OD): δ 1.64-1.74, 2.55-2.61, 2.86, 3.91, 6.80-6.84, 6.92-6.94, 7.11-7.15, 7.42-7.46, 7.50-7.54, 7.73-7.76.

Example 135(2): 4-[2-[4-[3-(Benzenesulfonamido)phenyl]butoxy]phenyl]butanoic acid HPLC retention time (min): 1.00;
$^1$H-NMR (CDCl$_3$): δ 1.77-1.83, 1.96-2.03, 2.48, 2.60, 2.71-2.75, 3.97, 6.82, 6.87-6.90, 7.05-7.07, 7.11-7.20, 7.39-7.43, 7.47-7.52, 7.78-7.81.

Example 135(3): 4-[3-[4-[3-(Benzenesulfonamido)phenyl]butoxy]phenyl]butanoic acid HPLC retention time (min): 0.99;
$^1$H-NMR (CDCl$_3$): δ 1.70-1.74, 1.95-2.02, 2.40, 2.59, 2.65, 3.93, 6.71-6.78, 6.86, 6.93-6.95, 7.12-7.21, 7.39-7.43, 7.48-7.52, 7.74-7.77.

Example 135(4): 2-[2-[4-[3-(Benzenesulfonamido)phenyl]butoxy]phenyl]acetic acid

HPLC retention time (min): 0.94;
$^1$H-NMR (CDCl$_3$): δ 1.68-1.72, 2.57, 3.65, 3.96, 6.80-6.94, 7.13, 7.21-7.24, 7.37-7.42, 7.47-7.52, 7.74-7.77.

Example 135(5): 2-[3-[4-[3-(Benzenesulfonamido)phenyl]butoxy]phenyl]acetic acid

HPLC retention time (min): 0.95;
$^1$H-NMR (CDCl$_3$): δ 1.74-1.77, 2.57-2.60, 3.66, 3.98, 6.83-6.86, 6.91-6.96, 7.11, 7.19-7.26, 7.36-7.43, 7.48-7.52, 7.75-7.78.

Example 135(6): 3-[2-[4-[3-(Benzenesulfonamido)phenyl]butoxy]phenyl]propanoic acid HPLC retention time (min): 0.99;
$^1$H-NMR (CDCl$_3$): δ 1.70-1.86, 2.61, 2.66-2.70, 2.97-3.01, 3.97, 6.82, 6.87-6.91, 7.03-7.06, 7.12-7.21, 7.40-7.44, 7.48-7.53, 7.60, 7.78-7.81.

Example 136: Isopropyl (E)-3-(2-((5-(3-nitrophenyl)-3-oxopent-4-en-1-yl)oxy)phenyl)propanoate The same designed procedures as in Example 10→Example 77 were carried out using, in place of N-(3-bromophenyl)benzenesulfonamide used in Example 10, 3-bromonitrobenzene. In this manner, the title compound having the physical property value shown below was produced.

TLC: Rf 0.43 (hexane: ethyl acetate=2:1).

Example 137: Isopropyl (E)-3-(2-((3,3-difluoro-5-(3-nitrophenyl)pent-4-en-1-yl)oxy)phenyl)propanoate The compound produced in Example 136 (205 mg) was dissolved in dichloromethane (0.4 mL), bis(2-methoxyethyl)aminosulfur trifluoride (1.5 mL) was then added to the solution, and the resultant solution was stirred at room temperature for 3 days. The reaction solution was poured into a saturated aqueous sodium bicarbonate solution, and the resultant solution was extracted with ethyl acetate. An organic layer was washed with saturated saline, was then dried over magnesium sulfate, and was then concentrated under a reduced pressure. The resultant residue was purified by silica gel column chromatography (hexane: ethyl acetate=90:10→ethyl acetate). In this manner, the title compound (29 mg) having the physical property value shown below was produced.

TLC: Rf 0.66 (hexane: ethyl acetate=2:1).

Example 138: 3-[2-[(E)-5-[3-(Benzenesulfonamido)phenyl]-3,3-difluoropent-4-enoxy]phenyl]propanoic acid The same designed procedures as in Example 55→Example 56→Example 11 were carried out using, in place of (R,E)-5-(2-((E)-3-methoxy-3-oxoprop-1-en-1-yl)phenoxy)-1-(3-nitrophenyl)pent-1-en-3-yl benzoate used in Example 55, the compound produced in Example 137. In this manner, the title compound having the physical property values shown below was produced.

TLC: Rf 0.22 (hexane: ethyl acetate=1:2);
$^1$H-NMR (CDCl$_3$): δ 2.50-2.62, 2.72, 2.93, 4.20, 6.30, 6.80-6.95, 7.05, 7.12-7.25, 7.43, 7.53, 7.78, 7.89.

Example 139: 3-[2-[5-[3-(Benzenesulfonamido)phenyl]-3,3-difluoropentoxy]phenyl]propanoic acid

[Formula 57]

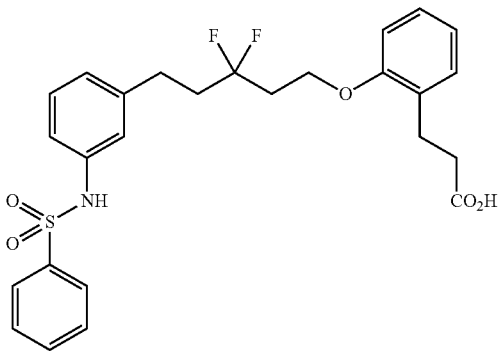

The same designed procedure as in Example 33 was carried out using, in place of 3-[2-[(E,3R)-5-[3-(benzenesulfonamido)phenyl]-3-hydroxypent-4-enoxy]phenyl]propanoic acid used in Example 33, the compound produced in Example 138. In this manner, the title compound having the physical property values shown below was produced.

TLC: Rf 0.20 (hexane: ethyl acetate=1:2);
$^1$H-NMR (CDCl$_3$): δ 2.14-2.47, 2.67-2.74, 2.76-2.84, 2.88-2.98, 4.13-4.21, 6.79-6.88, 6.89-7.07, 7.11-7.25, 7.42, 7.52, 7.79.

Example 140: (S)-5-((2-(2,2-Dimethyl-1,3-dioxolan-4-yl)ethyl)thio)-1-phenyl-1H-tetrazole 1-Phenyl-1H-tetrazole-5-thiol (CAS Registry Number: 86-93-1) (3.66 g), triphenylphosphine (5.38 g) and DIAD (1.10 g) were added to a solution of 2-[(S)-2,2-dimethyl-1,3-dioxolan-4-yl]ethanol (CAS Registry Number: 32233-43-5) (2.00 g) in THF (25 mL) at room temperature, and the resultant solution was stirred at the same temperature for 1 hour. The reaction solution was concentrated under a reduced pressure, and was then purified by silica gel column chromatography (hexane: ethyl acetate=7:1→2:1). In this manner, the title compound (4.14 g) having the physical property value shown below was produced.
HPLC retention time (min): 0.97.

Example 141: (S)-5-((2-(2,2-Dimethyl-1,3-dioxolan-4-yl)ethyl)sulfonyl)-1-phenyl-1H-tetrazole Ammonium molybdate tetrahydrate (1.57 g) and 30-wt % aqueous hydrogen peroxide (8.3 mL) were added to a solution of the compound produced in Example 140 (4.14 g) in acetonitrile (15 mL) and ethanol (15 mL) under ice cooling, and the resultant solution was stirred at room temperature for 16 hours. The reaction solution was concentrated under a reduced pressure, and an aqueous layer obtained was extracted with ethyl acetate. An organic layer was dried over sodium sulfate, and was then concentrated under a reduced pressure. The resultant residue was dissolved in 2,2-dimethoxypropane (8.3 mL), then p-toluenesulfonic acid monohydrate (129 mg) was added to the solution at room temperature, and the resultant solution was stirred at the same temperature for 1 hour. The reaction solution was diluted with ethyl acetate, and the resultant solution was washed with a saturated aqueous sodium bicarbonate solution and saturated saline. An organic layer was dried over sodium sulfate, and was then concentrated under a reduced pressure. The resultant residue was purified by silica gel column chromatography (hexane: ethyl acetate=7:1→2:1). In this manner, the title compound (3.96 g) having the physical property value shown below was produced.
HPLC retention time (min): 0.96.

Example 142: (S,E)-N-(3-(4,5-Dihydroxypent-1-en-1-yl)phenyl)benzenesulfonamide Potassium bis(trimethylsilyl)amide (a 0.5-M toluene solution, 15.3 mL) was added to a solution of the compound produced in Example 141 (1.04 g) in 1,2-dimethoxyethane (15 mL) at −78° C., and the resultant solution was stirred at the same temperature for 10 minutes. A solution of N-(3-formylphenyl)benzenesulfonamide (CAS Registry Number: 151721-35-6) (800 mg) in 1,2-dimethoxyethane (5 mL) was added to the reaction solution at −78° C., and the resultant solution was stirred at room temperature for 1 hour. A saturated aqueous ammonium chloride solution was added to the reaction solution, and the resultant solution was extracted with ethyl acetate. An organic layer was dried over sodium sulfate, and was then concentrated under a reduced pressure. The resultant residue was purified by silica gel column chromatography (hexane: ethyl acetate=10:1). The resultant residue was dissolved in methanol (3 mL), then 2 M hydrochloric acid (3 mL) was added to the solution at room temperature, and the resultant solution was stirred at 50° C. for 30 minutes. The reaction solution was ice-cooled, was then neutralized with a 2-M aqueous sodium hydroxide solution, and was the extracted with ethyl acetate. An organic layer was dried over sodium sulfate, and was then concentrated under a reduced pressure. The resultant residue was purified by silica gel column chromatography (hexane: ethyl acetate=1:0→9:1). In this manner, the title compound (675 mg) having the physical property value shown below was produced.
HPLC retention time (min): 0.73.

Example 143: (S,E)-1-Hydroxy-5-(3-(phenylsulfonamido)phenyl)pent-4-en-2-yl benzoate t-Butyldimethylchlorosilane (a 0.7-M DMF solution, 2 mL) was added dropwise to a solution of the compound produced in Example 142 (450 mg) and imidazole (131 mg) in DMF (5 mL) over 5 minutes under ice cooling, and the resultant solution was stirred at room temperature for 24 hours. The reaction solution was ice-cooled, then imidazole (131 mg) and t-butyldimethylchlorosilane (213 mg) were added to the solution, and the resultant solution was stirred at room temperature for 5 hours. Water was added to the reaction solution, and the resultant solution was extracted with ethyl acetate. An organic layer was dried over sodium sulfate, and was then concentrated under a reduced pressure. The resultant residue was dissolved in dichloromethane (5 mL), and then pyridine (0.42 mL), benzoyl chloride (215 mg) and DMAP (15.7 mg) were added to the solution under ice cooling, and the resultant solution was stirred at room temperature for 1.5 hours. The reaction solution was ice-cooled, then benzoyl chloride (215 mg) was added to the solution, and the resultant solution was stirred at room temperature for 1.5 hours. A saturated aqueous sodium bicarbonate solution was added to the reaction solution, and the resultant solution was extracted with ethyl acetate. An organic layer was dried over sodium sulfate, and was then concentrated under a reduced pressure. The resultant residue was purified by silica gel column chromatography (hexane: ethyl acetate=7:1→2:1). The resultant residue was dissolved in THF (3 mL) and acetic acid (0.30 mL), then TBAF (a 1.0-M THF solution, 1.6 mL) was added to the solution under ice cooling, and the resultant solution was stirred at room temperature for 12 hours. A saturated aqueous sodium bicarbonate solution was added to the reaction solution, and the resultant solution was extracted with ethyl acetate. An organic layer was dried over sodium sulfate, and was then concentrated under a reduced pressure. The resultant residue was purified by silica gel column chromatography (hexane: ethyl acetate=7:1→2:1). In this manner, the title compound (292 mg) having the physical property value shown below was produced.
HPLC retention time (min): 0.97.

Example 144: (S,E)-1-Iodo-5-(3-(phenylsulfonamido)phenyl)pent-4-en-2-yl benzoate Imidazole (68.6 mg) and triphenylphosphine (106 mg) were added to a solution of the compound produced in Example 143 (147 mg) in DMF (1 mL) at room temperature. Iodine (102 mg) was added to the reaction solution under ice cooling, and the resultant solution was stirred at 50° C. for 1.5 hours. The reaction solution was ice-cooled, then triphenylphosphine (26.0 mg) and iodine (25.0 mg) were added to the solution, and the resultant solution was stirred at 50° C. for 30 minutes. The reaction solution was purified by silica gel column chromatography (hexane: ethyl acetate=7:1→3:2). In this manner, the title compound (121 mg) having the physical property value shown below was produced.

HPLC retention time (min): 1.20.

Example 145: (S,E)-1-(2-(3-Isopropoxy-3-oxopropyl)phenoxy)-5-(3-(phenylsulfonamido)phenyl)pent-4-en-2-yl Benzoate Sodium hydride (60% in mineral oil, 13.1 mg) was added to a solution of the compound produced in Example 1 (68.4 mg) in DMF (0.5 mL) under ice cooling, and the resultant solution was stirred at room temperature for 15 minutes. A solution of the compound produced in Example 144 (60 mg) in DMF (0.5 mL) was added to the reaction solution at room temperature, and the resultant solution was stirred at 60° C. for 2 hours. The reaction solution was cooled to room temperature, and was then purified by silica gel column chromatography (hexane: ethyl acetate=7:1→3:2). In this manner, the title compound (12.1 mg) having the physical property value shown below was produced.

HPLC retention time (min): 1.29.

Example 146: 3-[2-[(E,2S)-5-[3-(Benzenesulfonamido)phenyl]-2-hydroxypent-4-enoxy]phenyl]propanoic acid The same designed procedure as in Example 57 was carried out using, in place of (R,E)-5-(2-((E)-3-methoxy-3-oxoprop-1-en-1-yl)phenoxy)-1-(3-(phenylsulfonamido)phenyl)pent-1-en-3-yl benzoate used in Example 57, the compound produced in Example 145. In this manner, the title compound having the physical property values shown below was produced.

HPLC retention time (min): 0.95
¹H-NMR (CD₃OD): δ 2.50, 2.59-2.65, 2.95-2.99, 3.95-4.02, 4.09, 6.29, 6.43, 6.86-6.96, 7.08-7.10, 7.12-7.20, 7.44-7.48, 7.54, 7.75-7.77.

Example 147: 2-(3-Nitrophenethoxy)acetic acid

A solution of 2-(3-nitrophenyl)ethanol (CAS Registry Number: 52022-77-2) (2.00 g) in DMF (4 mL) was cooled to 0° C., then sodium hydride (60% in mineral oil, 0.7 g) was added to the solution, and the resultant solution was stirred at 0° C. for 15 minutes. Isopropyl bromoacetate (2.6 g) was added dropwise to the solution, and the resultant solution was stirred at 0° C. for 1 hour and then at room temperature for 2 hours. The reaction mixture was poured into water, and the resultant solution as extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=10:0→2:1). In this manner, an ester compound (1.80 g) was produced. The ester compound was dissolved in methanol (15 mL), then sodium hydroxide (a 2-N aqueous solution, 10 mL) was added to the solution, and the resultant solution was stirred at room temperature overnight. The reaction mixture was poured into 2 M hydrochloric acid, and the resultant solution was extracted with ethyl acetate. An organic layer was washed with water and saturated saline, was then dried over sodium sulfate, and was then concentrated under a reduced pressure. In this manner, the title compound (1.15 g) having the physical property values shown below was produced.

¹H-NMR (CDCl₃): δ 3.05-3.07, 3.84-3.87, 4.14, 7.48, 7.58-7.60, 8.09-8.14.

Example 148: 2-(3-Nitrophenethoxy)ethan-1-ol

A solution of the compound produced in Example 147 (1.15 g) and 4-methylmorpholine (0.8 mL) in THF (10 mL) was cooled to 0° C., and then isobutyl chloroformate (0.8 mL) was added dropwise to the solution. The resultant solution was stirred at room temperature for 30 minutes to generate a white solid material, and the white solid material was filtrated out. A filtrate was cooled to 0° C., then sodium borohydride (1.15 g) was added to the filtrate, then the resultant solution was stirred at 0° C. for 10 minutes, then a small value of water was added to the solution, and the resultant solution was stirred at room temperature for 30 minutes. The reaction mixture was poured into water, and the resultant solution was extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=10:0→1:1). In this manner, the title compound (1.15 g) having the physical property values shown below was produced.

¹H-NMR (CDCl₃): δ 1.82, 3.00-3.03, 3.56-3.58, 3.69-3.78, 7.47, 7.56-7.58, 8.07-8.13.

Example 149: 3-[2-[2-[2-[3-(Benzenesulfonamido)phenyl]ethoxy]ethoxy]phenyl]propanoic Acid

[Formula 58]

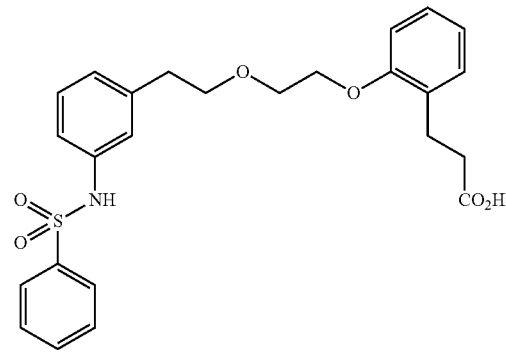

The same designed procedures as in Example 54→Example 55→Example 56→Example 11 were carried out using the compound produced in Example 148 in place of (R,E)-5-hydroxy-1-(3-nitrophenyl)pent-1-en-3-yl benzoate used in Example 54 and using the compound produced in Example 1 in place of methyl (E)-3-(2-hydroxyphenyl)prop-2-enoate used in Example 54. In this manner, the title compound having the physical property values shown below was produced.

HPLC retention time (min): 0.99;
¹H-NMR (DMSO-d6): δ 2.70-2.80, 3.17-3.18, 3.56-3.60, 3.68-3.71, 4.05-4.08, 6.84-6.96, 7.09-7.19, 7.50-7.60, 7.74-7.76.

Example 150: tert-Butyl (S)-2-(3-(1-hydroxy-2-phenylethyl)phenyl)acetate

Bromo-(2-tert-butoxy-2-oxo-ethyl)zinc (a 0.5-M THE solution, 9 mL) and bis(tri-tert-butylphosphine)palladium (76 mg) were added to a solution of (1S)-1-(3-bromophenyl)-2-phenyl-ethanol (412 mg) in THE (0.5 mL), and the resultant solution was stirred at 70° C. for 2 hours. The reaction mixture was cooled to room temperature, then a saturated aqueous ammonium chloride solution was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=4:1). In this manner, the title compound (296 mg) having the physical property value shown below was produced.

TLC: Rf 0.40 (hexane: ethyl acetate=4:1).

Example 151: tert-Butyl 2-(3-((1S)-2-phenyl-1-((tetrahydro-2H-pyran-2-yl)oxy)ethyl)phenyl)acetate 3,4-Dihydro-2H-pyran (239 mg) and pyridinium 4-toluenesulfonate (71 mg) were added to a solution of the compound produced in Example 150 (296 mg) in dichloromethane (2 mL), and the resultant solution was stirred at room temperature for 1.5 hours. A saturated aqueous sodium bicarbonate solution was added to the reaction mixture, and the resultant solution was extracted with dichloromethane. An organic layer was dried over sodium sulfate, and was then concentrated under a reduced pressure. The resultant residue was purified by silica gel column chromatography (hexane: ethyl acetate=4:1). In this manner, the title compound (341 mg) having the physical property value shown below was produced.

TLC: Rf 0.60 (hexane: ethyl acetate=4:1).

Example 152: 2-(3-((1S)-2-Phenyl-1-((tetrahydro-2H-pyran-2-yl)oxy)ethyl)phenyl)ethan-1-ol Water (0.15 mL) and lithium borohydride (187 mg) were added to a solution of the compound produced in Example 151 (341 mg) in THF (4 mL), and the resultant solution was stirred at 40° C. for 16 hours. Water was added to the reaction mixture, and was then extracted with ethyl acetate. An organic layer was dried over sodium sulfate, and was then concentrated under a reduced pressure. The resultant residue was purified by silica gel column chromatography (hexane: ethyl acetate=1:1). In this manner, the title compound (236 mg) having the physical property value shown below was produced.

TLC: Rf 0.50 (hexane: ethyl acetate=1:1).

Example 153: tert-Butyl 2-(3-((1S)-2-phenyl-1-((tetrahydro-2H-pyran-2-yl)oxy)ethyl)phenethoxy)acetate tert-Butyl bromoacetate (424 mg) and sodium hydride (60% in mineral oil, 87 mg) were added to a solution of the compound produced in Example 152 (236 mg) in DMF (2 mL), and the resultant solution was stirred at room temperature for 2.5 hours. A saturated aqueous sodium chloride solution was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=4:1). In this manner, the title compound (250 mg) having the physical property value shown below was produced.

TLC: Rf 0.60 (hexane: ethyl acetate=4:1).

Example 154: 2-(3-((1S)-2-Phenyl-1-((tetrahydro-2H-pyran-2-yl)oxy)ethyl)phenethoxy)ethan-1-ol Water (0.1 mL) and lithium borohydride (123 mg) were added to a solution of the compound produced in Example 153 (250 mg) in THE (0.5 mL), and the resultant solution was stirred at 40° C. for 2.5 hours. Water was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=1:1). In this manner, the title compound (107 mg) having the physical property value shown below was produced.

TLC: Rf 0.30 (hexane: ethyl acetate=1:1).

Example 155: Isopropyl (S)-3-(2-(2-(3-(1-hydroxy-2-phenylethyl)phenethoxy)ethoxy)phenyl)propanoate The compound produced in Example 1 (90 mg), triphenylphosphine (114 mg) and 1,1-(azodicarbonyl)dipiperidine (110 mg) were added to a solution of the compound produced in Example 154 (107 mg) in dichloromethane (1 mL), and the resultant solution was stirred at room temperature for 1.5 hours. The reaction mixture was concentrated under a reduced pressure. The resultant residue was purified by silica gel column chromatography (hexane: ethyl acetate=5:1) to produce an ester compound (181 mg). Water (0.8 mL) and acetic acid (3.2 mL) were added to a solution of the ester compound (181 mg) in THE (0.6 mL), and the resultant solution was stirred at 50° C. for 7 hours. A saturated aqueous sodium bicarbonate solution was added to the reaction mixture, and the resultant solution was extracted with ethyl acetate. An organic layer was dried over sodium sulfate, and was then concentrated under a reduced pressure. The resultant residue was purified by silica gel column chromatography (hexane: ethyl acetate=4:1). In this manner, the title compound (97 mg) having the physical property value shown below was produced.

TLC: Rf 0.20 (hexane: ethyl acetate=4:1).

Example 156: 3-[2-[2-[2-[3-[(1S)-1-Hydroxy-2-phenylethyl]phenyl]ethoxy]ethoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the compound produced in Example 155. In this manner, the title compound having the physical property values shown below was produced.

HPLC retention time (min): 1.10;
$^1$H-NMR (CDCl$_3$): δ 2.59-2.63, 2.90-2.94, 3.00-3.03, 3.76-3.80, 3.84-3.86, 4.10-4.13, 4.88, 6.82, 7.13-7.21, 7.22-7.32.

Example 157: 3-[2-[2-[2-[3-[(1R)-1-Hydroxy-2-phenylethyl]phenyl]ethoxy]ethoxy]phenyl]propanoic acid The same designed procedures as in Example 150→Example 151→Example 152→Example 153→Example 154→Example 155→Example 11 were carried out using, in place of (1S)-1-(3-bromophenyl)-2-phenyl-ethanol used in Example 150, the compound produced in Example 21. In this manner, the title compound having the physical property values shown below was produced.

HPLC retention time (min): 1.00;
$^1$H-NMR (CDCl$_3$): δ 2.58-2.62, 2.90-2.95, 2.99-3.06, 3.77-3.81, 3.84-3.86, 4.10-4.13, 4.88, 6.82, 6.88, 7.13-7.21, 7.25-7.32.

Example 158: tert-Butyl (trans-4-(3-hydroxypropyl)cyclohexyl)carbamate

A solution of methyl trans-3-[4-(tert-butoxycarbonylamino)cyclohexyl]propanoate (500 mg) in THF (5 mL) was cooled to 0° C., then a solution of lithium borohydride (72.8 mg) in THF (1 mL) was added to the solution, and the resultant solution was stirred at room temperature for 15 minutes then at 50° C. for 3 hours and a half. The reaction mixture was poured into a saturated aqueous sodium bicarbonate solution, and the resultant solution was extracted with ethyl acetate. An organic layer was washed with saturated saline, was then dried over sodium sulfate, and was then concentrated under a reduced pressure. In this manner, the title compound (429 mg) having the physical property values shown below was produced.

$^1$H-NMR (CDCl$_3$): δ 0.95-1.28, 1.44, 1.53-1.60, 1.75-1.78, 1.98-2.01, 2.27-2.31, 3.36, 3.62, 4.36.

Example 159: tert-Butyl (trans-4-(3-oxopropyl)cyclohexyl)carbamate

A solution of the compound produced in Example 158 (429 mg) in dichloromethane (8.3 mL) was cooled to 0° C., then 1,1,1-triacetoxy-1,1-dihydro-1,2-benziodoxol-3(1H)-one (848 mg) was added to the solution, and the resultant solution was stirred at room temperature for 3 hours. The reaction mixture was poured into a saturated aqueous sodium bicarbonate solution, and the resultant solution was extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=10:0→1:1). In this manner, the title compound (429 mg) having the physical property values shown below was produced.

$^1$H-NMR (CDCl$_3$): δ 0.96-1.28, 1.44, 1.53-1.60, 1.62-1.75, 1.98-2.01, 2.42-2.46, 3.36, 4.38.

Example 160: Ethyl (E)-5-(trans-4-((tert-butoxycarbonyl)amino)cyclohexyl)pent-2-enoate A solution of ethyl diethylphosphonoacetate (747 mg) in THF (5 mL) was cooled to 0° C., sodium hydride (60% in mineral oil, 145 mg) was then added to the solution, and the resultant solution was stirred at 0° C. for 15 minutes. A solution of the compound produced in Example 159 (429 mg) in THF (5 mL) was added to the reaction mixture, and the resultant solution was stirred at room temperature for 2 hours. The reaction mixture was poured into water, and the resultant solution as extracted with ethyl acetate. An organic layer was washed with saturated saline, was then dried over sodium sulfate, and was then concentrated under a reduced pressure. The resultant residue was purified by silica gel column chromatography (hexane: ethyl acetate=10:0→1:1). In this manner, the title compound (270 mg) having the physical property values shown below was produced.

$^1$H-NMR (CDCl$_3$): δ 0.95-1.38, 1.44, 1.53-1.59, 1.74-1.77, 1.98-2.01, 2.17-2.31, 3.36, 4.09-4.17, 4.35, 5.78-5.83, 6.91-7.00.

Example 161: Ethyl 5-(trans-4-((tert-butoxycarbonyl)amino)cyclohexyl)pentanoate Palladium on carbon (54 mg) was added to a solution of the compound produced in Example 160 (270 mg) in ethanol (10 mL), and the resultant solution was stirred at room temperature for 1 hour and a half under a hydrogen atmosphere. The reaction solution was filtrated through Celite (trade name), and a filtrate was concentrated under a reduced pressure. In this manner, the title compound (282 mg) having the physical property values shown below was produced.

$^1$H-NMR (CDCl$_3$): δ 0.95-1.38, 1.44, 1.53-1.59, 1.74-1.77, 1.98-2.01, 2.17-2.31, 3.36, 4.09-4.17, 4.35, 5.78-5.83, 6.91-7.00.

Example 162: tert-Butyl (trans-4-(5-hydroxypentyl)cyclohexyl)carbamate

A solution of the compound produced in Example 161 (282 mg) in THF (5 mL) was cooled to 0° C., lithium borohydride (36 mg) was added to the solution, and the resultant solution was stirred at 50° C. for 3 hours. The reaction mixture was poured into a saturated aqueous sodium bicarbonate solution, and the resultant solution was extracted with ethyl acetate. An organic layer was washed with saturated saline, was then dried over sodium sulfate, and was then concentrated under a reduced pressure. In this manner, the title compound (270 mg) having the physical property values shown below was produced.

$^1$H-NMR (CDCl$_3$): δ 0.92-1.32, 1.44, 1.53-1.60, 1.73-1.78, 1.98-2.01, 2.26-2.31, 3.36, 3.64, 4.36.

Example 163: 5-(trans-4-Aminocyclohexyl)pentan-1-ol hydrochloride

Hydrogen chloride (a 4.0-M dioxane solution, 6 mL) was added to the compound produced in Example 162 (140 mg), and the reaction mixture was stirred at room temperature for 1 hour and a half, and was then concentrated. In this manner, the title compound (180 mg) having the physical property values shown below was produced.

$^1$H-NMR (DMSO-d6): δ 0.88-0.97, 1.15-1.42, 1.73-1.76, 1.90-1.93, 2.91, 3.36-3.75, 7.86.

Example 164: 5-(trans-4-(Phenylsulfonamido)cyclohexyl)pentyl benzene sulfonate A solution of the compound produced in Example 163 (180 mg) in pyridine (2 mL) and dichloromethane (2 mL) was cooled to 0° C., and DMAP (5 mg) was then added to the solution. Benzenesulfonyl chloride (0.14 mL) was added dropwise to the reaction solution, and the resultant solution was stirred at room temperature overnight. The reaction mixture was poured into 1 M hydrochloric acid, and the resultant solution was extracted with ethyl acetate. An organic layer was washed with a saturated aqueous sodium bicarbonate solution and saturated saline, was then dried over sodium sulfate, and was then concentrated under a reduced pressure. In this manner, the title compound (180 mg) having the physical property values shown below was produced.

$^1$H-NMR (CDCl$_3$): δ 0.84-0.89, 1.07-1.83, 3.04-3.09, 3.98-4.27, 7.51-8.07.

Example 165: Isopropyl 3-(2-((5-(trans-4-(phenylsulfonamido)cyclohexyl)pentyl)oxy)phenyl)propanoate Cesium carbonate (377 mg) was added to a solution of the compound produced in Example 164 (180 mg) in 1-methyl-2-pyrrolidone (2 mL), and the reaction mixture was stirred at 50° C. for 2 hours. The reaction mixture was poured into water, and the resultant solution as extracted with ethyl acetate. An organic layer was washed with water and saturated saline, was then dried over sodium sulfate, and was then concentrated under a reduced pressure. The resultant residue was purified by silica gel column chromatography (hexane: ethyl acetate=10:0→2:1). In this manner, the title compound (60 mg) having the physical property values shown below was produced.

$^1$H-NMR (CDCl$_3$): δ 0.83-0.92, 1.07-1.84, 2.53-2.57, 2.89-2.93, 3.04-3.12, 3.92-3.95, 4.26-4.27, 4.96-5.02, 6.79-6.86, 7.13-7.17, 7.48-7.59, 7.87-7.89.

Example 166: 3-[2-[5-[4-(Benzenesulfonamido) cyclohexyl]pentoxy]phenyl]propanoic acid The same designed procedure as in Example 11 was carried out using, in place of propan-2-yl 3-[2-[(E,3R)-5-[3-(benzenesulfonamido)phenyl]-3-hydroxypent-4-enoxy]phenyl]propanoate used in Example 11, the ester compound produced in Example 165. In this manner, the title compound having the physical property values shown below was produced.

HPLC retention time (min): 1.20;
$^1$H-NMR (CDCl$_3$): δ 0.83-0.92, 1.07-1.83, 2.64-2.68, 2.92-2.96, 3.05-3.13, 3.93-3.96, 4.42-4.43, 6.80-6.88, 7.14-7.20, 7.48-7.59, 7.87-7.89.

Hereinbelow, biological experiment examples will be shown. The effects of the compounds of the present invention were confirmed by these experimental methods.

Biological Experiment Example 1: In Vitro Test Using Schwann Cells (Test Method)
(1) Preparation of rat Schwann cells
A dorsal root ganglion (abbreviated as "DRG", hereinafter) was excised from a newborn rat aged 0 to 2 days in a clean bench and was collected in DMEM. After the collection, the tube was centrifuged at 400 g, at room temperature for 3 minutes, then a supernatant was discarded, and a 0.25% collagenase solution was added. There resultant solution was incubated at 37° C. for 30 minutes to disperse and separate the excised DRG, and was then centrifuged at room temperature at 400 g for 3 minutes, then a supernatant was discarded, and then 0.25% Trypsin/EDTA and DNaseI were added. After the incubation at 37° C. for 30 minutes, trypsin was inactivated with DMEM supplemented with 10% FBS (10% FBS-DMEM), and centrifugation was carried out at room temperature at 400 g for 3 minutes. A supernatant was discarded, then 10% FBS-DMEM was added to the residue to prepare a cell suspension, and then the cell suspension was allowed to pass through a filter (diameter: 70 μm). The number of cells in the cell suspension which passed through the filter was counted to prepare a solution having a concentration of 2.0×10$^5$ cells/mL, and the suspension was seeded in a poly-D-lysine-coated 96-well black-clear plate in an amount of 100 μL/well and was then statically cultured in a CO$_2$ incubator under the conditions including 5% of CO$_2$, 95% of air and 37° C.

(2) Addition of Compound
The culture medium in the cell culture plate was removed by suction using an aspirator, and then DMEM supplemented with 1% dialyzed FBS and 100 μmol/L dibutyryl cyclic AMP was added. Subsequently, a solution of a compound of the present invention dissolved in DMSO was added, and the resultant solution was statically cultured in a C02 incubator under the conditions including 5% of C02, 95% of air and a temperature of 37° C. The final concentration of the compound of the present invention in each well in the cell culture plate was adjusted to 0.1, 0.3, 1 or 3 μmol/L.

(3) Cell Immunostaining
Three days after the treatment with the compound, formaldehyde was added to each well in the cell culture plate, and the cell culture plate was allowed to stand at room temperature for 30 minutes or longer. A supernatant was discarded, and then a 0.3% tritonX-100 solution was added to each well, and then the cell culture plate was allowed to stand at room temperature for 20 minutes or longer. A supernatant was discarded, then a 5-μg/mL anti-myeline-associated glycoprotein antibody (anti-MAG antibody) solution was added to each well, and then the cell culture plate was allowed to stand at room temperature for 60 minutes or longer or at 4° C. (acceptable range: 1 to 9° C.) overnight. Each well was washed with a 0.1% tritonX-100 solution three times, then a 10-μg/mL Alexa fluor 488 anti-mouse IgG solution was added to each well, and then the cell culture plate was allowed to stand at room temperature for 60 or longer or at 4° C. overnight. Each well was washed with a 0.1% tritonX-100 solution four times, and then a 1-μg/mL Hoechst33342 solution was added to each well to stain nuclei.

(Evaluation Method)
The Mag-positive area and the number of cell nuclei in a fluorescent image were calculated. With respect to each of the MAG-positive area and the number of cell nuclei, the sum total of values obtained in 5 viewing fields/well was determined. The values were employed as a value for the MAG-positive area and a value for the number of cell nuclei, respectively, in each well. Subsequently, a value determined by dividing the value for the MAG-positive area in each well by the value for the number of cell nuclei in the well (i.e., MAG/cell nuclei numerical value) was calculated. The Schwann cell differentiation promotion rate was determined for each of the vehicles in accordance with the following formula.

$$\text{Schwann cell differentiation promotion rate for vehicle (\%)} = \{(MAG \text{ of compound of invention/cell nuclei numerical value}) - A\}/(B-A) \times 100 \quad \text{[Math 1]}$$

A: MAG/cell nuclei numerical value in untreated plate
B: MAG/cell nuclei numerical value of vehicle (Results)
Schwann cell differentiation promotion rates (% of vehicle) for the vehicles in the case where each of the compounds of the present invention was added at a concentration of 0.3 or 3 μmol/L are shown below. From these results, it was considered that the compounds of the present invention had a potent nerve-protecting and/or -repairing activity.

TABLE 1

| Example No. | % of vehicle | |
|---|---|---|
| | 0.3 μmol/L | 3 μmol/L |
| 10 | 86.2 | 593.4 |
| 11 | 113.7 | 248.1 |
| 12(1) | 120.0 | 274.5 |
| 12(5) | 146.7 | 234.5 |
| 12(6) | 143.5 | 435.1 |
| 12(7) | 110.8 | 379.4 |
| 12(8) | 157.9 | 458.8 |
| 12(11) | 202.8 | 505.4 |
| 13(15) | 219.1 | 325.8 |
| 13(16) | 169.9 | 376.9 |
| 13(19) | 142.1 | 598.0 |
| 26 | 195.5 | 438.6 |
| 28 | 187.8 | 628.2 |
| 32(1) | 408.0 | 1007.4 |
| 32(2) | 340.3 | 787.5 |
| 36 | 125.7 | 732.1 |
| 37 | 170.6 | 914.9 |
| 39 | 211.3 | 322.6 |
| 74(13) | 79.9 | 184.2 |
| 74(15) | 204.5 | 428.1 |
| 74(16) | 212.0 | 300.5 |
| 74(17) | 85.6 | 252.4 |
| 74(19) | 187.0 | 270.0 |
| 75 | 181.0 | 244.4 |
| 77 | 115.1 | 255.6 |
| 84 | 161.9 | 445.3 |
| 93 | 107.7 | 373.7 |
| 103 | 198.7 | 353.9 |
| 112 | 255.0 | 503.7 |
| 139 | 208.6 | 541.0 |
| 149 | 159.6 | 644.6 |
| 166 | 103.7 | 464.6 |

Biological Experiment Example 2: Test Using Streptozotocin-Induced Rat Model

In order to evaluate the therapeutic effect of each of the compounds of the present invention on diabetic peripheral neuropathy, an in vivo test using a streptozotocin model was carried out.

(Test Method)

(1) Production of Model

A model was produced by intravenously administering streptozotocin (abbreviated as "STZ", hereinafter) one time at a dose amount of 55 mg/kg to a rat.

(2) Measurement of Nociceptive Threshold

The rat was placed in a clear acryl measurement cage once or more times for 10 minutes or longer until the administration of STZ started. In this manner, the rat was acclimated to the measurement environment. Eight von Frey filaments respectively having weights of 0.4, 0.6, 1, 2, 4, 6, 8 and 15 g were applied vertically to a hindpaw of the rat from under a metallic mesh floor. When a quick escape or flinching reaction was observed, it was determined that a positive reaction occurred (i.e., "response was observed"). Each of the compounds of the present invention was administered orally once per day in a period from day 14 to day 28 after the administration of STZ, wherein the dose amount of each of the compounds was 0.03, 0.3 or 3 mg/kg. A nociceptive threshold was measured 2 hours after the administration of each of the compounds of the present invention at the timings of before the administration of STZ, 14 days after the administration of STZ (i.e., the day of the start of the administration of each of the compounds of the present invention), 21 days after the administration of STZ (i.e., 7 days after the start of the administration of the compound), 28 days after the administration of STZ (i.e., 14 days after the start of the administration of the compound), and 35 days after the administration of STZ (i.e., 7 days after the withdrawal of the administration of the compound).

(Evaluation Method)

The nociceptive threshold was measured by the up-down method in accordance with the method of Chaplan et. al. (J Neurosci Methods. 1994; 53:55-63). The rate of improvement in the nociceptive threshold was calculated in accordance with the following formula.

$$\text{Nociceptive threshold improve rate (\%)} = (\text{nociceptive threshold on each of the number of days elapsed after administration of } STZ - B)/(A - B) \times 100 \qquad [\text{Math 2}]$$

A: Nociceptive threshold before administration of STZ
B: Nociceptive threshold on 14 days elapsed after administration of STZ (Results)

The results of the nociceptive thresholds and the nociceptive threshold improve rates obtained when each of the compounds of the present invention was administered at a dose amount of 0.3 mg/kg are shown in the FIGURE and Table 2, respectively. With respect to all of the compounds, a potent pain relief effect against peripheral neuropathy was observed. With respect to the compound of Example 11, for example, the improvement in the nociceptive threshold was observed from 7 days after the start of the administration of the compound, and this effect lasted even 7 days after the withdrawal of the administration. Therefore, a sustained pain relief effect was confirmed.

TABLE 2

| | Nociceptive threshold improve rate (%) | | | |
|---|---|---|---|---|
| Example No. | After initial single administration | 7 days after start of administration | 14 days after start of administration | 7 days after withdrawal of administration |
| 11 | −14.6 ± 6.37 | 26.6 ± 9.30 | 27.1 ± 8.39 | 41.1 ± 13.71 |
| 12(1) | 6.2 ± 5.72 | 17.4 ± 17.19 | 44.6 ± 11.54 | 9.1 ± 13.37 |
| 13(15) | −15.4 ± 14.26 | 15.9 ± 7.17 | 8.5 ± 11.50 | 7.1 ± 9.51 |
| 13(16) | −6.0 ± 3.87 | 25.8 ± 5.28 | 29.6 ± 8.19 | −7.8 ± 14.90 |
| 36 | 3.6 ± 7.07 | 57.1 ± 13.78 | 64.2 ± 13.02 | 57.4 ± 10.74 |
| 37 | −11.9 ± 10.78 | 61.3 ± 16.58 | 78.9 ± 9.85 | 58.7 ± 19.84 |
| 74(13) | 2.6 ± 1.69 | 28.3 ± 7.44 | 57.3 ± 17.63 | 76.3 ± 13.41 |
| 84 | 5.7 ± 2.48 | 35.0 ± 16.24 | 49.9 ± 11.50 | 58.8 ± 12.51 |

Biological Experiment Example 3: Reactive metabolite measurement test

A complex of a reactive metabolite of each of the compounds of the present invention and quaternary ammonium glutathione (QA-GSH) was semi-quantified by LC/MS/MS (Soglia J R et al., Chem. Res. Toxicol. 19(3), 480-490, 2006), and the NADPH-dependent reactive metabolite amount was measured.

To a 100-mM phosphate buffer (pH 7.4) (187.5 µL) were added 20 mg/mL of human liver microsomes (Xenotech) in an amount of 12.5 µL (final concentration: 1 mg/mL), 10 mmol/L of QA-GSH in an amount of 25 µL (final concentration: 1 mmol/L), and 0.5 mmol/L of a solution of each of the compounds of the present invention (DMSO: acetonitrile: water=5:38:57) in an amount of 5 µL (final concentration of the compound: 10 µmol/L). The resultant solution was preincubated in a water bath at 37° C. for 3 minutes, and then 25 mmol/L of NADPH was added in an amount of 20 µL (final concentration: 2 mmol/L) to the solution to initiate the reaction. After the reaction was carried out for 1 hour, 500 µL of IS-containing acetonitrile was admixed with the reaction solution to terminate the reaction. A complex of a reactive metabolite and QA-GSH (i.e., a QA-GS adduct) produced in the reaction-terminated sample was analyzed by LC/MS/MS. The measurement was also carried out on an internal standard (IS) substance for the QA-GS adduct.

The concentration of the QA-GS adduct was calculated in accordance with the following formula.

$$\text{Concentration of QA-GS adduct} = (\text{area of peak corresponding to QA-GS adduct})/(\text{area of peak corresponding to IS}) \times (\text{concentration of IS}) \qquad [\text{Math 3}]$$

(Results)

The concentration of a QA-GS adduct of each of the compounds of the present invention was low. For example, all of the concentrations of QA-GS adducts of the compounds of Examples 11, 36, 37, 74(13), 84 and 149 were 200 nmol/L or less.

Biological Experiment Example 4: Hand-1EST Test

The reproductive and developmental toxicity of each of the compounds of the present invention was measured using POCA (registered trademark) Hand1-EST (DS Pharma Biomedical Co., Ltd.) employing, as measures, the number of living cells and the differentiation efficiency in the process of differentiation from a murine ES cell to a cardiac muscle (Le Coz F et al., J. Toxicol., 40(2):251-61. 2015).

A 1000-mg/mL solution of each of the compounds of the present invention in DMSO was prepared. The 1000-mg/mL solution of each of the compounds of the present invention in DMSO was diluted with a cardiac muscle differentiation culture medium to prepare a 1000-µg/mL solution of the compound (final concentration of DMSO: 0.1%). The solution was three-fold diluted sequentially with a cardiac muscle differentiation culture medium (final concentration of DMSO: 0.1%) while confirming the presence or absence of precipitates with naked eyes, and a concentration at which no precipitated was observed was recorded as a maximum solubility.

Thawed Hand1-ES cells (murine ES cells each of which had been transfected with a promoter region for a cardiac muscle differentiation marker Hand1 gene and a luciferase gene located downstream of the promoter region using pGL4.17 as a vector) were suspended in an undifferentiated state maintenance culture medium, and the resultant solution was seeded in a gelatin-coated 60-mm dish and was then cultured for 2 to 3 days. After the culture was carried out for 2 to 3 days, the trypsin-treated Hand1-ES cells were sub-cultured at a concentration of $2\times10^6$ cells/5 mL in a gelatin-coated 60-mm dish and were then cultured overnight. Subsequently, the trypsin-treated Hand1-ES cells were suspended in a cardiac muscle differentiation culture medium, and the resultant solution was seeded in a Prime-Surface (registered trademark) U-bottomed 96-well plate at a concentration of 750 cells/50 µL/well and was then cultured for 2 hours. After 2 hours, 50 µL of a cardiac muscle differentiation culture medium containing each of the compounds of the present invention or a positive control substance 5-FU was added (final concentration of the compound of the present invention: 1000, 333, 111, 37.0, 12.3, 4.12 and 1.37 g/mL; final concentration of 5-FU: 1, 0.333, 0.111, 0.0370, 0.0123, 0.00412 and 0.00137 g/mL; final concentration of DMSO: 0.1%) for 5 days. After the compounds of the present invention or 5-FU was exposed to the cells for 5 days, in order to determine the number of living cells, CellTiter-Fluor (registered trademark) (Promega) was added and the fluorescence at an excitation wavelength Ex of 390 nm and a fluorescent wavelength Em of 505 nm was measured using SpectraMax M5e plate reader (Molecular Devices). Furthermore, in order to determine a differentiation efficiency, Steady-Glo (registered trademark) (Promega) was added and a fluorescence was measured using SpectraMax M5e plate reader. The maximum solubility, the concentration at which the number of living cells was inhibited by 50% and the concentration at which the differentiation efficiency was inhibited by 50%, which were determined above, were input to a special analysis software POCA Hand1-EST Analysis Software to determine a teratogenic risk. The criteria for the determination were as follows: low risk: provability was less than 0.52; high risk: probability was 0.52 or more (Nagahori et al., Toxicology Letters 259, 44-51).

(Results)

Among the compounds of the present invention, each of the compounds of Examples 84, 86 and 87 had a probability of less than 0.52, and therefore it was considered that these compounds had low teratogenic risk.

FORMULATION EXAMPLES

Formulation Example 1

The components shown below are mixed together in the conventional manner and the mixture is compressed into tablets. In this manner, 10,000 tablets each containing 10 mg of the active component per tablet are produced.

3-[2-[(E,3R)-5-[3-(Benzenesulfonamido)phenyl]-3-hydroxypent-4-enoxy]phenyl]propanoic acid: 100 g Carboxymethyl cellulose potassium: 20 g Magnesium stearate: 10 g Microcrystalline cellulose: 870 g Formulation Example 2

The components shown below are mixed together in the conventional manner, then the mixture is filtrated through a dust filter, then a filtrate is packed in ampules in a volume of 5 ml per ampule, and the ampules are thermally sterilized with an autoclave. In this manner, 10,000 ampules each containing the active ingredient in an amount of 20 mg/ampule are produced.

3-[2-[(E,3R)-5-[3-(Benzenesulfonamido)phenyl]-3-hydroxypent-4-enoxy]phenyl]propanoic acid: 200 g Mannitol: 20 g Distilled water: 50 L

INDUSTRIAL APPLICABILITY

The compound of the present invention has a potent nerve-protecting and/or -repairing activity, and is therefore useful for the prevention and/or treatment of diseases associated with neuropathies.

The invention claimed is:

1. A method of promoting differentiation of a Schwann cell, comprising contacting a cell with 3-[2-[(E)-5-[3-(benzenesulfonamido)phenyl]pent-4-enoxy]phenyl]propanoic acid or a salt thereof.

2. The method according to claim 1, wherein the cell is contacted with 3-[2-[(E)-5-[3-(benzenesulfonamido)phenyl]pent-4-enoxy]phenyl]propanoic acid.

3. The method according to claim 1, wherein the cell is contact with a salt of 3-[2-[(E)-5-[3-(benzenesulfonamido)phenyl]pent-4-enoxy]phenyl]propanoic acid.

4. A method for preventing or treating neuropathy, comprising administering an effective amount of 3-[2-[(E)-5-[3-(benzenesulfonamido)phenyl]pent-4-enoxy]phenyl]propanoic acid or a salt thereof to a mammal.

5. The method according to claim 4, wherein 3-[2-[(E)-5-[3-(benzenesulfonamido)phenyl]pent-4-enoxy]phenyl]propanoic acid is administered.

6. The method according to claim 4, wherein a salt of 3-[2-[(E)-5-[3-(benzenesulfonamido)phenyl]pent-4-enoxy]phenyl]propanoic acid is administered.

7. The method according to claim 4, wherein the neuropathy is a peripheral neuropathy.

8. The method according to claim 7, wherein the peripheral neuropathy is chronic inflammatory demyelinating polyneuropathy, Guillain-Barre syndrome, periarteritis nodosa, allergic vasculitis, diabetic peripheral neuropathy, entrapment neuropathy, peripheral neuropathy associated with Charcot-Marie-Tooth disease, peripheral neuropathy associated with an infectious disease, a drug-induced peripheral neuropathy associated with the administration of an anti-convulsant agent, an anti-microbial agent, a chemotherapeutic drug or a sedative agent, multifocal motor neuropathy or a toxic peripheral neuropathy associated with the ingestion of a heavy metal, an organic solvent, a toxic substance or an alcohol.

9. The method according to claim 4, wherein the mammal is a human.

10. The method according to claim 8, wherein the drug-induced peripheral neuropathy is peripheral neuropathy associated with the administration of a chemotherapeutic drug.

11. The method according to claim 4, wherein the neuropathy is central neuropathy.

12. The method according to claim 11, wherein the central neuropathy is amyotrophic lateral sclerosis.

* * * * *